United States Patent
Ishikawa et al.

(10) Patent No.: US 9,604,988 B2
(45) Date of Patent: Mar. 28, 2017

(54) AGENT FOR TREATING OR INHIBITING RECURRENCE OF ACUTE MYELOID LEUKEMIA

(71) Applicant: RIKEN, Wako-shi, Saitama (JP)

(72) Inventors: Fumihiko Ishikawa, Saitama (JP); Yoriko Saito, Wako (JP); Yoshinobu Hashizume, Wako (JP); Yasuko Koda, Wako (JP); Hitomi Yuki, Wako (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 14/417,250

(22) PCT Filed: Jul. 29, 2013

(86) PCT No.: PCT/JP2013/070436
§ 371 (c)(1),
(2) Date: Jan. 26, 2015

(87) PCT Pub. No.: WO2014/017659
PCT Pub. Date: Jan. 30, 2014

(65) Prior Publication Data
US 2015/0210698 A1    Jul. 30, 2015

Related U.S. Application Data

(60) Provisional application No. 61/811,975, filed on Apr. 15, 2013.

(30) Foreign Application Priority Data

Jul. 27, 2012  (JP) .................................. 2012-167553

(51) Int. Cl.
*C07D 487/04* (2006.01)
*A61K 31/519* (2006.01)
(Continued)

(52) U.S. Cl.
CPC ........ *C07D 487/04* (2013.01); *A61K 31/4709* (2013.01); *A61K 31/4985* (2013.01);
(Continued)

(58) Field of Classification Search
CPC . C07D 487/04; A61K 31/519; A61K 31/4985
(Continued)

(56) References Cited

U.S. PATENT DOCUMENTS 6,713,474 B2 *  3/2004  Hirst ................... C07D 487/04
                                                    514/218
2003/0153752 A1   8/2003  Hirst et al.
(Continued)

FOREIGN PATENT DOCUMENTS

JP    2002-526500 A    8/2002
JP    2004-531513 A    10/2004
(Continued)

OTHER PUBLICATIONS

Wolff Manfred E. "Burger's Medicinal Chemistry, 5ed, Part 1" John Wiley & Sons, 1995, pp. 975-977.*
Banker, G.S. et al, "Modern Pharmaceutices, 3ed.", Marcel Dekker, New York. 1996, pp. 451 and 596.*
Borhani et al., "A-420983: a potent, orally active inhibitor of Ick with efficacy in a model of transplant rejection," Bioorganic & Medicinal Chemistry Letters, May 17, 2004, vol. 14, No. 10, pages.
Calderwood et al., "Pyrrolo[2,3-*d*]pyrimidines Containing Diverse N-7 Substituents as Potent Inhibitors of Lck," Bioorganic & Medicinal Chemistry Letters, Jun. 1, 2002, vol. 12, No. 12, pp. 1683-1686.
Extended European Search Report for EP Application No. 13823379.6, dated Dec. 2, 2015, 10 pages.
Mitina, et al., "Src family tyrosine kinases phosphorylate Flt3 on juxtamembrane tyrosines and interfere with receptor maturation in a kinase-dependent manner," Annals of Hematology, Aug. 1, 2007, vol. 86, No. 11, pp. 777-785.
Schenone et al., "Fyn Kinase in Brain Diseases and Cancer: The Search for Inhibitors," Current Medicinal Chemistry, Jun. 1, 2011, vol. 18, No. 19, pp. 2921-2942.
(Continued)

*Primary Examiner* — Venkataraman Balasubramanian
(74) *Attorney, Agent, or Firm* — Foley & Lardner LLP

(57) ABSTRACT

This invention relates to an agent for treating or inhibiting recurrence of acute myeloid leukemia and an agent for inhibiting growth of leukemia stem cells comprising a compound represented by formula (I) or a salt thereof:

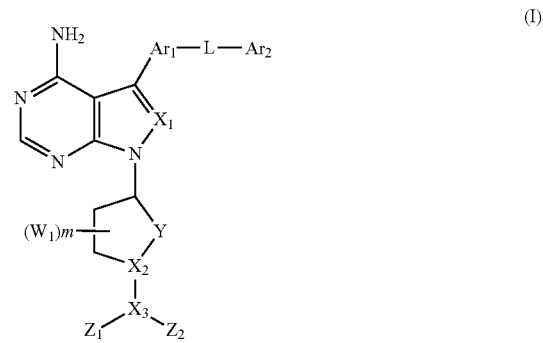

wherein $Ar_1$ and $Ar_2$ each represent aryl or heteroaryl; L represents O, S, NH, NHCO, or CONH; X represents CH or N; Y represents $C_{1-3}$-alkylene; $Z_1$ represents hydrogen, $C_{1-6}$-alkyl, amino-$C_{1-6}$-alkyl, $C_{1-6}$-alkylamino-$C_{1-6}$-alkyl, di($C_{1-6}$-alkyl)amino-$C_{1-6}$-alkyl, hydroxy-$C_{1-6}$-alkyl, $C_{1-6}$-alkoxy-$C_{1-6}$-alkyl, or carboxy-$C_{1-6}$-alkyl; and $Z_2$ represents $C_{1-6}$-alkyl, amino-$C_{1-6}$-alkyl, $C_{1-6}$-alkylamino-$C_{1-6}$-alkyl, di($C_{1-6}$-alkyl)amino-$C_{1-6}$-alkyl, hydroxy-$C_{1-6}$-alkyl, $C_{1-6}$-alkoxy-$C_{1-6}$-alkyl, or carboxy-$C_{1-6}$-alkyl, $Z_1$ and $Z_2$ may, together with adjacent nitrogen, form a heterocyclic group containing as a ring member one or more hetero atoms, in addition to the nitrogen adjacent to $Z_1$ and $Z_2$.

21 Claims, 7 Drawing Sheets

(51) Int. Cl.
  *A61K 31/4985* (2006.01)
  *A61P 35/02* (2006.01)
  *A61K 45/06* (2006.01)
  *A61K 31/4709* (2006.01)
  *A61K 31/7105* (2006.01)
  *A61K 31/713* (2006.01)
  *C07D 519/00* (2006.01)
  *C12Q 1/68* (2006.01)

(52) U.S. Cl.
  CPC .......... *A61K 31/519* (2013.01); *A61K 31/713* (2013.01); *A61K 31/7105* (2013.01); *A61K 45/06* (2013.01); *C07D 519/00* (2013.01); *C12Q 1/6886* (2013.01); *C12Q 2600/106* (2013.01); *C12Q 2600/156* (2013.01); *C12Q 2600/16* (2013.01)

(58) Field of Classification Search
  USPC .................... 544/262, 280; 514/262.1, 265.1
  See application file for complete search history.

(56) References Cited

U.S. PATENT DOCUMENTS

| | | | |
|---|---|---|---|
| 2006/0025383 A1* | 2/2006 | Wishart | C07D 487/04 514/63 |
| 2012/0070450 A1 | 3/2012 | Ishikawa et al. | |
| 2012/0121535 A1 | 5/2012 | Ishikawa et al. | |

FOREIGN PATENT DOCUMENTS

| | | |
|---|---|---|
| JP | 2005-501811 A | 1/2005 |
| JP | 2006-507841 A | 3/2006 |
| JP | 2007-520559 A | 7/2007 |
| JP | 2012-508179 A | 4/2012 |
| WO | WO 00/17203 A1 | 3/2000 |
| WO | WO 01/19829 A2 | 3/2001 |
| WO | WO 02/076986 A1 | 10/2002 |
| WO | WO 02/080926 A1 | 10/2002 |
| WO | WO 2004/045543 A2 | 6/2004 |
| WO | WO 2004/100868 A2 | 11/2004 |
| WO | WO 2005/074603 A2 | 8/2005 |
| WO | WO 2007/142139 A1 | 12/2007 |
| WO | WO 2010/054058 A1 | 5/2010 |
| WO | WO 2010/101257 A1 | 9/2010 |
| WO | WO 2010/110346 A1 | 9/2010 |

OTHER PUBLICATIONS

Burchat et al., "Discovery of A-770041, a src-family selective orally active lck inhibitor that prevents organ allograft rejection," Bioorganic & Medicinal Chemistry Letters, 2006, (published online Oct. 10, 2005), 16:118-122.

Hope et al., "Acute myeloid leukemia originates from a hierarchy of leukemic stem cell classes that differ in self-renewal capacity," Nature Immunology, Jul. 2004, published online May 30, 2004, 5(7):738-743.

Ishikawa et al., "Chemotherapy-resistant human AML stem cells home to and engraft within the bone-marrow endosteal region," Nature Biotechnology, Nov. 2007, published online Oct. 21, 2007, 25(11):1315-1321.

Jordan et al., "Mechanisms controlling pathogenesis and survival of leukemic stem cells," Oncogene, 2004, 23:7178-7187.

Passegue et al., "Normal and leukemic hematopoiesis: Are leukemias a stem cell disorder or a reacquisition of stem cell characteristics?", PNAS, Sep. 30, 2003, 100(Suppl.1):11842-11849.

Saito et al., "Induction of cell cycle entry eliminates human leukemia stem cells in a mouse model of AML," Nature Biotechnology, Mar. 2010, 28(3):275-280.

Saito et al., "Identification of Therapeutic Targets for Quiescent, Chemotherapy-Resistant Human Leukemia Stem Cells," Science Translational Medicine, Feb. 3, 2010, 2(17):17ra9, 1-12.

Wang et al., "Substituted 4-amino-1H-pyrazolo[3,4-d]pyrimidines as multi-targeted inhibitors of insulin-like growth factor-1 receptor (IGF1R) and members of ErbB-family receptor kinases," Bioorganic & Medicinal Chemistry Letters, Aug. 13, 2010, 20:6067-6071.

* cited by examiner

AGENT FOR TREATING OR INHIBITING RECURRENCE OF ACUTE MYELOID LEUKEMIA

CROSS-REFERENCE TO RELATED APPLICATIONS

This application is a National Stage application of PCT/JP2013/070436 filed Jul. 29, 2013, which claims priority from Japanese Application No. JP 2012-167553, filed Jul. 27, 2012, and U.S. Provisional Application No. 61/811,975, filed Apr. 15, 2013.

TECHNICAL FIELD

The present invention relates to an agent for treating or inhibiting recurrence of acute myeloid leukemia.

BACKGROUND ART

Acute myeloid leukemia (hereafter also referred to as "AML") is a hematological malignancy with a poor prognosis that often occurs in adults, and the 5-year survival rate thereof is predicted to be 20%. At present, it is possible to temporarily reduce the number of AML cells to a level below the detection limit through AML treatment. This condition is referred to as "complete remission." However, AML often recurs after achieving complete remission, and for many patients, recurrent AML results in death. Accordingly, there is an urgent need to prevent recurrence and establish a radical treatment method for AML.

While conventional chemotherapeutic agents would realize temporary remission of AML, its recurrence has been an issue of concern. In particular, a very low survival rate in cases of recurrence has been a serious issue of concern.

To date, the present inventors have demonstrated that elimination of leukemia stem cells (hereafter also referred to as "LSCs") is critical for achieving radical cure for AML and that the LSCs are generally in the stationary phase of a cell cycle in bone marrow niches (Patent Document 1 and Non-Patent Documents 4 and 5). They have also demonstrated LSC-specific genes on the basis of gene expression comparison between LSCs and normal hematopoietic stem cells (hereafter also referred to as "HSCs") (Patent Document 2 and Non-Patent Document 6).

Patent Document 3 describes that 5,7-disubstituted-7H-pyrrolo[2,3-d]pyrimidin-4-amine, which is represented by a general formula encompassing numerous compounds, would inhibit various types of kinase functions and is effective for treatment of various types of diseases, including leukemia.

Also, Patent Document 4 describes 5,7-disubstituted-7H-pyrazolo[3,4-d]pyrimidin-4-amine having kinase inhibitory activity.

However, neither Patent Document 3 nor Patent Document 4 provide any concrete evidence that supports the kinase inhibitory activity or pharmacological activity of any compounds.

PRIOR ART DOCUMENTS

Patent Documents

Patent Document 1: WO 2010/101257
Patent Document 2: WO 2010/110346
Patent Document 3: WO 00/17203
Patent Document 4: WO 01/19829

Non-Patent Documents

Non-Patent Document 1: Proc. Natl. Acad. Sci. U.S.A., 100 Suppl. 1, 11842-11849 (2003)
Non-Patent Document 2: Nat. Immunol., 5, 738-743 (2004)
Non-Patent Document 3: Oncogene, 23, 7178-7187 (2004)
Non-Patent Document 4: Nature Biotechnology, 25, 1315-1321 (2007)
Non-Patent Document 5: Nature Biotechnology, 28, 275-280 (2010)
Non-Patent Document 6: Science Translational Medicine, 2, 17ra9 (2010)

SUMMARY OF THE INVENTION

Object to be Attained by the Invention

It is an object of the present invention to provide a pharmaceutical composition that has effects of inhibiting the growth of leukemia stem cells and is effective for treatment or inhibition of recurrence of acute myeloid leukemia.

Means for Attaining the Object

The present inventors paid particular attention to hemopoietic cell kinase (HCK) as an intracellular signaling factor among LSC-specific genes, and they conducted concentrated studies on cytotoxic activities of compounds included in 5,7-disubstituted-7H-pyrrolo[2,3-d]pyrimidin-4-amine described in Patent Document 3 and 5,7-disubstituted-7H-pyrazolo[3,4-d]pyrimidin-4-amine described in Patent Document 4 against LSCs with the use of, for example, mouse models of acute myeloid leukemia (AML). As a result, they discovered that some compounds included in 5,7-disubstituted-7H-pyrrolo[2,3-d]pyrimidin-4-amine have remarkable effects of killing LSCs and therapeutic effects on AML and that some other compounds do not exert therapeutic effects on AML, even in spite of having very similar structures. They also discovered that a substance exerting enzyme inhibitory effects on FLT3 (i.e., fms-related tyrosine kinase 3) in addition to enzyme inhibitory effects on HCK would exert remarkable effects of killing LSCs.

In addition, the present inventors discovered that some of the aforementioned compounds would have remarkable effects of killing leukemia stem cells with Flt3/ITD mutations if such compounds had enzyme inhibitory effects on a mutant FLT3 gene (Flt3/ITD mutations; Flt3$^-$ITD$^+$, ITD: internal tandem duplication) in a region in the vicinity of a membrane encoding a site immediately downstream of the transmembrane region. This has led to the completion of the present invention.

Specifically, the present invention is summarized as follows.

(1) A compound represented by formula (I), a salt thereof, or a prodrug thereof:

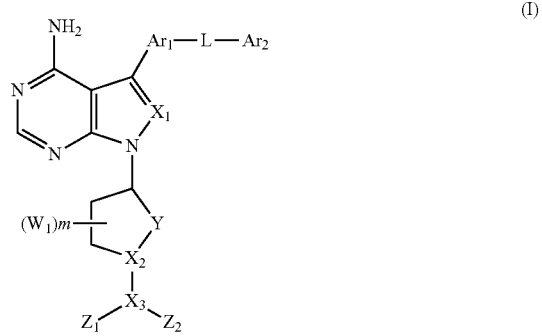

wherein
  $Ar_1$ represents a substituted or unsubstituted arylene or heteroarylene group;
  $Ar_2$ represents a substituted or unsubstituted aryl or heteroaryl group;
  L represents an oxygen atom, a sulfur atom, —NH—, —NHCO—, or —CONH—;
  $X_1$ represents CH or a nitrogen atom;
  $X_2$ and $X_3$ each independently represent CH or a nitrogen atom, provided that $X_2$ and $X_3$ are not the same;
  Y represents a $C_{1-3}$-alkylene group;
  $W_1$, which is a substituent on the ring including Y and $X_2$, each independently represent a $C_{1-6}$-alkyl group;
  m is an integer from 0 to 3; and
  $Z_1$ and $Z_2$ each independently represent a hydrogen atom, a $C_{1-6}$-alkyl group, an amino-$C_{1-6}$-alkyl group, a $C_{1-6}$-alkylamino-$C_{1-6}$-alkyl group, a di($C_{1-6}$-alkyl)amino-$C_{1-6}$-alkyl group, a hydroxy-$C_{1-6}$-alkyl group, a $C_{1-6}$-alkoxy-$C_{1-6}$-alkyl group, a $C_{2-7}$-aliphatic acyl group, a carboxy-$C_{1-6}$-alkyl group, a carbamoyl-$C_{1-6}$-alkyl group, a substituted or unsubstituted saturated heterocyclic group, a substituted or unsubstituted aryl-$C_{1-6}$-alkyl group, a substituted or unsubstituted heteroaryl-$C_{1-6}$-alkyl group, a substituted or unsubstituted arylcarbonyl group, or a substituted or unsubstituted heteroarylcarbonyl group, excluding the case in which both $Z_1$ and $Z_2$ represent hydrogen atoms;
  when $X_2$ represents CH and $X_3$ represents a nitrogen atom, $Z_1$ and $Z_2$ may form a substituted or unsubstituted, monocyclic or polycyclic heterocyclic group including $X_3$ and containing as a ring member two or more hetero atoms selected from the group consisting of oxygen, sulfur, and nitrogen atoms, or
  when $X_2$ represents a nitrogen atom and $X_3$ represents CH, $Z_1$ and $Z_2$ may form a substituted or unsubstituted, monocyclic or polycyclic heterocyclic group including $X_3$ and containing a hetero atom selected from among oxygen, sulfur, and nitrogen atoms.

(2) The compound according to (1), a salt thereof, or a prodrug thereof, wherein $Ar_1$ represents a substituted or unsubstituted arylene group, $Ar_2$ represents a substituted or unsubstituted aryl group, and L represents an oxygen atom.

(3) A pharmaceutical composition for killing leukemia stem cells, which comprises the compound according to (1) or (2), a salt thereof, or a prodrug thereof.

(4) A pharmaceutical composition for treatment or inhibition of recurrence of acute myeloid leukemia, which comprises the compound according to (1) or (2), a salt thereof, or a prodrug thereof.

(5) A pharmaceutical composition for treatment of recurrent acute myeloid leukemia, which comprises the compound according to (1) or (2), a salt thereof, or a prodrug thereof.

(6) A pharmaceutical composition comprising the compound according to (2), a salt thereof, or a prodrug thereof, which is intended to affect leukemia stem cells having Flt3/ITD mutation.

(7) The pharmaceutical composition according to (6), which is administered to a patient with acute myeloid leukemia in which leukemia stem cells with Flt3/ITD mutation are present.

(8) The pharmaceutical composition according to any of (3) to (7), wherein $X_2$ represents CH, $X_3$ represents a nitrogen atom, and $Z_1$ and $Z_2$ form a substituted or unsubstituted, monocyclic or polycyclic heterocyclic group including $X_3$ and containing as a ring member two or more hetero atoms selected from the group consisting of oxygen, sulfur, and nitrogen atoms.

(9) The pharmaceutical composition according to (8) for treatment of recurrent acute myeloid leukemia, wherein the compound is 7-[trans-4-(4-methyl-1-piperazinyl)cyclohexyl]-5-(4-phenoxyphenyl)-7H-pyrrolo[2,3-d]pyrimidin-4-amine.

(10) The pharmaceutical composition according to any of (3) to (7), wherein $Z_1$ represents a hydrogen atom and $Z_2$ represents a substituted or unsubstituted saturated heterocyclic group, a substituted or unsubstituted heteroaryl-$C_{1-6}$-alkyl group, or a substituted or unsubstituted heteroarylcarbonyl group.

(11) The pharmaceutical composition according to any of (3) to (7), wherein $X_2$ represents a nitrogen atom, $X_3$ represents CH, and $Z_1$ and $Z_2$ form a substituted or unsubstituted, monocyclic or polycyclic heterocyclic group including $X_3$ and containing a hetero atom selected from among oxygen, sulfur, and nitrogen atoms.

(12) The pharmaceutical composition according to (4), wherein $Ar_1$ represents a substituted or unsubstituted arylene group, $Ar_2$ represents a substituted or unsubstituted heteroaryl group, and L represents —NHCO—.

(13) The pharmaceutical composition according to (12), which further comprises an agent exerting inhibitory effects on FLT3.

(14) The pharmaceutical composition according to (13), wherein the agent is at least one agent selected from Crenolanib, Lestautirinib, PKC412/CGP41251, Tandutinib, Sunitinib, Sorafenib, Linifanib, Dovitinib, KW-2449, Quizartinib, Dovitinib Dilactic acid, Tandutinib, Cabozanitib, TG101209, Amuvatinib, and ENMD-2076.

(15) A pharmaceutical composition for killing leukemia stem cells, which comprises a nucleic acid that inhibits HCK gene expression and a nucleic acid that inhibits Flt3 gene expression.

(16) The pharmaceutical composition according to (15), wherein the nucleic acid that inhibits gene expression is siRNA.

(17) The pharmaceutical composition according to (15) or (16), wherein Flt3/ITD mutations are present in the leukemia stem cells.

(18) A method for killing leukemia stem cells comprising a step of administering the pharmaceutical composition according to any of (3) to (17) to an individual in which leukemia stem cells are present.

(19) The method according to (18), wherein the individual in which leukemia stem cells are present has recurrent acute myeloid leukemia.

(20) The method according to (18) or (19), wherein Flt3/ITD mutations are present in the leukemia stem cells.

(21) A method for screening for a compound having both effects of inhibiting HCK activity and effects of inhibiting Flt3 using a function of killing leukemia stem cells in which Flt3/ITD mutations are present as an indicator.

(22) A method for determining improved pharmacological efficacy of treatment conducted with the use of the pharmaceutical composition according to any of (3) to (17) on an individual who has been diagnosed as having acute myeloid leukemia and has leukemia stem cells in which Flt3/ITD mutations are present comprising steps of:
  obtaining a nucleic acid from a tumor cell sample of acute myeloid leukemia in an individual; and
  detecting an ITD mutation in the Flt3 gene in the nucleic acid,
  wherein the presence of the ITD mutation indicates the improved pharmacological efficacy of the treatment conducted with the use of the pharmaceutical composition according to any of (3) to (17) on an individual.

Effects of the Invention

The present invention can provide a pharmaceutical composition having effects of inhibiting the growth of leukemia stem cells or a function of killing leukemia stem cells, which is effective for treatment or inhibition of recurrence of acute myeloid leukemia.

BRIEF DESCRIPTION OF THE INVENTION

EMBODIMENTS FOR CARRYING OUT THE INVENTION

Figure 1:
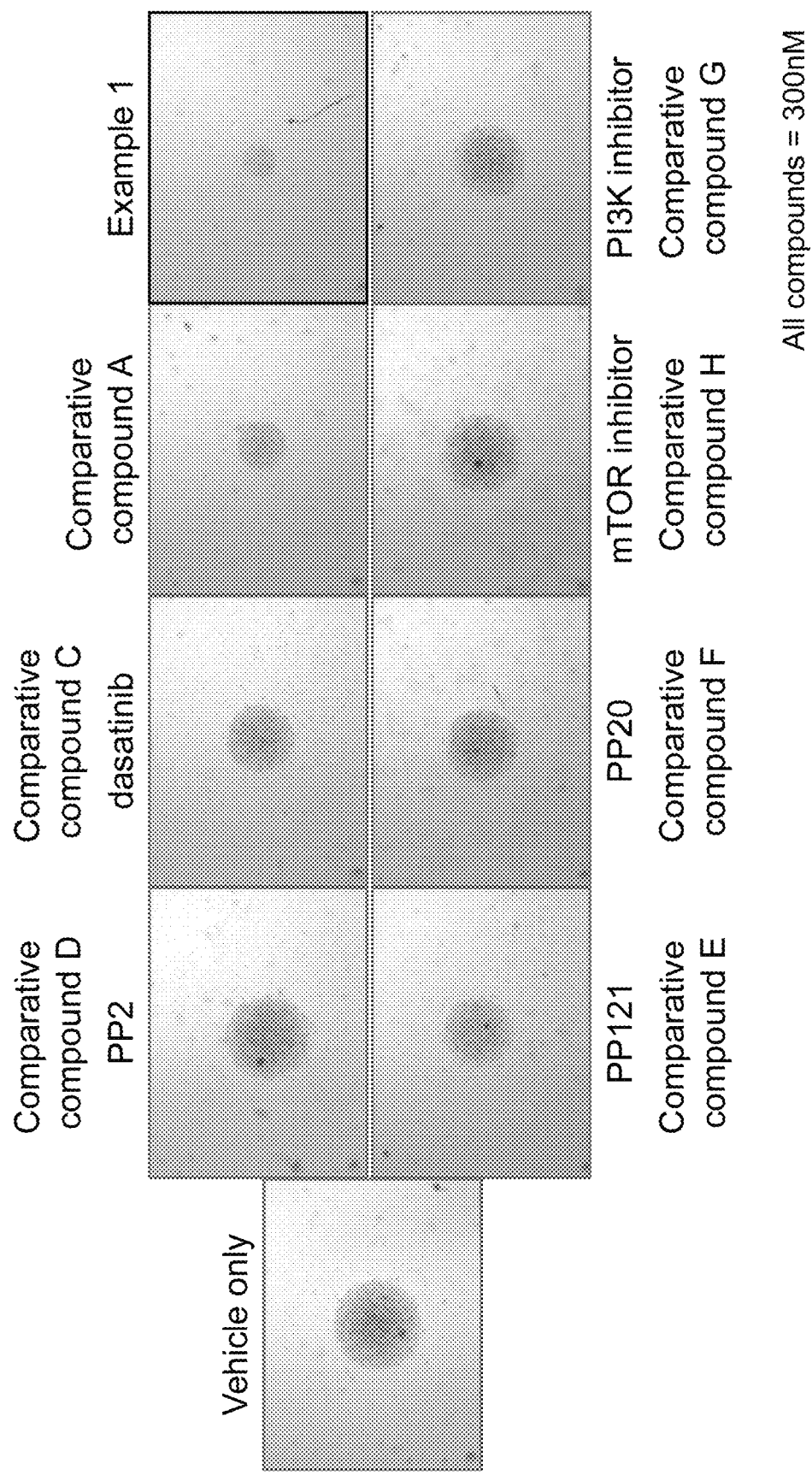
FIG. 1 shows the results of analysis of inhibitory effects of a test compound on the growth of human AML CD34$^+$CD38$^-$ cells.
Figure 2:
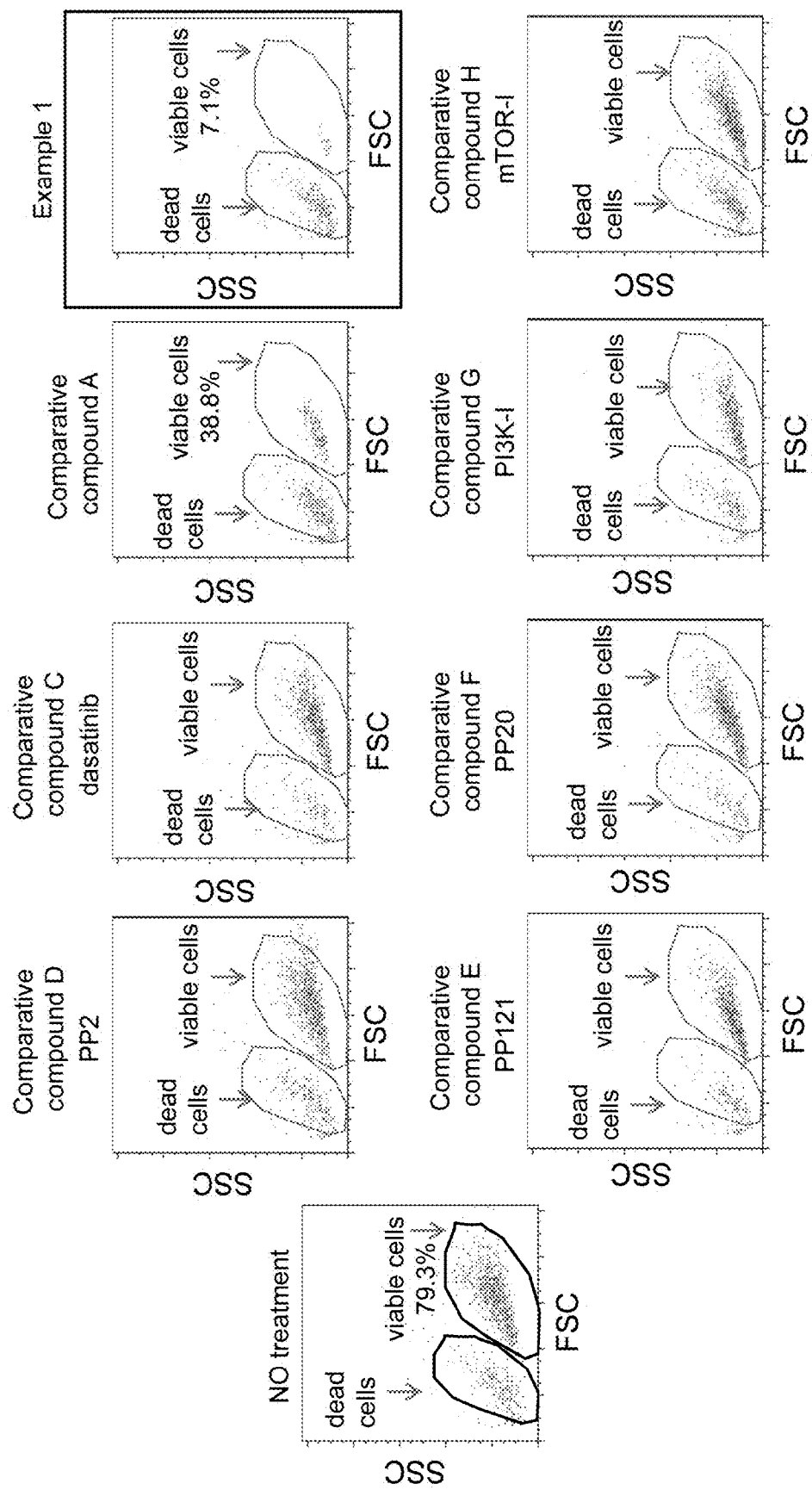
FIG. 2 shows the results of analysis of inhibitory effects of a test compound on the growth of human AML CD34$^+$CD38$^-$ cells.

Hereafter, the present invention is described in detail.

In the present invention, examples of arylene groups and heteroarylene groups include divalent groups generated by removing a hydrogen atom on a ring carbon atom from relevant aryl groups and heteroaryl groups described below.

Examples of aryl groups include phenyl and naphthyl groups.

Examples of heteroaryl groups include furyl, thienyl, pyrrolyl, oxazolyl, isoxazolyl, thiazolyl, isothiazolyl, imidazolyl, pyrazolyl, pyridyl, pyrimidinyl, pyridazinyl, pyrazinyl, quinolyl, isoquinolyl, and indolyl groups.

Examples of $C_{1-3}$-alkylene groups include methylene, ethylene, methylethylene, and trimethylene groups.

Examples of $C_{1-6}$-alkyl groups include: chain alkyl groups, such as methyl, ethyl, propyl, isopropyl, butyl, isobutyl, sec-butyl, tert-butyl, pentyl, isopentyl, and hexyl groups; and cyclic alkyl groups, such as cyclopropyl, cyclobutyl, cyclopentyl, and cyclohexyl groups.

Examples of $C_{2-7}$-aliphatic acyl groups include acetyl, propionyl, butylyl, isobutylyl, and valeryl groups.

Examples of saturated heterocyclic groups include tetrahydropyranyl, piperidinyl, and pyrrolidinyl groups.

Examples of monocyclic, heterocyclic groups formed by $Z_1$ and $Z_2$ include pyrrolidinyl, piperidinyl, and piperazinyl groups. Examples of polycyclic, heterocyclic groups include pyrazolopyrazinyl and triazolopyrazinyl groups.

Examples of substituents on $Ar_1$ or $Ar_2$ include: $C_{1-6}$-alkyl groups; $C_{2-6}$-alkenyl groups such as vinyl and allyl groups; $C_{2-6}$-alkynyl groups such as ethynyl and propargyl groups; $C_{2-6}$-alkylene groups; aryl groups; heteroaryl groups; $C_{2-7}$-aliphatic acyl groups such as acetyl and propionyl groups; aromatic acyl groups such as benzoyl groups; hydroxyl groups; carbonyl groups; carboxyl groups; cyano group; halogen atoms (i.e., fluorine, chlorine, bromine, and iodine atoms); $C_{1-6}$-alkoxy groups such as methoxy, ethoxy, propoxy, and isopropyloxy groups; aralkyl groups such as benzyl groups; aralkyloxy groups such as benzyloxy groups; nitro groups; amino groups; $C_{1-6}$-alkylamino groups; and di($C_{1-6}$-alkyl)amino groups. The $Ar_1$ or $Ar_2$ group may be substituted with a plurality of independent substituents.

Examples of substituents on aryl-$C_{1-6}$-alkyl groups, heteroaryl-$C_{1-6}$-alkyl groups, arylcarbonyl groups, or heteroarylcarbonyl groups represented by $Z_1$ or $Z_2$ include $C_{1-6}$-alkyl groups, $C_{1-6}$-alkoxy groups, halogen atoms, and carboxyl groups.

Examples of substituents on saturated heterocyclic groups represented by $Z_1$ or $Z_2$ include $C_{1-3}$-alkyl groups, $C_{1-3}$-alkylene groups, carbonyl groups (oxo groups), and carboxyl groups.

Examples of substituents on monocyclic or polycyclic heterocyclic groups formed by $Z_1$, $Z_2$, and $X_2$ include $C_{1-6}$-alkyl groups, $C_{2-6}$-alkenyl groups, $C_{2-6}$-alkynyl groups, $C_{1-3}$-alkylene groups, aryl groups, heteroaryl groups, $C_{2-7}$-aliphatic acyl groups, hydroxyl groups, carboxyl groups, cyano groups, $C_{1-6}$-alkoxy groups, hydroxy-$C_{1-6}$-alkyl groups, $C_{1-6}$-alkoxy-$C_{1-6}$-alkyl groups, aralkyl groups, aralkyloxy groups, nitro groups, amino groups, $C_{1-6}$-alkylamino groups, and di($C_{1-6}$-alkyl)amino groups. The heterocyclic group may be substituted with a plurality of independent substituents.

$Ar_1$ is preferably a 1,4-phenylene, 2-methoxy-1,4-phenylene, 3-methoxy-1,4-phenylene, or 2,5-pyridylene group.

$Ar_2$ is preferably a phenyl, fluorophenyl, pyridyl, or methylindolyl group, and it is more preferably a phenyl or 1-methyl-2-indolyl group.

L is preferably an oxygen atom, —NHCO—, or —CONH—, and it is more preferably an oxygen atom or —NHCO—.

Y is preferably a methylene or ethylene group, and it is more preferably an ethylene group.

$W_1$ is preferably a methyl group.

m is preferably 0.

$C_{1-6}$-alkyl represented by $Z_1$ or $Z_2$ is preferably chain alkyl, and it is more preferably methyl, ethyl, propyl, or isopropyl.

Amino-$C_{1-6}$-alkyl represented by $Z_1$ or $Z_2$ is preferably 2-aminoethyl, 3-aminopropyl, or 4-aminobutyl.

$C_{1-6}$-alkylamino-$C_{1-6}$-alkyl represented by $Z_1$ or $Z_2$ is preferably 2-(methylamino)ethyl, 2-(ethylamino)ethyl, 3-(methylamino)propyl, 3-(ethylamino)propyl, or 4-(methylamino)butyl.

Di($C_{1-6}$-alkyl)amino-$C_{1-6}$-alkyl represented by $Z_1$ or $Z_2$ is preferably 2-(dimethylamino)ethyl, 2-(diethylamino)ethyl, 3-(dimethylamino)propyl, 3-(diethylamino)propyl, or 4-(dimethylamino)butyl.

Hydroxy-$C_{1-6}$-alkyl represented by $Z_1$ or $Z_2$ is preferably 2-hydroxyethyl, 3-hydroxypropyl, or 4-hydroxybutyl.

$C_{1-6}$-alkoxy-$C_{1-6}$-alkyl represented by $Z_1$ or $Z_2$ is preferably 2-methoxyethyl, 2-ethoxyethyl, 3-methoxypropyl, 3-ethoxypropyl, or 4-methoxybutyl.

Carboxy-$C_{1-6}$-alkyl represented by $Z_1$ or $Z_2$ is preferably carboxymethyl, 2-carboxyethyl, 3-carboxypropyl, or 4-carboxybutyl.

Carbamoyl-$C_{1-6}$-alkyl represented by $Z_1$ or $Z_2$ is preferably carbamoylmethyl, 2-carbamoylethyl, 3-carbamoylpropyl, or 4-carbamoylbutyl.

A saturated heterocyclic group represented by $Z_1$ or $Z_2$ is preferably 4-piperidinyl, 4-tetrahydropyranyl, or 3-pyrrolidinyl.

Arylcarbonyl represented by $Z_1$ or $Z_2$ is preferably benzoyl.

Heteroarylcarbonyl represented by $Z_1$ or $Z_2$ is preferably pyridylcarbonyl.

Aryl-$C_{1-6}$-alkyl represented by $Z_1$ or $Z_2$ is preferably benzyl or phenylethyl.

Heteroaryl-$C_{1-6}$-alkyl represented by $Z_1$ or $Z_2$ is preferably pyridylmethyl, pyridylethyl, pyrazolylmethyl, pyrazolylethyl, imidazolylmethyl, or imidazolylethyl, and it is more preferably pyridylmethyl or pyrazolylmethyl.

A substituent on aryl-$C_{1-6}$-alkyl, heteroaryl-$C_{1-6}$-alkyl, arylcarbonyl, or heteroarylcarbonyl represented by $Z_1$ or $Z_2$ is preferably $C_{1-6}$-alkyl, $C_{1-6}$-alkoxy, or a halogen atom.

A substituent on a saturated heterocyclic group represented by $Z_1$ or $Z_2$ is preferably $C_{1-3}$-alkyl, $C_{1-3}$-alkylene, or carbonyl (oxo).

$Z_1$ is preferably a hydrogen atom or $C_{1-6}$-alkyl, and it is more preferably a hydrogen atom.

$Z_2$ is preferably carboxy-$C_{1-6}$-alkyl, carbamoyl-$C_{1-6}$-alkyl, substituted or unsubstituted aryl-$C_{1-6}$-alkyl, heteroaryl-$C_{1-6}$-alkyl, arylcarbonyl, heteroarylcarbonyl, or a saturated heterocyclic group, and it is more preferably carboxymethyl, carbamoylmethyl, pyrazolylmethyl, methylpyrazolylmethyl, pyridylmethyl, pyridylcarbonyl, tetrahydropyranyl, 8-azabicyclo[3.2.1]octan-3-yl, or 2-oxopyrrolidinyl, with carboxymethyl, carbamoylmethyl, pyrazolylmethyl, pyridylmethyl, pyridylcarbonyl, 4-tetrahydropyranyl, 8-azabicyclo[3.2.1]octan-3-yl, or 2-oxo-3-pyrrolidinyl being the most preferable.

When $X_2$ represents CH and $X_3$ represents a nitrogen atom, a heterocyclic group formed by $Z_1$, $Z_2$, and $X_3$ is preferably a piperazinyl group represented by formula (a):

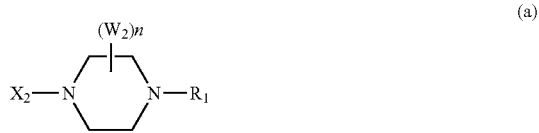

(a)

wherein $R_1$ represents a hydrogen atom, $C_{1-6}$-alkyl, $C_{2-7}$-aliphatic acyl, hydroxy-$C_{1-6}$-alkyl, or $C_{1-6}$-alkoxy-$C_{1-6}$-alkyl; $W_2$ represents $C_{1-6}$-alkyl or carbonyl; n is an integer from 0 to 3; $X_2$ is as defined above; and one or more groups represented by $W_2$ may together form $C_{1-3}$-alkylene; or it is preferably a condensed piperazinyl group represented by formula (b):

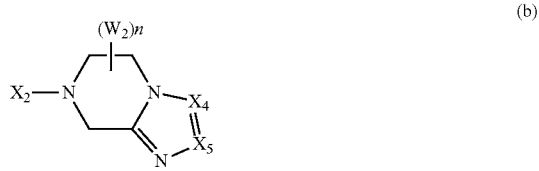

(b)

wherein $X_4$ and $X_5$ each independently represent $CR_2$ or a nitrogen atom; $X_2$, $W_2$, and n are as defined above; $R_2$ represents a hydrogen atom, $C_{1-6}$-alkyl, $C_{1-6}$-halogenated alkyl, or hydroxy-$C_{1-6}$-alkyl; and a plurality of groups represented by $R_2$ may differ from each other.

$R_1$ in a piperazinyl group represented by formula (a) is preferably a hydrogen atom, methyl, ethyl, propyl, isopropyl, butyl, isobutyl, sec-butyl, or tert-butyl.

A piperazinyl group represented by formula (a) is preferably piperazino, 4-methyl-1-piperazinyl, 4-tert-butyl-1-piperazinyl, 3,8-diazabicyclo[3.2.1]octan-3-yl, or 8-methyl-3,8-diazabicyclo[3.2.1]octan-3-yl.

$R_2$ in a condensed piperazinyl group represented by formula (b) is preferably a hydrogen atom, methyl, ethyl, or trifluoromethyl, and it is more preferably a hydrogen atom, methyl, or trifluoromethyl.

A condensed piperazinyl group represented by formula (b) is preferably imidazopyrazinyl, methylimidazopyrazinyl, triazolopyrazinyl, or methyltriazolopyrazinyl.

When $X_2$ represents a nitrogen atom and $X_3$ represents CH, a heterocyclic group formed by $Z_1$, $Z_2$, and $X_3$ is preferably a group derived from a piperazinyl group represented by formula (a) or a condensed piperazinyl group represented by formula (b) by substitution of a nitrogen atom that binds to $X_2$ with CH, and it is particularly preferably piperidin-4-yl or 8-azabicyclo[3.2.1]octan-3-yl.

A salt of a compound represented by formula (I) is preferably a pharmaceutically acceptable salt. Examples thereof include: salts of inorganic acids, such as hydrochloric acid, sulfuric acid, phosphoric acid, hydrobromic acid, hydroiodic acid, nitric acid, pyrosulfuric acid, and metaphosphoric acid; and salts of organic acids, such as citric acid, benzoic acid, acetic acid, propionic acid, fumaric acid, maleic acid, tartaric acid, succinic acid, sulfonic acids (e.g., methanesulfonic acid, p-toluenesulfonic acid, and naphthalenesulfonic acid), and amino acids (e.g., glutamic acid). When a compound represented by formula (I) has an acidic substituent, such as a phenolic hydroxyl group or a carboxyl group, alkali metal salts, such as sodium salt and potassium salts, lysine salts, or arginine salts, can also be used.

The term "prodrug" used herein refers to any compound that generates a compound represented by formula (I) as a result of spontaneous chemical reaction, enzymatic reaction caused by a catalyst, or metabolic reaction upon administration of such compound to an organism. Examples of groups constituting prodrugs for hydroxyl or amino groups include $C_{2-7}$-acyl, $C_{1-6}$-alkoxy($C_{2-7}$acyl), $C_{1-6}$-alkoxycarbonyl($C_{2-7}$-acyl), $C_{1-6}$-alkoxycarbonyl, $C_{1-6}$-alkoxy($C_{2-7}$-alkoxycarbonyl), ($C_{2-7}$-acyloxy)methyl, 1-($C_{2-7}$-acyloxy)ethyl, ($C_{2-7}$-alkoxycarbonyl)oxymethyl, and 1-[($C_{2-7}$-alkoxycarbonyl)oxy]ethyl, with $C_{2-7}$-acyl and $C_{1-6}$-alkoxycarbonyl being preferable. Examples of groups constituting prodrugs for carboxyl groups include $C_{1-6}$-alkyl, $C_{1-6}$-alkoxy-$C_{1-6}$-alkyl, ($C_{2-7}$-acyloxy)methyl, 1-($C_{2-7}$-acyloxy)ethyl, ($C_{2-7}$-alkoxycarbonyl)oxymethyl, and 1-[($C_{2-7}$-alkoxycarbonyl)oxy]ethyl, with $C_{1-6}$-alkyl and $C_{1-6}$-alkoxy-$C_{1-6}$-alkyl being preferable.

A compound represented by formula (I) can be produced in accordance with Patent Document 3 or Patent Document 4, for example, in the following manner. When a reactive substituent is present, a protective group may be added or eliminated before or after the reaction, according to need.

A compound represented by formula (I), wherein $X_1$ represents CH, can be produced by subjecting a compound represented by formula (II):

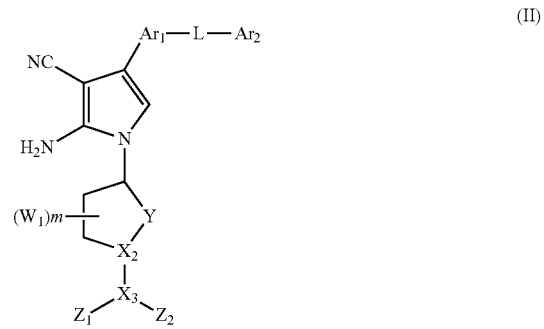

(II)

wherein $Ar_1$, $Ar_2$, L, $W_1$, $X_2$, $X_3$, Y, $Z_1$, $Z_2$, and m are as defined above, to a condensation reaction with formamide at 50° C. to 250° C. in the presence of a catalyst such as 4-dimethylaminopyridine, according to need.

A compound represented by formula (I) can be produced by subjecting a compound represented by formula (III):

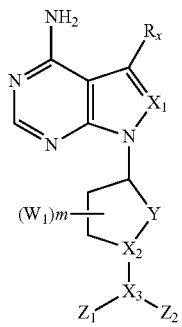

(III)

wherein $W_1$, $X_1$, $X_2$, $X_3$, Y, $Z_1$, and $Z_2$ are as defined above, and Rx represents a bromine atom or an iodine atom, to a reaction with a compound represented by formula (IVa), (IVb), or (IVc):

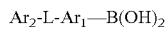 (IVa),

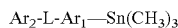 (IVb), or

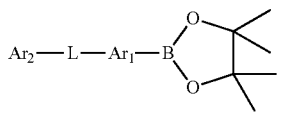 (IVc)

wherein $Ar_1$, $Ar_2$, and L are as defined above, in the presence of a catalyst, such as palladium (O) or Pd(PPh$_3$)$_4$.

A compound represented by formula (I) can be produced by subjecting a compound represented by formula (V):

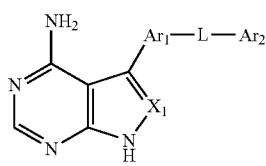 (V)

wherein $Ar_1$, $Ar_2$, L, and $X_1$ are as defined above, to alkylation by a compound represented by formula (VI):

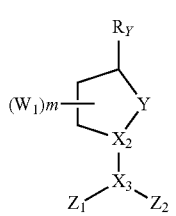 (VI)

wherein $W_1$, $X_2$, $X_3$, Y, $Z_1$, and $Z_2$ are as defined above, and $R_Y$ represents an eliminating group, such as a halogen atom, mesyloxy group, or tosyloxy group, or to the Mitsunobu reaction with a compound represented by formula (VII):

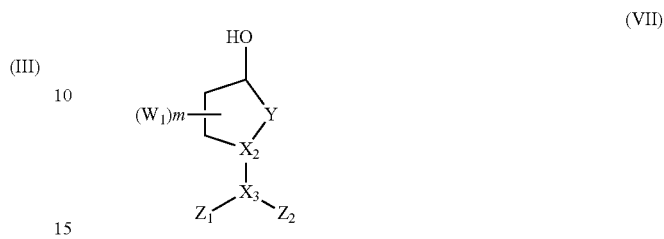 (VII)

wherein $W_1$, $X_2$, $X_3$, Y, $Z_1$, and $Z_2$ are as defined above.

A compound represented by formula (I) wherein $X_1$ and $X_2$ each represent CH can be produced by subjecting a compound represented by formula (III):

 (VIII)

to the Mitsunobu reaction with a compound represented by formula (IX):

 (IX)

wherein Y is as defined above, subjecting the resulting compound represented by formula (X):

 (X)

wherein $W_1$ and m are as defined above, to a reaction with a compound represented by formula (IVa), (IVb), or (IVc) in the presence of a catalyst, such as palladium (O) or Pd(PPh$_3$)$_4$, eliminating a protective group from the resulting compound represented by formula (XI):

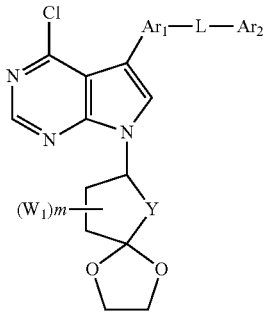

(XI)

wherein $Ar_1$, $Ar_2$, L, $W_1$, Y, and m are as defined above, to prepare a compound represented by formula (XII):

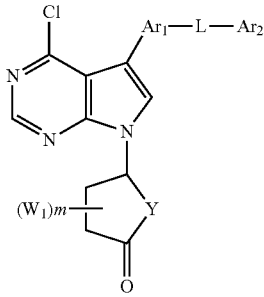

(XII)

wherein $Ar_1$, $Ar_2$, L, $W_1$, Y, and m are as defined above, and subjecting the resultant to a reaction with a compound represented by formula (XIII):

$Z_1$—NH—$Z_2$ wherein $Z_1$, and $Z_2$ are as defined above.

Products obtained in the manner described above may be purified via a conventional technique, such as column chromatography using silica gel as a carrier or recrystallization using methanol, ethanol, chloroform, dimethylsulfoxide, water, or the like. Examples of elution solvents used for column chromatography include methanol, ethanol, chloroform, acetone, hexane, dichloromethane, ethyl acetate, and a mixture of any thereof.

(Pharmaceutical Composition)

A compound represented by formula (I), a salt thereof, or a prodrug thereof (hereafter, referred to as "compound (I)") has effects of inhibiting the growth of leukemia stem cells or a function of killing leukemia stem cells. Thus, such compound, a salt thereof, or a prodrug thereof can be used for a pharmaceutical composition for treatment or inhibition of recurrence of acute myeloid leukemia.

Leukemia stem cells refer to cells that meet at least one of the following requirements:

1: they are cells capable of selectively and exclusively developing leukemia in vivo;

2: they are cells capable of generating a leukemia non-stem cell fraction that cannot spontaneously develop leukemia;

3: they are cells capable of engraftment in vivo; and/or

4: they are cells capable of self-reproduction.

According to an embodiment, leukemia stem cells show characteristics of $CD34^+CD38^-$ cells as surface antigens. In this description, leukemia stem cells obtained from a patient with acute myeloid leukemia are also referred to as "human AML $CD34^+CD38^-$ cells."

When a cell is capable of self-reproduction, such cell is capable of dividing into two cells; that is, a stem cell and a more differentiated precursor cell. The concept of leukemia stem cells has already been established and is commonly accepted in the art (D. Bonnet, J. E. Dick, Nat. Med., 3, 730 (1997); T. Lapidot et al., Nature, 367, 645 (1994)).

In this description, all types of leukemia stem cells are within the scope of "leukemia stem cells." The term "leukemia stem cells" preferably refers to stem cells in which the HCK gene expression level is high, and it more preferably refers to stem cells of acute myeloid leukemia cells.

The target leukemia stem cells in the present invention are generally derived from mammals. Examples of mammals include: laboratory animals, such as mice, rats, hamsters, guinea pigs, and other rodents, and rabbits; domestic animals, such as swine, cattle, goats, horses, sheep, and minks; companion animals, such as dogs and cats; and primates, such as humans, monkeys, cynomolgus monkeys, rhesus monkeys, marmosets, orangutans, and chimpanzees. The target leukemia stem cells in the present invention are preferably derived from primates, such as humans, or rodents, such as mice.

The pharmaceutical composition for killing leukemia stem cells and the pharmaceutical composition for treatment or inhibition of recurrence of acute myeloid leukemia according to the present invention (hereafter, "the pharmaceutical composition(s) of the present invention") have effects of killing leukemia stem cells. The effects of killing leukemia stem cells can be confirmed as the effects of inhibiting the growth of leukemia stem cells throughout the entire cell population.

Since leukemia stem cells are considered to cause recurrent leukemia, recurrence of leukemia can be inhibited and prevented with the use of the pharmaceutical composition of the present invention. Specifically, the pharmaceutical composition of the present invention is also useful as an agent for suppressing leukemia (preferably as an agent for inhibiting recurrence of leukemia). Recurrence of leukemia is a condition in which leukemic cells grow again after a patient has achieved partial or complete remission of leukemic symptoms through treatment and leukemic symptoms reappear or worsen. Through administration of the pharmaceutical composition of the present invention to a mammal at a risk of developing (or experiencing recurrence of) leukemia, development (or recurrence) of leukemia can be inhibited and prevented.

Acute myeloid leukemia can be brought into complete remission with the use of known chemotherapeutic agents for cancer, such as alkylating agents (e.g., cyclophosphamide and ifosfamide), antimetabolites (e.g., cytarabine, 5-fluorouracil, and methotrexate), antitumor antibiotics (e.g., adriamycin and mitomycin), plant-derived anticancer agents (e.g., vinblastine, vincristine, vindesine, and Taxol), cisplatin, carboplatin, or etoposide. However, AML often recurs after complete remission has been achieved, and for many patients, recurrent AML results in death.

Through administration of the pharmaceutical composition of the present invention to a patient who had achieved complete remission of acute myeloid leukemia, recurrence of acute myeloid leukemia can be prevented.

A compound represented by formula (I) wherein $Ar_1$ represents substituted or unsubstituted arylene, $Ar_2$ represents substituted or unsubstituted aryl, and L represents an oxygen atom exerts remarkable inhibitory effects on HCK and FLT3 and high inhibitory effects on FLT3/ITD mutations. Accordingly, the pharmaceutical composition of the present invention containing the compound, a salt thereof, or a prodrug thereof exerts a sufficiently significant function of killing leukemia stem cells. The pharmaceutical composition of the present invention containing the compound, a salt thereof, or a prodrug thereof has a particularly remarkable function of killing leukemia stem cells with FLT3/ITD mutations. Accordingly, the pharmaceutical composition of the present invention exerts particularly high therapeutic effects on recurrent acute myeloid leukemia caused by leukemia stem cells that had become malignant as a result of FLT3/ITD mutations.

The pharmaceutical composition of the present invention can further contain an agent exerting inhibitory effects on FLT3, in addition to a compound represented by formula (I), a salt thereof, or a prodrug thereof. Thus, the function of killing leukemia stem cells with Flt3/ITD mutations can be enhanced.

Examples of agents having inhibitory effects on FLT3 used in the present invention include, but are not limited to, Crenolanib, Lestautirinib (CEP-701/KT5555), PKC412 (CGP41251), Tandutinib (MLN518/CT53518), Sunitinib (SU11248), Sorafenib (BA43-9006), Linifanib (ABT-869), Dovitinib (CHIR-258/TKI-258), KW-2449, Quizartinib (AC220), Dovitinib Dilactic acid, Cabozanitib (XL-184), R406, TG101209, Amuvatinib, and ENMD-2076.

ITD mutations in FLT3 can be detected and evaluated by detecting differences from normal types at the site of mutation by PCR, electrophoresis, sequencing, detection with antibodies (e.g., Western blotting or ELISA), or other means, according to need. It can be evaluated that pharmacological efficacy is enhanced in individuals in which ITD mutations in FLT3 are detected in leukemia stem cells compared with individuals in which normal FLT3 is detected in leukemia stem cells. When pharmacological efficacy is evaluated as being enhanced, the pharmaceutical composition of the present invention is administered to the individual. Thus, treatment and/or prevention of recurrence of acute myeloid leukemia can be achieved.

(Nucleic Acid that Inhibits HCK Expression or Function)

Nucleotide sequences and amino acid sequences of HCK and FLT3 are known. Representative nucleotide sequences and amino acid sequences of human HCK are registered with, for example, NCBI under the accession numbers indicated below.

HCK nucleotide sequence (cDNA sequence): Accession Number: NM_002110.3 <<http://www.ncbi.nlm.nih.gov/nuccore/NM_002110.3>>

HCK amino acid sequence: Accession Number: NP_002101.2 <<http://www.ncbi.nlm.nih.gov/protein/NP_002101.2>>

FLT3 nucleotide sequence (cDNA sequence): Accession Number: NM_004119.2 <<http://www.ncbi.nlm.nih.gov/nuccore/NM_004119.2>>

FLT3 amino acid sequence: Accession Number: NP_004110.2 <<http://www.ncbi.nlm.nih.gov/protein/NP_004110.2>>

Examples of nucleic acids that inhibit HCK expression or functions include a siRNA and an antisense nucleic acid capable of specifically inhibiting HCK expression, and an expression vector and a low-molecular-weight compound capable of expressing polynucleotides thereof. Use of siRNA or an antisense nucleic acid capable of specifically inhibiting HCK expression, or an expression vector capable of expressing polynucleotides thereof is preferable.

When gene expression is specifically inhibited, in the present description, the degree of target gene expression to be inhibited is higher than that of other genes.

Examples of siRNA capable of specifically inhibiting HCK expression include the following:

(A) double-stranded RNA comprising a nucleotide sequence of mRNA encoding HCK (mature mRNA or an initial transcription product) or a nucleotide sequence complementary to a partial sequence thereof of 18 or more nucleotides; and (B) double-stranded RNA comprising a nucleotide sequence of 18 or more nucleotides capable of hybridizing specifically to mRNA encoding HCK (mature mRNA or an initial transcription product) in a cell of a target animal (preferably a human) and inhibiting HCK transcription as a result of hybridization.

The term "specific hybridization" and variations thereof used herein refer to a situation in which the degree of hybridization of a nucleic acid to a target nucleotide is higher than that to other nucleotides.

An example of a nucleotide sequence encoding HCK is the nucleotide sequence indicated by NCBI Accession Number NM_002110.3 (human HCK).

A phenomenon that is referred to as RNA interference (RNAi); that is, introduction of short double-stranded RNA into a cell resulting in decomposition of mRNA complementary to the RNA, has heretofore been known to occur in cells of nematodes, insects, plants, and other organisms. Since such phenomenon was found to occur in animal cells in recent years (Nature, 411 (6836): 494-498 (2001)), it has drawn attention as an alternative technique of ribozyme.

Typical siRNA is double-stranded oligo RNA comprising RNA having a sequence complementary to the mRNA nucleotide sequence of a target gene or a partial sequence thereof (hereafter, referred to as a "target nucleotide sequence") and a strand complementary thereto. According to another preferable embodiment, siRNA is single-stranded RNA comprising a sequence complementary to the target nucleotide sequence (the first sequence) and a sequence complementary thereto (the second sequence) ligated to each other to form a hairpin loop, and a double-stranded construct is thus formed by the first sequence and the second sequence (i.e., small hairpin RNA (shRNA)).

A fragment of siRNA complementary to the target nucleotide sequence generally comprises about 18 or more nucleotides, preferably about 19 or more nucleotides, and more preferably about 21 or more nucleotides. Fragment size is not particularly limited, provided that the fragment is capable of specifically inhibiting the expression of the target gene. When siRNA comprises more than 23 nucleotides, such siRNA is decomposed in a cell, and siRNA comprising about 20 nucleotides is then generated. In theory, accordingly, the maximal size of a fragment complementary to the target nucleotide sequence is that of a full-length nucleotide sequence of mRNA of the target gene (mature mRNA or an initial transcription product). From the viewpoint of prevention of interferon induction, ease of synthesis, and antigenicity, however, such complementary fragment comprises, for example, about 50 or fewer nucleotides, preferably about 25 or fewer nucleotides, and most preferably about 23 or fewer nucleotides. That is, the complementary fragment generally comprises about 18 to 50 nucleotides, preferably about 19 to 25 nucleotides, and more preferably about 21 to 23 nucleotides.

Each RNA strand constituting siRNA generally comprises about 18 or more nucleotides, preferably about 19 or more nucleotides, and more preferably about 21 or more nucleotides. Such length is not particularly limited, provided that it is capable of specifically inhibiting the expression of the target gene. In theory, accordingly, there is no upper limit for RNA strand length. From the viewpoint of prevention of interferon induction, ease of synthesis, and antigenicity, however, siRNA comprises, for example, about 50 or fewer nucleotides, preferably about 25 or fewer nucleotides, and most preferably about 23 or fewer nucleotides. For example, an RNA strand generally comprises about 18 to 50 nucleotides, preferably about 19 to 25 nucleotides, and more preferably about 21 to 23 nucleotides. It should be noted that the shRNA length is the length of a double-stranded portion when a double-stranded structure is formed.

It is preferable that the target nucleotide sequence and the sequence complementary thereto contained in the siRNA be completely complementary to each other. In the presence of a nucleotide mutation at a position apart from the center of the siRNA (it can fall within the range of identity of at least 90% or more, and preferably 95% or more), however, the cleavage activity by RNA interference is not completely lost, and partial activity can remain. On the other hand, a nucleotide mutation in the center of the siRNA has a major influence to an extent that can extremely reduce mRNA cleavage activity by RNA interference.

siRNA may comprise an additional nucleotide sequence that does not form a base pair at the 5' and/or 3' end. The length of the additional nucleotide sequence is not particularly limited, provided that siRNA is capable of specifically inhibiting the expression of the target gene, and it is generally 5 or fewer (e.g., 2 to 4) nucleotides. While the additional nucleotide sequence may be a DNA or RNA, stability of siRNA can be improved with the use of DNA. Examples of additional nucleotide sequences include, but are not limited to, ug-3', uu-3', tg-3', tt-3', ggg-3', guuu-3', gttt-3', ttttt-3', and uuuuu-3'.

The length of a loop portion of an shRNA hairpin loop is not particularly limited, provided that the expression of the target gene can be specifically inhibited. In general, such loop portion comprises about 5 to 25 nucleotides. A nucleotide sequence of the loop portion is not particularly limited, provided that a loop can be formed and the shRNA can specifically inhibit the expression of the target gene.

The "antisense nucleic acid" comprises a nucleotide sequence capable of hybridizing specifically to target mRNA (mature mRNA or an initial transcription product) in a cell that expresses the target mRNA under physiological conditions, and it is capable of inhibiting translation of a polypeptide encoded by the target mRNA in the hybridized state. The antisense nucleic acid may be a DNA or RNA, and it may be a DNA/RNA chimera, with DNA being preferable.

Examples of antisense nucleic acids capable of specifically inhibiting HCK expression include the following:

(A) a nucleic acid comprising a nucleotide sequence of mRNA encoding HCK (mature mRNA or an initial transcription product) or a nucleotide sequence complementary to a partial sequence thereof comprising 12 or more nucleotides; and (B) a nucleic acid comprising a nucleotide sequence of 12 or more nucleotides capable of hybridizing specifically to mRNA encoding HCK (mature mRNA or an initial transcription product) in a cell of a target animal (preferably a human) and capable of inhibiting translation into an HCK polypeptide in the hybridized state.

The length of a portion of the antisense nucleic acid hybridizing to target mRNA is not particularly limited, provided that HCK expression is specifically inhibited. In general, such portion comprises about 12 or more nucleotides, and the longer portion is as long as the full-length sequence of mRNA (mature mRNA or an initial transcription product). From the viewpoint of hybridization specificity, the number of nucleotides is preferably about 15 or more, and more preferably about 18 or more. From the viewpoint of ease of synthesis and antigenicity, a portion hybridizing to target mRNA generally comprises about 200 or fewer nucleotides, preferably about 50 or fewer nucleotides, and more preferably about 30 or fewer nucleotides. That is, a portion hybridizing to target mRNA comprises, for example, about 12 to 200 nucleotides, preferably about 15 to 50 nucleotides, and more preferably about 18 to 30 nucleotides.

The target nucleotide sequence of the antisense nucleic acid is not particularly limited, provided that HCK expression can be specifically inhibited. It may be a full-length sequence of mRNA of HCK (mature mRNA or an initial transcription product), a partial sequence thereof (e.g., a fragment comprising about 12 or more nucleotides, preferably about 15 or more nucleotides, and more preferably about 18 or more nucleotides), or an intron portion of the initial transcription product. The target sequence is preferably located between the 5' terminus of mRNA of HCK and the C terminus of the coding region.

The nucleotide sequence of a portion of the antisense nucleic acid hybridizing to target mRNA generally has about 90% or higher (preferably 95% or higher, and most preferably 100%) sequence identity to a sequence complementary to the target sequence, so as to allow hybridization to mRNA of HCK under physiological conditions, although such nucleotide sequence varies depending on the nucleotide composition of the target sequence.

The antisense nucleic acid generally comprises about 12 or more nucleotides, preferably about 15 or more nucleotides, and more preferably about 18 nucleotide sequences. From the viewpoint of ease of synthesis and antigenicity, such antisense nucleic acid generally comprises 200 or fewer nucleotides, preferably about 50 or fewer nucleotides, and more preferably about 30 or fewer nucleotides.

The antisense nucleic acid hybridizes to mRNA or an initial transcription product of HCK to inhibit translation. In addition, the antisense nucleic acid may be capable of binding to the HCK gene, which is a double-stranded DNA, to form a triple strand (i.e., a triplex) and inhibiting transcription into mRNA.

A phosphodiester bond in a naturally occurring nucleic acid is easily decomposed by a nuclease existing in a cell. Accordingly, siRNA or the antisense nucleic acid used in the present invention may be synthesized with the use of a modified nucleotide, such as a thiophosphate nucleotide (P=O of a phosphoric acid bond is substituted with P=S) or 2'-O-methyl nucleotide that is stable against a nuclease. When designing siRNAs and antisense nucleic acids, it is also important to improve water solubility and cell membrane permeability. Such improvement can be realized by choosing appropriate dosage forms, such as those involving the use of liposomes or microspheres.

siRNA and an antisense nucleic acid capable of specifically inhibiting HCK expression can be prepared by determining the target sequence on the basis of the HCK nucleotide sequence (e.g., the nucleotide sequence under Accession Number NM_002110.3 of NCBI) or the chromosome DNA sequence and synthesizing a nucleotide sequence complementary thereto using a commercially available automated DNA/RNA synthesizer (e.g., Applied Biosystems, Beckman). siRNA can be prepared by synthesizing a sense strand separately from an antisense strand using automated DNA/RNA synthesizers, denaturing the strands in an adequate annealing buffer at about 90° C. to 95° C. for about 1 minute, and then conducting annealing at about 30° C. to 70° C. for about 1 to 8 hours. Also, complementary oligonucleotide strands are synthesized to alternately overlap each other, and the synthesized strands are subjected to annealing and then ligation with the aid of a ligase. Thus, a longer double-stranded polynucleotide can be prepared.

The pharmaceutical composition of the present invention can comprise, as an active ingredient, an expression vector capable of expressing (or encoding) siRNA or an antisense nucleic acid that specifically inhibits HCK expression. In such expression vector, siRNA, the antisense nucleic acid, or a nucleic acid (preferably DNA) encoding the same is operably linked to a promoter that can exert promoter activity in a cell (e.g., a sarcoma cell) of a recipient mammal (preferably a human).

Any promoter can be used without particular limitation, provided that it can function in a cell of a recipient mammal. Examples of promoters that can be used include polI promoter, polII promoter, and polIII promoter. Specifically, viral promoters, such as SV40-derived early promoter and Cytomegalovirus LTR promoter, constitutive protein gene promoters of mammals, such as β-actin gene promoter, and RNA promoters such as tRNA promoter can be used.

When the expression of siRNA is intended, use of a polIII promoter is preferable. Examples of polIII promoters include U6 promoter, H1 promoter, and tRNA promoter.

The expression vector preferably comprises a transcription termination signal (i.e., a terminator region) in a site downstream of the polynucleotide or a nucleic acid encoding the same. In addition, the expression vector can further comprise a selection marker gene (e.g., a gene that imparts resistivity to a drug, such as tetracyclin, ampicillin, or kanamycin or a gene that compensates for auxotrophic mutation) for selection of transformed cells.

The description concerning HCK above can be applied to siRNA and an antisense nucleic acid that can specifically inhibit FLT3 expression by replacing "HCK" with "FLT3."

In this description, siRNA that can specifically inhibit HCK expression is also referred to as "HCK siRNA," and siRNA that can specifically inhibit FLT3 expression is also referred to as "FLT3 siRNA."

(Dosage and Formulation of Compounds and Pharmaceutical Compositions)

Hereafter, the dosage and the formulation of the compound (I) and the pharmaceutical composition according to the present invention are described.

The compound (I) can be administered in an as-is state or together with common pharmaceutical carriers to humans and nonhuman animals. The dosage form is not particularly limited and it is adequately selected according to need. Examples of dosage forms include: oral preparations, such as tablets, capsules, granules, fine grains, powders, controlled-release formulations, suspensions, emulsions, syrups, and elixirs; and parenteral preparations, such as injection preparations, suppositories, liniments, and adhesive skin patches.

Oral preparations are produced in accordance with conventional techniques with the use of, for example, starch, lactose, saccharose, mannite, carboxymethylcellulose, cornstarch, or inorganic salts.

In addition to the excipients described above, oral preparations can comprise binders, disintegrators, surfactants, lubricants, flowability enhancers, flavors, colorants, or aroma chemicals.

Examples of binders include starch, dextrin, powdered acacia, gelatin, hydroxypropyl starch, methylcellulose, sodium carboxymethylcellulose, hydroxypropylcellulose, crystalline cellulose, ethylcellulose, polyvinylpyrrolidone, and Macrogol.

Examples of disintegrators include starch, hydroxypropyl starch, sodium carboxymethylcellulose, carboxymethylcellulose calcium, carboxymethylcellulose, and low-substituted hydroxypropylcellulose.

Examples of surfactants include sodium lauryl sulfate, soybean lecithin, sucrose fatty acid ester, and polysorbate 80.

Examples of lubricants include talc, waxes, hydrogenated vegetable oil, sucrose fatty acid ester, magnesium stearate, calcium stearate, aluminum stearate, and polyethylene glycol.

Examples of flowability enhancers include light anhydrous silicic acid, dried aluminum hydroxide gel, synthetic aluminum silicate, and magnesium silicate.

An injection preparation is produced in accordance with a conventional technique. In general, a diluent, such as distilled water for injection, physiologic saline, aqueous glucose solution, olive oil, sesame oil, arachis oil, soybean oil, corn oil, propylene glycol, or polyethylene glycol, can be used. Further, a disinfectant, preservative, or stabilizer may be added, according to need. From the viewpoint of safety, a vial or another container may be filled with an injection preparation, the resultant may be frozen, moisture may be removed via a conventional lyophilization technique, and a solution may then be prepared from the lyophilization product immediately before use. Furthermore, an isotonizing agent, stabilizer, preservative, soothing agent, or the like may be added, according to need.

Examples of other forms of parenteral preparations include liquid preparations for external use, liniments, such as ointments, adhesive skin patches, and suppositories for intrarectal administration. Parenteral preparations are produced in accordance with conventional techniques.

The preparation of the present invention can be administered at a frequency of once to several instances every day to once to several instances every week to month, although the frequency of administration varies in accordance with the dosage form, the route of administration, and other conditions.

In order to achieve desirable efficacy of oral preparations, in general, it is suitable for an adult to take 1 to 200 mg of the compound (I) in several separate instances per day, although the dosage varies depending on, for example, age, body weight, and severity of symptoms of a patient.

In order to achieve desirable efficacy of parenteral preparations, in general, it is adequate for an adult to take 1 to 50 mg of the compound (I) per day by means of intravenous injection, intravenous drip infusion, subcutaneous injection, or intramuscular injection, although the dosage varies depending on, for example, age, body weight, and severity of symptoms of a patient.

The pharmaceutical composition of the present invention can be used in combination with another agent for treating or inhibiting recurrence of leukemia, an immunostimulator, or the like. In such a case, the dosage described below can be adequately modified, according to need.

(Screening Method)

The present invention also provides a method for screening for an agent (a candidate compound) for treatment or prevention of acute myeloid leukemia comprising selection of a compound that reduces the HCK gene expression level or activity of a protein encoded by such gene and also reduces the FLT3 gene expression level or activity of a protein encoded by such gene.

According to an embodiment of the present invention, the screening method involves the use of the expression levels of the HCK genes and the FLT3 genes in leukemia stem cells as indicators. The compounds that reduce the expression levels of the HCK and FLT3 genes are expected to serve as agents for treatment or prevention of acute myeloid leukemia.

The method for screening for an agent for treatment or prevention of acute myeloid leukemia according to the present invention comprises, for example, steps (a) to (c) below:

(a) bringing leukemia stem cells into contact with a test compound;

(b) measuring the expression level of the HCK genes and the FLT3 genes in the leukemia stem cells; and (c) selecting a compound that reduces the expression levels to levels lower than those measured in the absence of the test compound.

According to this method, subsequently, a compound that reduces the expression levels of interest to levels lower than those measured when the test compound is not brought into contact therewith (i.e., those of the control) is selected. The selected compound would serve as an agent for treatment or prevention of acute myeloid leukemia.

According to another embodiment of the screening method of the present invention, a compound that reduces the expression levels of the HCK genes and the FLT3 genes is identified using the expression of the reporter gene as an indicator.

The method for screening for an agent for treatment or prevention of acute myeloid leukemia according to the present invention comprises, for examples, steps (a) to (c) below:

(a) bringing cells comprising a DNA structure in which the transcription regulatory region of the HCK gene is operably linked to a reporter gene and a DNA structure in which the transcription regulatory region of the FLT3 gene is operably linked to a reporter gene into contact with a test compound;

(b) measuring the expression levels of the reporter genes; and (c) selecting a compound that reduces the expression levels to levels lower than those measured in the absence of the test compound.

According to this method, at the outset, cells or a cell extract containing a DNA structure in which the transcription regulatory region of the HCK gene is operably linked to a reporter gene and a DNA structure in which the transcription regulatory region of the FLT3 gene is operably linked to a reporter gene are brought into contact with a test compound. The term "operably linked" used herein refers to a situation in which the transcription regulatory region of the HCK gene and the reporter gene are linked to each other in such a manner that the expression of the reporter gene is induced upon binding of a transcription factor to the transcription regulatory region of the HCK or FLT3 gene. Even if the reporter gene binds to a different gene and forms a fusion protein with another gene product, accordingly, the transcription regulatory region of the HCK or FLT3 gene is considered to be "operably linked" to the reporter gene if such fusion protein is induced to express upon binding of a transcription factor to the transcription regulatory region of the HCK or FLT3 gene. A person skilled in the art is capable of acquiring a transcription regulatory region of the HCK or FLT3 gene in the genome by a method well known in the art on the basis of the cDNA nucleotide sequence of the HCK or FLT3 gene.

Any type of reporter gene can be used in the method of the present invention without particular limitation, provided that the expression thereof is detectable. Examples thereof include the CAT gene, the lacZ gene, the luciferase gene, and the GFP gene. An example of a "cell comprising a DNA structure in which the transcription regulatory region of the HCK gene is operably linked to a reporter gene and a DNA structure in which the transcription regulatory region of the FLT3 gene is operably linked to a reporter gene" is a cell into which a vector comprising a structure described above has been introduced. A reporter gene linked to a given gene is preferably different from a reporter gene linked to another gene. Such vector can be prepared by a method well known in the art. A vector can be introduced into a cell by a general technique, such as calcium phosphate precipitation, electroporation, use of lipofectamine, or microinjection. The "cell comprising a DNA structure in which the transcription regulatory region of the HCK gene is operably linked to a reporter gene and a DNA structure in which the transcription regulatory region of the FLT3 gene is operably linked to a reporter gene" encompasses a cell into the chromosome of which the structure as described above has been introduced. A DNA structure can be introduced into a chromosome by a method that is commonly employed by a person skilled in the art, such as a gene introduction method via homologous recombination.

A "cell extract containing a DNA structure in which the transcription regulatory region of the HCK gene is operably linked to a reporter gene and a DNA structure in which the transcription regulatory region of the FLT3 gene is operably linked to a reporter gene" can be prepared by, for example, adding a DNA structure in which the transcription regulatory region of the HCK gene is operably linked to a reporter gene and a DNA structure in which the transcription regulatory region of the FLT3 gene is operably linked to a reporter gene to a cell extract included in a commercially available in vitro transcription/translation kit.

"Contact" in the method of the present invention can be performed by adding a test compound to a culture solution of a "cell comprising a DNA structure in which the transcription regulatory region of the HCK gene is operably linked to a reporter gene and a DNA structure in which the transcription regulatory region of the FLT3 gene is operably linked to a reporter gene" or adding a test compound to a commercially available cell extract containing such DNA. When a test compound is a protein, for example, a DNA vector that expresses such protein can be introduced into the cell. Thus, "contact" of interest can be performed.

In the method of the present invention, subsequently, the reporter gene expression level is measured. The reporter gene expression level can be measured by a method known in the art in accordance with reporter gene type. When a reporter gene is a CAT gene, for example, acetylation of chloramphenicol caused by the gene product is detected, so that the reporter gene expression level can be measured. When a reporter gene is a lacZ gene, color development of a pigment compound caused by catalytic action of the gene expression product may be detected. When a reporter gene is a luciferase gene, fluorescence emitted by a fluorescent compound caused by catalytic action of the gene expression product may be detected. When a reporter gene is a GFP gene, fluorescence emitted by the GFP protein may be detected. Thus, reporter gene expression levels can be measured.

In the method of the present invention, subsequently, a compound that reduces (inhibits) the expression level to a level lower than that measured in the absence of the test compound is selected. The compound that reduces (inhibits) the expression level would serve as an agent for treatment or prevention of acute myeloid leukemia.

EXAMPLES

Hereinafter, the present invention will be described more specifically by way of Examples, but the scope of the present invention is not intended to be limited to the following Examples.

Example 1

Synthesis of 7-[trans-4-(4-methyl-1-piperazinyl) cyclohexyl]-5-(4-phenoxyphenyl)-7H-pyrrolo[2,3-d] pyrimidin-4-amine

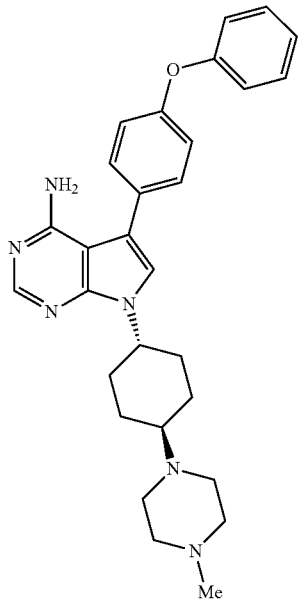 [SMILES: CN1CCN([C@H]2CC[C@H](n3cc(-c4ccc(Oc5ccccc5)cc4)c4c(N)ncnc43)CC2)CC1]

(1) Synthesis of 4-chloro-7-(1,4-dioxaspiro[4.5] decan-8-yl)-5-iodo-7H-pyrrolo[2,3-d]pyrimidine Diisopropyl azodicarboxylate (48.73 g) was added dropwise to a THF (700 mL) solution of triphenylphosphine (63.28 g) under ice cooling, using a dropping funnel. The dropping funnel was rinsed with THF (30 mL) to wash in any residual compound. Thereafter, the mixture was brought to room temperature, and a THF (320 mL) solution of 4-chloro-5-iodo-7H-pyrrolo[2,3-d]pyrimidine (36.84 g) and 1,4-dioxaspiro[4.5]decan-8-ol (29.46 g) was added dropwise over 50 minutes. After completion of the dropwise addition, the mixture was stirred for 3 hours at room temperature, and most of the solvent was evaporated in an evaporator. Ethyl acetate (400 mL) was added to the residue, a solid thus obtained was collected by filtration, and the solid was washed with ethyl acetate (250 mL+180 mL) and dried under reduced pressure. Thus, 4-chloro-7-(1,4-dioxaspiro[4.5]decan-8-yl)-5-iodo-7H-pyrrolo[2,3-d]pyrimidine (35.46 g) was obtained as a light brown solid.

(2) Synthesis of 4-chloro-5-(4-phenoxyphenyl)-7-(1, 4-dioxaspiro[4.5]decan-8-yl)-7H-pyrrolo[2,3-d]pyrimidine 4-Phenoxyphenylboronic acid pinacol ester (8.44 g) was dissolved in ethylene glycol dimethyl ether (300 mL), and 4-chloro-7-(1,4-dioxaspiro[4.5]decan-8-yl)-5-iodo-7H-pyrrolo[2,3-d]pyrimidine (7.97 g), sodium carbonate (6.02 g), water (200 mL) and tetrakis(triphenylphosphine)palladium (1.32 g) were sequentially added to the solution. The mixture was stirred at 80° C. for 3.5 hours. The mixture was left to cool naturally, subsequently ethyl acetate (400 mL) was added thereto, and the mixture was partitioned. The organic layer was washed with water (250 mL) and saturated brine (250 mL) and dried over anhydrous sodium sulfate, and then the solvent was distilled off under reduced pressure. A pale brown oily substance (13.8 g) was obtained, and hexane/ ethyl acetate (5:1, 40 mL) and dichloromethane (15 mL) were added thereto. A white solid precipitated therefrom was collected by filtration and dried, and thus 4-chloro-5-(4-phenoxyphenyl)-7-(1,4-dioxaspiro[4.5]decan-8-yl)-7H-pyrrolo[2,3-d]pyrimidine (5.22 g) was obtained.

(3) Synthesis of 5-(4-phenoxyphenyl)-7-(1,4-dioxaspiro[4,5]decan-8-yl)-7H-pyrrolo[2,3-d]pyrimidin-4-amine A mixture of 4-chloro-5-(4-phenoxyphenyl)-7-(1,4-dioxaspiro[4.5]decan-8-yl)-7H-pyrrolo[2,3-d]pyrimidine (7.58 g), 1,4-dioxane (120 mL), and a concentrated aqueous ammonia solution (120 mL) was heated in a pressure vessel at 120° C. for 17 hours. The mixture was cooled to ambient temperature, and the solvent was distilled off under reduced pressure. Thus, a light brown solid (8.3 g) was obtained. This was used in the subsequent reaction without being purified.

(4) Synthesis of 4-[4-amino-5-(4-phenoxyphenyl)-7H-pyrrolo[2,3-d]pyrimidin-7-yl]cyclohexanone A mixture of the product of the previous process, THF (30 mL), acetone (150 mL), and 6 M hydrochloric acid (109 mL) was stirred at 40° C. for 4 hours. The mixture was cooled in ice, a 1 M aqueous solution of sodium hydroxide (820 mL) was added thereto to adjust the mixture to pH 8, and a light brown solid thus produced was collected by filtration. The solid was purified by silica gel column chromatography (chloroform/methanol=50/1→20/1), and thus 4-[4-amino-5-(4-phenoxyphenyl)-7H-pyrrolo[2,3-d]pyrimidin-7-yl]cyclohexanone (4.82 g) was obtained.

(5) Synthesis of 7-[cis-4-(4-methyl-1-piperazinyl) cyclohexyl]-5-(4-phenoxyphenyl)-7H-pyrrolo[2,3-d] pyrimidin-4-amine and 7-[trans-4-(4-methyl-1-piperazinyl)cyclohexyl]-5-(4-phenoxyphenyl)-7H-pyrrolo[2,3-d]pyrimidin-4-amine 4-[4-Amino-5-(4-phenoxyphenyl)-7H-pyrrolo[2,3-d]pyrimidin-7-yl]cyclohexanone (8.23 g) was dissolved in 1,2-dichloroethane (330 mL), and acetic acid (3.73 g), N-methylpiperazine (6.22 g) and sodium triacetoxyborohydride (6.58 g) were added thereto. The mixture was stirred for 5.5 hours at room temperature. Water (100 mL) and chloroform (100 mL) were added to the reaction mixture, a saturated aqueous solution of sodium hydrogen carbonate (100 mL) was further added thereto, and the mixture was partitioned. The organic layer was washed with saturated brine (140 mL) and dried over anhydrous sodium sulfate, and then the solvent was distilled off. The residue was purified by column chromatography (chloroform→chloroform/methanol 20/1), and 7-[cis-4-(4-methyl-1-piperazinyl)cyclohexyl]-5-(4-phenoxyphenyl)-7H-pyrrolo[2,3-d]pyrimidin-4-amine (12.1 g) and 7-[trans-4-(4-methyl-1-piperazinyl)cyclohexyl]-5-(4-phenoxyphenyl)-7H-pyrrolo[2,3-d]pyrimidin-4-amine (3.8 g) were obtained.

$^1$H NMR (270 MHz, CDCl$_3$, δ): 8.33 (s, 1H), 7.46-7.32 (m, 4H), 7.20-7.03 (m, 5H), 7.01 (s, 1H), 5.07 (s, 2H), 4.68 (m, 1H), 2.73-2.58 (m, 4H), 2.58-2.35 (m, 5H), 2.30 (s, 3H), 2.27-2.14 (m, 2H), 2.14-2.00 (m, 2H), 1.90-1.70 (m, 2H), 1.70-1.50 (m, 2H).

MS (m/z)=483.50 [M+H]

HCK IC50 (nM); 1.1, FLT3-ITD IC50 (nM); 26.7

Examples 2 to 59

Example 2

RK-0020690

7-((1r,4r)-4-(8-Methyl-3,8-diazabicyclo[3.2.1]octan-3-yl)cyclohexyl)-5-(4-phenoxyphenyl)-7H-pyrrolo[2,3-d]pyrimidin-4-amine

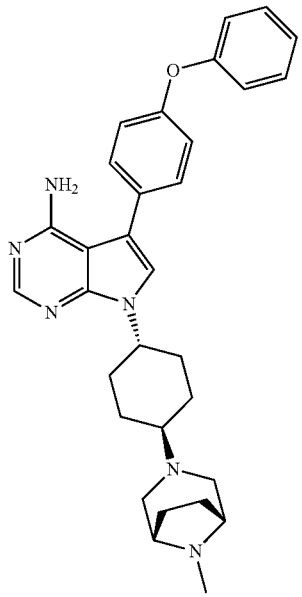 [SMILES: CN1[C@@H]2CC[C@H]1CN([C@H]1CC[C@H](n3cc(-c4ccc(Oc5ccccc5)cc4)c4c(N)ncnc43)CC1)C2]

The title compound (white solid) was obtained according to the synthesis method of Example 1, by using 8-methyl-3,8-diazabicyclo[3.2.1]octane instead of N-methylpiperazine in step (5).

$^1$H NMR (270 MHz, CDCl$_3$, δ): 8.33 (s, 1H), 7.44-7.35 (m, 4H), 7.17-7.00 (m, 5H), 7.00 (s, 1H), 5.04 (s, 2H), 4.66 (m, 1H), 3.08 (s, 2H), 2.57 (s, 4H), 2.30 (s, 3H), 2.19 (m, 2H), 2.15-1.75 (m, 8H), 1.25 (m, 2H).

MS (m/z)=509.30 [M+H]

HCK IC50 (nM); 5.0, FLT3-ITD IC50 (nM); 18.0

Example 3

RK-0020721

2-(((trans)-4-(4-Amino-5-(4-phenoxyphenyl)-7H-pyrrolo[2,3-d]pyrimidin-7-yl)cyclohexyl)amino) acetic acid.trihydrochloride

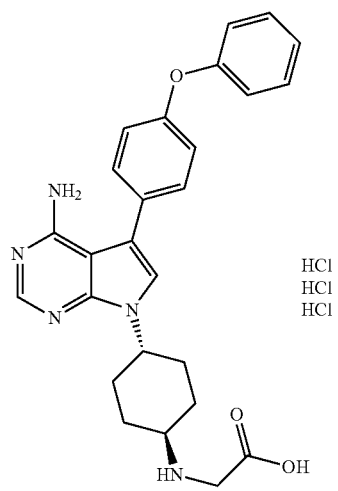 [SMILES: Nc1ncnc2c1c(-c1ccc(Oc3ccccc3)cc1)cn2[C@H]1CC[C@H](NCC(=O)O)CC1]

(1) tert-Butyl 2-((trans)-4-(4-amino-5-(4-phenoxyphenyl)-7H-pyrrolo[2,3-d]pyrimidin-7-yl)cyclohexyl)amino)acetate The title compound was synthesized according to the synthesis method of Example 1, by using tert-butyl glycine hydrochloride instead of N-methylpiperazine in step (5).

(2) 2-((trans)-4-(4-Amino-5-(4-phenoxyphenyl)-7H-pyrrolo[2,3-d]pyrimidin-7-yl)cyclohexyl)amino) acetic acid.trihydrochloride tert-Butyl 2-(((trans)-4-(4-amino-5-(4-phenoxyphenyl)-7H-pyrrolo[2,3-d]pyrimidin-7-yl)cyclohexyl)amino)acetate (93 mg, 0.18 mmol) was dissolved in 4 M hydrochloric acid (2 mL), and the solution was stirred for 3 hours at room temperature. The solvent was distilled off under reduced pressure, and then the residue was washed by adding IPE. Thus, the title compound (white solid, 83 mg) was obtained.

$^1$H NMR (270 MHz, CD$_3$OD, δ): 8.34 (s, 1H), 7.60 (s, 1H), 7.52-7.46 (m, 2H), 7.43-7.36 (m, 2H), 7.19-7.10 (m, 3H), 7.05-7.10 (m, 2H), 4.95-4.75 (s, 1H), 4.00 (s, 2H), 3.43-3.30 (m, 1H), 2.42-2.32 (m, 2H), 2.28-2.18 (m, 2H), 2.18-2.06 (m, 2H), 1.83-1.68 (m, 2H).

MS (m/z)=458.36[M+H].

HCK IC50 (nM); 4.2, FLT3-ITD IC50 (nM); 24.0

Example 4

RK-0020730

N-(4-(4-amino-7-((trans)-4-(3-methyl-5,6-dihydro[1,2,4]triazolo[4,3-a]pyrazin-7(8H)-yl)cyclohexyl)-7H-pyrrolo[2,3-d]pyrimidin-5-yl)-2-methoxyphenyl)-1-methyl-1H-indole-2-carboxamide

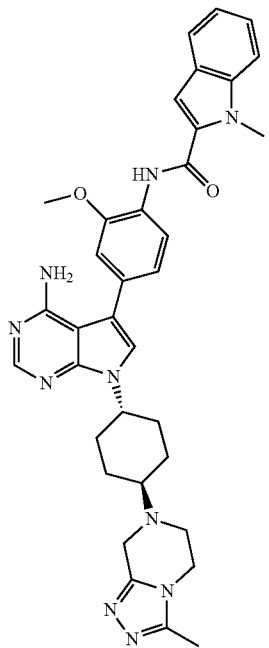 [SMILES: COc1cc(-c2cn([C@H]3CC[C@H](N4CCn5c(C)nnc5C4)CC3)c3ncnc(N)c23)ccc1NC(=O)c1cc2ccccc2n1C]

(1) tert-Butyl (4-(4-amino-7-(4-oxocyclohexyl)-7H-pyrrolo[2,3-d]pyrimidin-5-yl)-2-methoxyphenyl) carbamate tert-Butyl (2-methoxy-4-(4,4,5,5-tetramethyl-1,3,2-dioxaborolan-2-yl)phenyl)carbamate (0.6 g, 1.74 mmol) was dissolved in ethylene glycol dimethyl ether (74 mL) and ethanol (20 mL), and 4-(4-amino-5-iodo-7H-pyrrolo[2,3-d]pyrimidin-7-yl)cyclohexanone (0.5 g, 1.45 mmol), a saturated sodium carbonate solution (8.6 mL) and tetrakis(triphenylphosphine)palladium (117 mg, 0.10 mmol) were sequentially added thereto. The mixture was stirred overnight in an argon atmosphere at 80° C. The mixture was left to cool, subsequently dichloromethane was added thereto, and the mixture was extracted. The extract was partitioned and washed with saturated brine. The organic layer was dried over anhydrous sodium sulfate, and then the solvent was distilled off under reduced pressure. A pale brown oily substance (0.9 g) thus obtained was purified by silica gel column chromatography (dichloromethane/methanol=95/5), and tert-butyl (4-(4-amino-7-(4-oxocyclohexyl)-7H-pyrrolo[2,3-d]pyrimidin-5-yl)-2-methoxyphenyl)carbamate (0.7 g) was obtained.

(2) 4-(4-Amino-5-(4-amino-3-methoxyphenyl)-7H-pyrrolo[2,3-d]pyrimidin-7-yl)cyclohexanone tert-Butyl (4-(4-amino-7-(4-oxocyclohexyl)-7H-pyrrolo[2,3-d]pyrimidin-5-yl)-2-methoxyphenyl)carbamate (0.7 g, 1.51 mmol) was dissolved in acetone/methanol (1/1, 10 mL), 5 M hydrochloric acid (5 mL) was added thereto, and the mixture was heated to reflux for 2 hours. The mixture was adjusted to pH 9 with a 2 M sodium hydroxide solution, and the mixture was concentrated under reduced pressure. Subsequently, ethyl acetate was added to the mixture, the mixture was extracted, and the extract was partitioned and washed with saturated brine. The organic layer was dried over anhydrous sodium sulfate, and then the solvent was distilled off under reduced pressure. A pale brown oily substance (0.8 g) thus obtained was purified by silica gel column chromatography (dichloromethane/methanol=10/1), and thus 4-(4-amino-5-(4-amino-3-methoxyphenyl)-7H-pyrrolo[2,3-d]pyrimidin-7-yl)cyclohexanone (0.4 g) was obtained.

(3) N-(4-(4-amino-7-(4-oxocyclohexyl)-7H-pyrrolo[2,3-d]pyrimidin-5-yl)-2-methoxyphenyl)-1-methyl-1H-indole-2-carboxamide Pyridine (1 mL) was added to 4-(4-amino-5-(4-amino-3-methoxyphenyl)-7H-pyrrolo[2,3-d]pyrimidin-7-yl)cyclohexanone (0.4 g, 2.00 mmol) dissolved in dichloromethane (2 mL), and the mixture was stirred for 5 minutes under ice cooling. 1-Methyl-1H-indole-2-carbonyl chloride (0.2 g, 1.10 mmol) dissolved in dichloromethane (5 mL) was added dropwise to the mixture, and the resulting mixture was stirred for 30 minutes under ice cooling. Water (10 mL) was added thereto to terminate the reaction, subsequently dichloromethane was added thereto, and the mixture was extracted. The extract was partitioned and washed with saturated brine. The organic layer was dried over anhydrous sodium sulfate, and then the solvent was distilled off under reduced pressure. A pale brown oily substance (0.6 g) thus obtained was purified by silica gel column chromatography (dichloromethane/methanol=95/5), and thus the title compound (0.3 g) was obtained.

(4) N-(4-(4-amino-7-((cis)-4-(3-methyl-5,6-dihydro[1,2,4]triazolo[4,3-a]pyrazin-7(8H)-yl)cyclohexyl)-7H-pyrrolo[2,3-d]pyrimidin-5-yl)-2-methoxyphenyl)-1-methyl-1H-indole-2-carboxamide and N-(4-(4-amino-7-((trans)-4(3-methyl-5,6-dihydro[1,2,4]triazolo[4,3-a]pyrazin-7(8H)-yl)cyclohexyl-7H-pyrrolo[2,3-d]pyrimidin-5-yl)-2-methoxyphenyl)-1-methyl-1H-indole-2-carboxamide N-(4-(4-amino-7-(4-oxocyclohexyl)-7H-pyrrolo[2,3-d]pyrimidin-5-yl)-2-methoxyphenyl)-1-methyl-1H-indole-2-carboxamide (0.5 g, 0.98 mmol) was dissolved in 1,2-dichloroethane (20 mL), and acetic acid (0.2 g, 2.95 mmol), 3-methyl-5,6,7,8-tetrahydro-[1,2,4]triazolo[4,3-a]pyrazine (0.2 g, 1.48 mmol), and sodium triacetoxyborohydride (0.3 g, 1.48 mmol) were added to the solution. The mixture was stirred overnight at room temperature. The reaction mixture was concentrated under reduced pressure, and then the concentrated mixture was extracted with ethyl acetate. The extract was partitioned and washed with water. The organic layer was dried over anhydrous sodium sulfate, and then the solvent was distilled off under reduced pressure. The residue was purified by preparative thin film chromatography (dichloromethane/methanol/28% aqueous ammonia=100/10/2). Thus, N-(4-(4-amino-7-((cis)-4-(3-methyl-5,6-dihydro[1,2,4]triazolo[4,3-a]pyrazin-7(8H)-yl)cyclohexyl)-7H-pyrrolo[2,3-d]pyrimidin-5-yl)-2-methoxyphenyl)-1-methyl-1H-indole-2-carboxamide (38 mg) and N-(4-(4-amino-7-((trans)-4-(3-methyl-5,6-dihydro[1,2,4]triazolo[4,3-a]pyrazin-7(8H)-yl)cyclohexyl)-7H-pyrrolo[2,3-d]pyrimidin-5-yl)-2-methoxyphenyl)-1-methyl-1H-indole-2-carboxamide (purple solid, 98 mg) were obtained.

$^1$H NMR (270 MHz, CDCl$_3$, δ): 8.62 (s, 1H), 8.56 (d, J=8.4 Hz, 1H), 8.34 (s, 1H), 7.70 (d, J=8.1 Hz, 2H), 7.38 (m, 2H), 7.22-7.04 (m, 4H), 5.27 (s, 2H), 4.75 (m, 1H), 4.14 (s, 3H), 4.01 (s, 3H), 4.99 (s, 2H), 3.87 (t, J=5.1 Hz, 2H), 3.01 (t, J=5.1 Hz, 2H), 2.76 (m, 1H), 2.30 (s, 3H), 2.26 (br, 2H), 2.10 (br, 2H), 1.94-1.55 (m, 4H).

MS (m/z)=616.31 [M+H].

HCK IC50 (nM); 0.8, FLT3-ITD IC50 (nM); >2500, hERG inhibition (automated patch-clamp), 10 µM; 49%

Example 5

RK-0020694

Synthesis of 5-(4-phenoxyphenyl)-7-((cis)-4-((pyridin-4-ylmethyl)amino)cyclohexyl)-7H-pyrrolo[2,3-d]pyrimidin-4-amine

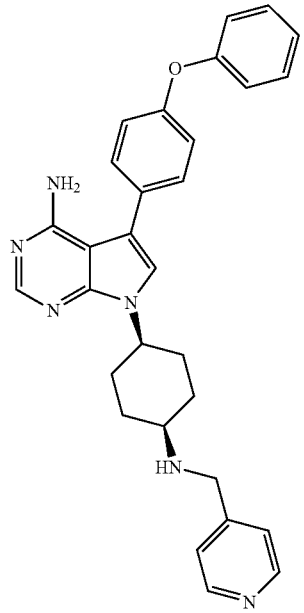 [SMILES: Nc1ncnc2c1c(-c1ccc(Oc3ccccc3)cc1)cn2[C@H]1CC[C@@H](NCc2ccncc2)CC1]

The title compound (white solid) was obtained according to the synthesis method of Example 1, by using 4-picolylamine instead of N-methylpiperazine in step (5).

$^1$H NMR (270 MHz, CDCl$_3$, δ): 8.59-8.54 (m, 2H), 8.22 (s, 1H), 7.47-7.30 (m, 6H), 7.20-7.04 (m, 6H), 6.12 (br, 2H), 4.82-4.66 (m, 1H), 3.84 (s, 2H), 3.06-2.93 (m, 1H), 2.30-2.10 (m, 4H), 2.00-1.70 (m, 4H).

MS (m/z)=491.58[M+H].

HCK IC50 (nM); 0.75, FLT3-ITD IC50 (nM); 6.6

Example 6

RK-0020709

7-([1,4'-bipiperidin]-4-yl)-5-(4-phenoxyphenyl)-7H-pyrrolo[2,3-d]pyrimidin-4-amine

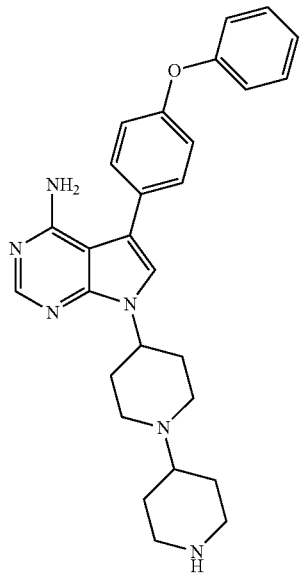 [SMILES: Nc1ncnc2c1c(-c1ccc(Oc3ccccc3)cc1)cn2C1CCN(C2CCNCC2)CC1]

(1) tert-Butyl 4-(4-chloro-5-iodo-7H-pyrrolo[2,3-d]pyrimidin-7-yl)piperidine-1-carboxylate A 40% toluene solution of diisopropyl azodicarboxylate at 1.9 mol/L (2.8 mL, 5.37 mmol) was added dropwise to a solution of triphenylphosphine (1.4 g, 5.37 mmol) in THF (60 mL) under ice cooling with stirring. The mixture was returned to room temperature, and a THF (15 mL) solution of 4-chloro-5-iodo-7H-pyrrolo[2,3-d]pyrimidine (1.0 g, 3.58 mmol) and tert-butyl 4-hydroxypiperidine-1-carboxylate (1.1 g, 5.37 mmol) was added dropwise thereto. After completion of the dropwise addition, the mixture was stirred for 3 hours at room temperature, and the solvent was distilled off under reduced pressure. The residue thus obtained was purified by silica gel column chromatography (hexane/ethyl acetate=3/1), and thus the title compound (white solid, 0.7 g) was obtained.

(2) tert-Butyl 4-(4-chloro-5-(4-phenoxyphenyl)-7H-pyrrolo[2,3-d]pyrimidin-7-yl)piperidine-1-carboxylate tert-Butyl 4-(4-chloro-5-iodo-7H-pyrrolo[2,3-d]pyrimidin-7-yl)piperidine-1-carboxylate (0.7 g, 1.49 mmol) and 4,4,5,5-tetramethyl-2-(4-phenoxyphenyl)-1,3,2-dioxaborolane (0.5 mg, 1.79 mmol) were dissolved in ethylene glycol dimethyl ether (25 mL), and a saturated aqueous solution of sodium carbonate (5 mL) and tetrakis(triphenylphosphine)palladium (0.1 g, 0.10 mmol) were sequentially added thereto. The mixture was stirred overnight at 80° C. After the mixture was left to cool naturally, water was added thereto, and the mixture was extracted with ethyl acetate. The extract was dried over anhydrous sodium sulfate, and the solvent was distilled off under reduced pressure. The residue thus obtained was purified by silica gel column chromatography (hexane/ethyl acetate=3/1), and thus the title compound (yellow solid, 0.6 g) was obtained.

(3) 5-(4-Phenoxyphenyl)-7-(piperidin-4-yl)-7H-pyrrolo[2,3-d]pyrimidin-4-amine A mixture of tert-butyl 4-(4-chloro-5-(4-phenoxyphenyl)-7H-pyrrolo[2,3-d]pyrimidin-7-yl)piperidine-1-carboxylate (0.2 g, 0.44 mmol), 1,4-dioxane (10 mL), and 28% aqueous ammonia was heated in a pressure vessel for 17 hours at 120° C. The reaction liquid was returned to room temperature, the solvent was distilled off under reduced pressure, and the title compound (white solid, 0.2 g) was obtained.

(4) 5-(4-Phenoxyphenyl)-7-(piperidin-4-yl)-7H-pyrrolo[2,3-d]pyrimidin-4-amine A mixture of 5-(4-phenoxyphenyl)-7-(piperidin-4-yl)-7H-pyrrolo[2,3-d]pyrimidin-4-amine (0.2 g, 0.37 mmol), acetone (5 mL), 5 M hydrochloric acid (1 mL), and trifluoroacetic acid (0.5 mL) was stirred for 2 hours at 80° C. After the solvent was concentrated, a 2 M sodium hydroxide solution was added thereto to adjust the mixture to pH 8, and the mixture was extracted with dichloromethane. The organic layer was dried over anhydrous sodium sulfate, and then the solvent was distilled off under reduced pressure. Thus, the title compound (white solid, 0.1 g) was obtained.

(5) tert-Butyl 4-(4-amino-5-(4-phenoxyphenyl)-7H-pyrrolo[2,3-d]pyrimidin-7-yl)-[1,4'-bipiperidine]-1'-carboxylate A mixture of 5-(4-phenoxyphenyl)-7-(piperidin-4-yl)-7H-pyrrolo[2,3-d]pyrimidin-4-amine (0.2 g, 0.47 mmol), tert-butyl 4-oxopiperidine-1-carboxylate (0.3 g, 1.41 mmol), acetic acid (0.1 mL), and 1,2-dichloroethane (5 mL) was stirred for 10 minutes at room temperature, sodium triacetoxyborohydride (0.1 g 0.70 mmol) was added thereto, and the resulting mixture was stirred overnight. Water was added thereto to terminate the reaction, the reaction mixture was extracted with dichloromethane, and then the organic layer was distilled off under reduced pressure. The residue thus obtained was purified by silica gel column chromatography (dichloromethane/methanol=10/1), and the title compound (white solid, 0.1 g) was obtained.

(6) 7-([1,4'-Bipiperidin]-4-yl)-5-(4-phenoxyphenyl)-7H-pyrrolo[2,3-d]pyrimidin-4-amine A mixture of tert-butyl 4-(4-amino-5-(4-phenoxyphenyl)-7H-pyrrolo[2,3-d]pyrimidin-7-yl)-[1,4'-bipiperidine]-1'-carboxylate (0.1 g, 0.20 mmol), THF (5 mL) and 5 M hydrochloric acid (1 mL) was stirred for one hour at 50° C. After stirring, the mixture was brought to room temperature, and was adjusted to pH 11 with sodium hydroxide. Subsequently, the solvent was distilled off under reduced pressure. Ethanol was added to the residue, the mixture was filtered, and then the filtrate was concentrated under reduced pressure. Thus, the title compound (white solid, 73 mg) was obtained.

$^1$H NMR (270 MHz, CDCl$_3$, δ): 8.28 (s, 1H), 7.47-7.33 (m, 4H), 7.20-7.00 (m, 6H), 5.42 (br, 2H), 4.90-4.60 (m, 2H), 3.50-3.30 (m, 2H), 3.20-2.98 (m, 2H), 2.90-2.66 (m, 3H), 2.66-2.35 (m, 3H), 2.20-1.70 (m, 8H).

MS (m/z)=469.44 [M+H].

HCK IC50 (nM); 0.7, FLT3-ITD IC50 (nM); 43.0

Example 7

RK-0020781

7-(1-(((trans)-8-Methyl-8-azabicyclo[3.2.1]octan-3-yl)piperidin-4-yl)-5-(4-phenoxyphenyl)-7H-pyrrolo[2,3-d]pyrimidin-4-amine

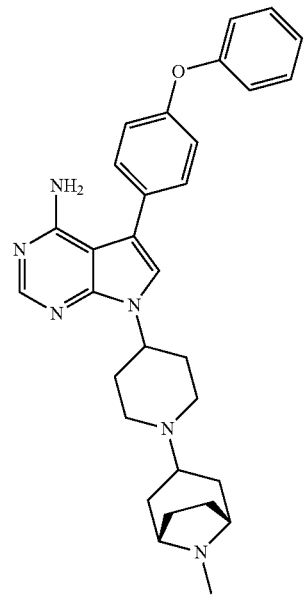 [SMILES: CN1[C@@H]2CC[C@H]1CC(N1CCC(n3cc(-c4ccc(Oc5ccccc5)cc4)c4c(N)ncnc43)CC1)C2]

The title compound (yellow oily substance) was obtained according to the synthesis method of Example 6, by using tropinone instead of tert-butyl 4-oxopiperazine-1-carboxylate in step (5).

$^1$H NMR (270 MHz, CDCl$_3$, δ): 8.32 (s, 1H), 7.45-7.34 (m, 4H), 7.18-7.05 (m, 6H), 5.11 (s, 2H), 4.08 (m, 1H), 3.25 (br, 2H), 3.06 (br, 2H), 2.73 (m, 1H), 2.44 (br, 2H), 2.32 (s, 3H), 2.06-1.97 (m, 6H), 1.79 (br, 2H), 1.24 (m, 3H).

MS (m/z)=509.30 [M+H].

HCK IC50 (nM); 0.59, FLT3-ITD IC50 (nM); 23.0

Example 8

RK-0020888

1-((1s,4s)-4-((8-Methyl-8-azabicyclo[3.2.1]octan-3-yl)amino)cyclohexyl)-3-(4-phenoxyphenyl)-1H-pyrazolo[3,4-d]pyrimidin-4-amine

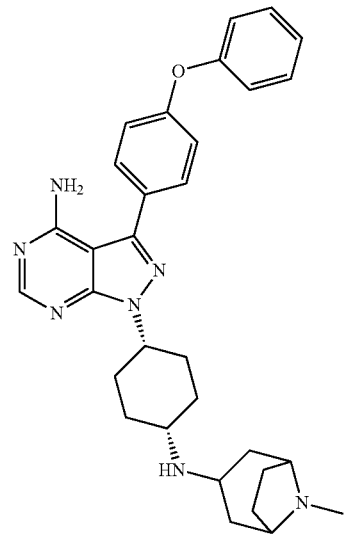 [SMILES: CN1C2CCC1CC(N[C@H]1CC[C@@H](n3nc(-c4ccc(Oc5ccccc5)cc4)c4c(N)ncnc43)CC1)C2]

(1) 3-iode-1-(1,4-dioxaspiro[4.5]decan-8-yl)-1H-pyrazolo[3,4-d]pyrimidin-4-amine Potassium carbonate (5.4 g, 39.0 mmol), 18-crown ether (0.5 g, 2.0 mmol), and potassium iodide (0.3 g, 1.95 mmol) were added to a solution of 3-iodo-1H-pyrazolo[3,4-d]pyrimidin-4-amine (5.1 g, 19.5 mmol) and 1,4-dioxaspiro[4.5]decan-8-yl 4-methylbenzenesulfonate (6.9 g, 21.4 mmol) dissolved in DMF (36.8 mL), and this mixture liquid was stirred overnight at 80° C. A precipitate was collected by filtration, and the filtrate was concentrated under reduced pressure. Ethyl acetate was added thereto, the mixture was extracted, and the extract was partitioned and washed with saturated brine. The organic layer was dried over anhydrous sodium sulfate, and then the solvent was distilled off under reduced pressure. A brown solid thus obtained was used in the subsequent reaction without being purified.

(2) 4-(4-Amino-3-iodo-1H-pyrazolo[3,4-d]pyrimidin-1-yl)cyclohexanone 3-iodo-1-(1,4-dioxaspiro[4.5]decan-8-yl)-1H-pyrazolo[3,4-d]pyrimidine was dissolved in acetone (50 mL), 5 M hydrochloric acid was added thereto, and the mixture was heated to reflux for one hour. The mixture was concentrated under reduced pressure, subsequently ethyl acetate was added thereto, and the mixture was partitioned and washed with saturated brine. The organic layer was dried over anhydrous sodium sulfate, and then the solvent was distilled off under reduced pressure. A pale brown oily substance (3.2 g) thus obtained was purified by silica gel column chromatography (dichloromethane/methanol=95/5), and thus the title compound (1.5 g) was obtained.

(3) 4-(4-Amino-3-(4-phenoxyphenyl)-1H-pyrazolo[3,4-d]pyrimidin-1-yl)cyclohexanone 4,4,5,5-Tetramethyl-2-(4-phenoxyphenyl)-1,3,2-dioxaborolane (2.0 g, 6.72 mmol) was dissolved in ethylene glycol dimethyl ether (74 mL) and ethanol (20 mL), and 4-(4-amino-3-iodo-1H-pyrazolo[3,4-d]pyrimidin-1-yl)cyclohexanone (0.96 g, 2.69 mmol), a saturated sodium carbonate solution (23 mL) and tetrakis(triphenylphosphine) palladium (0.2 g, 0.19 mmol) were sequentially added to the solution. The mixture was stirred all night and half a day in an argon atmosphere at 80° C. After the mixture was left to cool naturally, dichloromethane was added thereto, the mixture was extracted, and the extract was partitioned and washed with saturated brine. The organic layer was dried over anhydrous sodium sulfate, and then the solvent was distilled off under reduced pressure. A pale brown oily substance (2.0 g) thus obtained was purified by silica gel column chromatography (dichloromethane/methanol=95/5), and thus the title compound (0.6 g) was obtained.

(4) 1-(4-Aminocyclohexyl)-3-(4-phenoxyphenyl)-1H-pyrazolo[3,4-d]pyrimidin-4-amine 4-(4-Amino-3-(4-phenoxyphenyl)-1H-pyrazolo[3,4-d]pyrimidin-1-yl)cyclohexanone (1 g, 2.5 mmol), ammonium acetate (2.9 g, 37.6 mmol), and 2-picoline-borane complex (0.3 g, 3.0 mmol) were weighed in a microwavable pressure-resistant vessel, and ethanol (15 mL) was added thereto. This mixture liquid was stirred in the microwave reactor at 130° C. for 2 minutes. This reaction liquid was concentrated under reduced pressure, and then was purified by silica gel column chromatography (dichloromethane/methanol=10/1). Thus, the title compound (0.34 g) was obtained.

(5) 1-((1s,4s)-4-((8-Methyl-8-azabicyclo[3.2.1]octan-3-yl)amino)cyclohexyl)-3-(4-phenoxyphenyl)-1H-pyrazolo[3,4-d]pyrimidin-4-amine 1-(4-Aminocyclohexyl)-3-(4-phenoxyphenyl)-1H-pyrazolo[3,4-d]pyrimidin-4-amine (0.2 g, 0.39 mmol) was dissolved in 1,2-dichloroethane (6 mL), and acetic acid (70 mg, 1.16 mmol), tropinone (81 mg, 0.58 mmol) and sodium triacetoxyborohydride (0.1 g, 0.58 mmol) were added thereto. The mixture was stirred overnight at room temperature. The reaction mixture was filtered and concentrated under reduced pressure. Subsequently, the reaction mixture was isolated and purified by preparative thin layer chromatography (dichloromethane/methanol/28% aqueous ammonia=100/10/2). Thus, 1-((1s,4s)-4-((8-methyl-8-azabicyclo[3.2.1]octan-3-yl)amino)cyclohexyl)-3-(4-phenoxyphenyl)-1H-pyrazolo[3,4-d]pyrimidin-4-amine (3.8 mg) and 1-((1r,4r)-4-((8-methyl-8-azabicyclo[3.2.1]octan-3-yl)amino)cyclohexyl)-3-(4-phenoxyphenyl)-1H-pyrazolo[3,4-d]pyrimidin-4-amine (12 mg) were obtained.

$^1$H NMR (270 MHz, CDCl$_3$, δ): 8.36 (s, 1H), 7.67 (d, J=1.9 Hz 2H), 7.41 (m, 2H), 7.19-7.06 (m, 5H), 5.64 (s, 2H), 4.77 (m, 1H), 3.07 (br, 2H), 2.98 (m, 2H), 2.31 (m, 1H), 2.26 (s, 3H), 2.07-1.52 (m, 14H).

MS (m/z)=524.31 [M+H].

HCK IC50 (nM); 26, FLT3-ITD IC50 (nM); 16

Example 9

RK-0020718

2-(((cis)-4-(4-Amino-5-(4-phenoxyphenyl)-7H-pyrrolo[2,3-d]pyrimidin-7-yl)cyclohexyl)amino)acetic acid.trihydrochloride

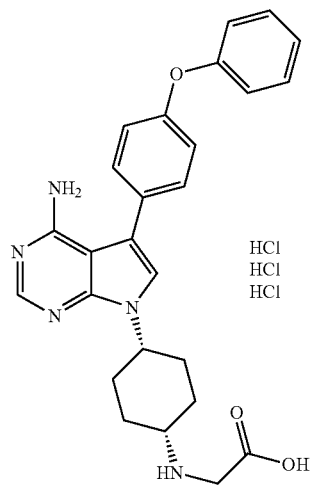 [SMILES: Nc1ncnc2c1c(-c1ccc(Oc3ccccc3)cc1)cn2[C@H]1CC[C@@H](NCC(=O)O)CC1]

tert-Butyl 2-(((cis)-4-(4-amino-5-(4-phenoxyphenyl)-7H-pyrrolo[2,3-d]pyrimidin-7-yl)cyclohexyl)amino)acetate (108 mg) was synthesized according to the synthesis method of Example 1, by using tert-butyl glycine hydrochloride instead of N-methylpiperazine in step (5). Thereafter, the compound was dissolved in 4 M hydrochloric acid (2 mL), and the solution was stirred for 3 hours at room temperature. The solvent was distilled off under reduced pressure, and then IPE was added to the residue to suspend and wash the residue. Thus, the title compound (white solid, 86 mg) was obtained.

$^1$H NMR (270 MHz, CD$_3$OD, δ): 8.34 (s, 1H), 7.73-7.68 (m, 1H), 7.53-7.49 (m, 2H), 7.43-7.37 (m, 2H), 7.19-7.11 (m, 3H), 7.11-7.00 (m, 2H), 5.03-4.92 (m, 1H), 4.00 (s, 2H), 3.62-3.55 (m, 1H), 2.40-2.15 (m, 4H), 2.15-2.03 (m, 4H).

MS (m/z)=458.38 [M+H].

HCK IC50 (nM); 16, FLT3-ITD IC50 (nM); 23

Example 10

RK-0020719

2-(((cis)-4-(4-Amino-5-(4-phenoxyphenyl)-7H-pyrrolo[2,3-d]pyrimidin-7-yl)cyclohexyl)amino)acetamide

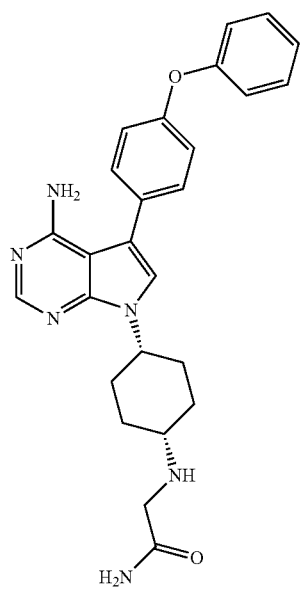 [SMILES: NC(=O)CN[C@H]1CC[C@@H](n2cc(-c3ccc(Oc4ccccc4)cc3)c3c(N)ncnc32)CC1]

The title compound (white solid) was synthesized according to the synthesis method of Example 1, by using 2-aminoacetamide instead of N-methylpiperazine in step (5).

$^1$H NMR (400 MHz, CDCl$_3$, δ): 8.31 (s, 1H), 7.44 (d, J=8.4 Hz, 2H), 7.38 (m, 2H), 7.17-7.06 (m, 5H), 7.02 (s, 1H), 5.60 (s, 1H), 5.14 (s, 2H), 4.65 (m, 1H), 3.33 (s, 2H), 2.96 (br, 1H), 2.23 (m, 2H), 1.94-1.90 (m, 4H), 1.83-1.74 (m, 2H).

MS (m/z)=457.31 [M+H].

HCK IC50 (nM); 6.5, FLT3-ITD IC50 (nM); 23

Example 11

RK-0020722

2-(((trans)-4-(4-Amino-5-(4-phenoxyphenyl)-7H-pyrrolo[2,3-d]pyrimidin-7-yl)cyclohexyl)amino)acetamide

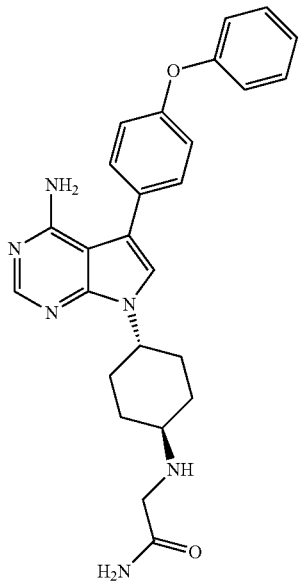 [SMILES: NC(=O)CN[C@H]1CC[C@H](n2cc(-c3ccc(Oc4ccccc4)cc3)c3c(N)ncnc32)CC1]

The title compound (white solid) was synthesized according to the synthesis method of Example 1, by using 2-aminoacetamide instead of N-methylpiperazine in step (5).

$^1$H NMR (400 MHz, CDCl$_3$, δ): 8.32 (s, 1H), 7.43 (d, J=8.8 Hz, 2H), 7.38 (m, 2H), 7.17-7.06 (m, 5H), 6.98 (s, 1H), 5.48 (s, 1H), 5.11 (s, 2H), 4.72 (m, 1H), 3.35 (s, 2H), 2.58 (m, 1H), 2.15 (m, 4H), 1.83 (m, 2H), 1.45-1.36 (m, 2H).

MS (m/z)=457.31 [M+H].

HCK IC50 (nM); 7.6, FLT3-ITD IC50 (nM); 23

Example 12

RK-0020752

N-((cis)-4-(4-5-(4-Phenoxyphenyl)-7H-pyrrolo[2,3-d]pyrimidin-7-yl)cyclohexyl)isonicotinamide

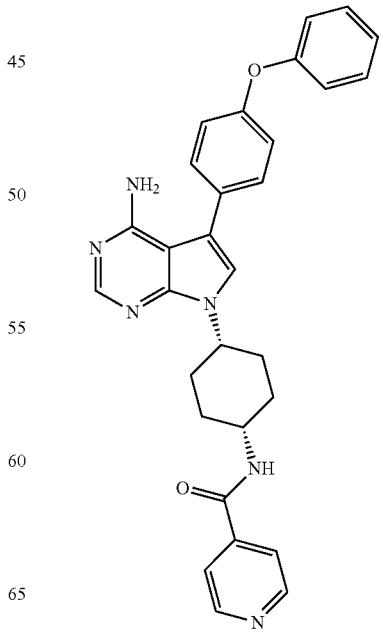

(1) 7-(4-Aminocyclohexyl)-5-(4-phenoxyphenyl)-7H-pyrrolo[2,3-d]pyrimidin-4-amine According to the synthesis method of Example 1, 4-(4-amino-5-(4-phenoxyphenyl)-7H-pyrrolo[2,3-d]pyrimidin-7-yl)cyclohexanone (0.60 g, 1.51 mmol), which was the product of step (4), ammonium acetate (1.7 g, 22.6 mmol), and 2-picoline-borane complex (0.2 g, 1.81 mmol) were weighed in a microwavable pressure-resistant vessel, and ethanol (11 mL) was added thereto. This mixture liquid was stirred in the microwave reactor at 130° C. for 2 minutes. This reaction liquid was concentrated under reduced pressure, and then was purified by silica gel column chromatography (dichloromethane/methanol=10/1→dichloromethane/methanol/28% aqueous ammonia=100/10/2). Thus, the title compound (0.3 g) was obtained.

(2) N-((cis)-4-(4-amino-5-(4-phenoxyphenyl)-7H-pyrrolo[2,3-d]pyrimidin-7-yl)cyclohexyl)isonicotinamide and N-((trans)-4-(4-amino-5-(4-phenoxyphenyl)-7H-pyrrolo[2,3-d]pyrimidin-7-yl)cyclohexyl)isonicotinamide 7-(4-Aminocyclohexyl)-5-(4-phenoxyphenyl)-7H-pyrrolo[2,3-d]pyrimidin-4-amine (100 mg, 0.27 mmol), isonicotinic acid (42 mg, 0.34 mmol), and TBTU (88 mg, 0.27 mmol) were dissolved in DMF (3 mL), and DIPEA (50 mg, 0.39 mmol) was added dropwise thereto. This solution was stirred for one hour at room temperature and concentrated under reduced pressure, and then the solution was purified by preparative thin layer chromatography (dichloromethane/methanol/28% aqueous ammonia=100/10/2). Thus, N-((cis)-4-(4-amino-5-(4-phenoxyphenyl)-7H-pyrrolo[2,3-d]pyrimidin-7-yl)cyclohexyl)isonicotinamide (white solid, 16 mg) and N-((trans)-4-(4-amino-5-(4-phenoxyphenyl)-7H-pyrrolo[2,3-d]pyrimidin-7-yl)cyclohexyl)isonicotinamide (white solid, 51 mg) were obtained.

$^1$H NMR (270 MHz, CDCl$_3$, δ): 8.81 (d, J=1.6 Hz, 1H), 8.32 (s, 1H), 7.73 (d, J=2.4 Hz, 2H), 7.45-7.41 (m, 4H), 7.18-6.99 (m, 5H), 6.06 (d, 1H, J=8.4 Hz), 5.09 (s, 2H), 4.59 (m, 1H), 4.50 (m, 1H), 2.32 (m, 2H), 2.18 (m, 4H), 1.91 (m, 2H).

MS (m/z)=505.23 [M+H].

HCK IC50 (nM); 4.0, FLT3-ITD IC50 (nM); 44.0

Example 13

RK-0020952

7-((trans)-4-(4-(tert-Butyl)piperazin-1-yl)cyclohexyl)-5-(4-phenoxyphenyl)-7H-pyrrolo[2,3-d]pyrimidin-4-amine

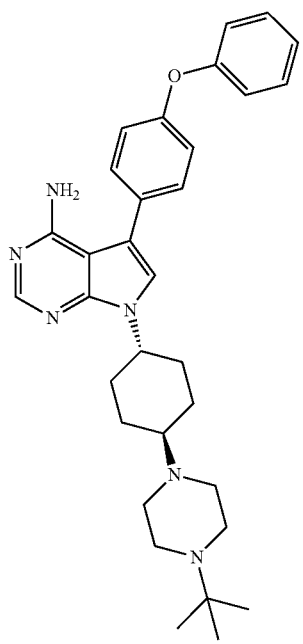 [SMILES: CC(C)(C)N1CCN([C@H]2CC[C@H](n3cc(-c4ccc(Oc5ccccc5)cc4)c4c(N)ncnc43)CC2)CC1]

The title compound (white solid) was synthesized according to the synthesis method of Example 1, by using 1-(tert-butyl)piperazine instead of N-methylpiperazine in step (5).

$^1$H NMR (270 MHz, CDCl$_3$, δ): 8.33 (s, 1H), 7.45-7.35 (m, 4H), 7.18-7.06 (m, 5H), 7.01 (s, 1H), 5.09 (s, 2H), 4.68 (m, 1H), 2.67 (br, 8H), 2.43 (m, 1H), 2.39-2.08 (m, 4H), 1.88-1.61 (m, 4H), 1.10 (s, 9H).

MS (m/z)=525.74 [M+H].

HCK IC50 (nM); 8.0, FLT3-ITD IC50 (nM); 17

Example 14

RK-0020618

N-(4-(4-amino-1-((trans)-4-(4-methylpiperazin-1-yl)cyclohexyl)-1H-pyrazolo[3,4-d]pyrimidin-3-yl)-2-methoxyphenyl)-1-methyl-1H-indole-2-carboxamide

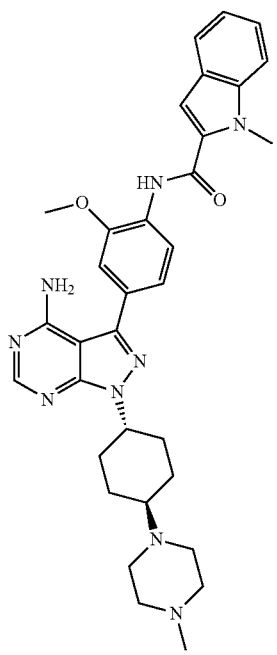 [SMILES: COc1cc(-c2nn([C@H]3CC[C@H](N4CCN(C)CC4)CC3)c3ncnc(N)c23)ccc1NC(=O)c1cc2ccccc2n1C]

(1) N-(4-(4-amino-1-(4-oxocyclohexyl)-1H-pyrazolo[3,4-d]pyrimidin-3-yl)-2-methoxyphenyl)-1-methyl-1H-indole-2-carboxamide N-(2-methoxy-4-(4,4,5,5-tetramethyl-1,3,2-dioxaborolan-2-yl)phenyl)-1-methyl-1H-indol-2-amine (0.7 g, 1.83 mmol) was dissolved in ethylene glycol dimethyl ether (16 mL) and ethanol (8.5 mL), and 4-(4-amino-3-iodo-1H-pyrazolo[3,4-d]pyrimidin-1-yl)cyclohexanone (0.54 g, 1.52 mmol), a saturated sodium carbonate solution (3.4 mL) and tetrakis(triphenylphosphine)palladium (123 mg, 0.11 mmol) were sequentially added to the solution. The mixture was stirred all night and half a day in an argon atmosphere at 80° C. After the mixture was left to cool naturally, dichloromethane was added thereto, the mixture was extracted, and the extract was partitioned and washed with saturated brine. The organic layer was dried over anhydrous sodium sulfate, and then the solvent was distilled off under reduced pressure. An oily substance thus obtained was washed with n-hexane, and thus N-(4-(4-amino-1-(4-oxocyclohexyl)-1H-pyrazolo[3,4-d]pyrimidin-3-yl)-2-methoxyphenyl)-1-methyl-1H-indole-2-carboxamide (0.9 g) was obtained.

(2) N-(4-(4-amino-1-((cis)-4-(4-methylpiperazin-1-yl)cyclohexyl)-1H-pyrazolo[3,4-d]pyrimidin-3-yl)-2-methoxyphenyl)-1-methyl-1H-indole-2-carboxamide and N-(4-(4-amino-1-((trans)-4-(4-methylpiperazin-1-yl)cyclohexyl)-1H-pyrazolo[3,4-d]pyrimidin-3-yl)-2-methoxyphenyl)-1-methyl-1H-indole-2-carboxamide N-(4-(4-amino-1-(4-oxocyclohexyl)-1H-pyrazolo[3,4-d]pyrimidin-3-yl)-2-methoxyphenyl)-1-methyl-1H-indole-2-carboxamide (0.3 g, 0.51 mmol) was dissolved in 1,2-dichloroethane (14.6 mL), and acetic acid (92 mg, 1.53 mmol), N-methylpiperazine (153 mg, 1.53 mmol) and sodium triacetoxyborohydride (0.2 g, 0.76 mmol) were added thereto. The mixture was stirred overnight at room temperature. The reaction mixture was concentrated under reduced pressure, subsequently the mixture was extracted with ethyl acetate, and the extract was partitioned and washed with water. The organic layer was dried over anhydrous sodium sulfate, and then the solvent was distilled off under reduced pressure. The residue was purified by preparative thin layer chromatography (dichloromethane/methanol/28% aqueous ammonia=100/10/2). Thus, N-(4-(4-amino-1-((cis)-4-(4-methylpiperazin-1-yl)cyclohexyl)-1H-pyrazolo[3,4-d]pyrimidin-3-yl)-2-methoxyphenyl)-1-methyl-1H-indole-2-carboxamide (white solid, 36 mg) and N-(4-(4-amino-1-((trans)-4-(4-methylpiperazin-1-yl)cyclohexyl)-1H-pyrazolo[3,4-d]pyrimidin-3-yl)-2-methoxyphenyl)-1-methyl-1H-indole-2-carboxamide (yellow solid, 48 mg) were obtained.

$^1$H NMR (270 MHz, CDCl$_3$, δ): 8.67 (d, J=8.1 Hz, 1H), 8.63 (s, 1H), 8.38 (s, 1H), 7.94 (d, J=7.8, 1H), 7.73-7.30 (m, 4H), 7.09 (s, 1H), 5.54 (s, 2H), 4.78 (m, 1H), 4.14 (s, 3H), 3.93 (s, 3H), 2.67 (br, 4H), 2.50 (br, 4H), 2.29 (s, 3H), 2.16 (br, 5H), 1.82 (br, 2H), 1.60 (br 2H).

MS (m/z)=594.30 [M+H]HCK IC50 (nM); 0.77, FLT3-ITD IC50 (nM); 2747

Example 15

RK-0020725

1-((1r,4r)-4-(8-Methyl-3,8-diazabicyclo[3.2.1]octan-3-yl)cyclohexyl)-3-(4-phenoxyphenyl)-1H-pyrazolo[3,4-d]pyrimidin-4-amine

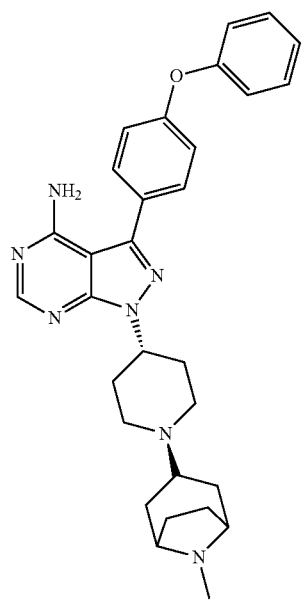

A mixture of 4-(4-amino-3-(4-phenoxyphenyl)-1H-pyrazolo[3,4-d]pyrimidin-1-yl)cyclohexanone (150 mg, 0.38 mmol), 8-methyl-3,8-diazabicyclo[3.2.1]octane dihydrochloride (75 mg, 0.38 mmol), ethanol (1.5 mL), and sodium cyanoborohydride (30 mg, 0.48 mmol) was heated in a microwave reactor at 130° C. for 2 minutes. The solvent was distilled off under reduced pressure, the residue was adjusted to pH 10 with a 2 M aqueous solution of sodium hydroxide, and the mixture was extracted with dichloromethane. The solvent was distilled off under reduced pressure, and the residue was purified by silica gel column chromatography (dichloromethane/methanol/28% aqueous ammonia=100/10/2→6/4/1), and then was further purified by preparative thin layer chromatography (dichloromethane/methanol=10/1). Thus, the title compound (white solid, 45 mg) and 1-((1s,4s)-4-(8-methyl-3,8-diazabicyclo[3.2.1]octan-3-yl)cyclohexyl)-3-(4-phenoxyphenyl)-1H-pyrazolo[3,4-d]pyrimidin-4-amine (yellow solid, 24 mg) were obtained.

$^1$H NMR (270 MHz, CDCl$_3$, δ): 8.37 (s, 1H), 7.68-7.60 (m, 2H), 7.43-7.35 (m, 2H), 7.20-7.03 (m, 5H), 5.43 (s, 2H), 4.80-4.65 (m, 1H), 3.07 (s, 2H), 2.57 (d, J=2.2 Hz, 4H), 2.47-2.32 (m, 1H), 2.26 (s, 3H), 2.20-1.69 (m, 10H), 1.60-1.40 (m, 2H).

MS (m/z)=510.50 [M+H]

HCK IC50 (nM); 0.5, FLT3-ITD IC50 (nM); 87

Example 16

RK-0020729

N-(4-(4-amino-7-((cis)-4-(3-methyl-5,6-dihydro[1,2,4]triazolo[4,3-a]pyrazin-7(8H)-yl)cyclohexyl)-7H-pyrrolo[2,3-d]pyrimidin-5-yl)-2-methoxyphenyl)-1-methyl-1H-indole-2-carboxamidamide

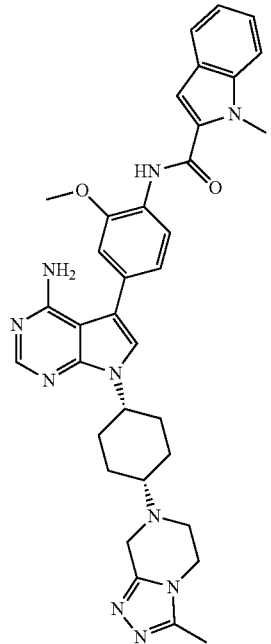 [SMILES: COc1cc(-c2cn([C@H]3CC[C@@H](N4CCn5c(C)nnc5C4)CC3)c3ncnc(N)c23)ccc1NC(=O)c1cc2ccccc2n1C]

The title compound (white solid) was obtained according to the synthesis method of Example 4, by isolating and purifying the cis-form obtained in step (4).

$^1$H NMR (270 MHz, CDCl$_3$, δ): 8.61 (s, 1H), 8.54 (d, J=7.8 Hz, 1H), 8.33 (s, 1H), 7.70 (d, 2H, J=7.8 Hz), 7.40 (m, 3H), 7.22-6.83 (m, 5H), 5.31 (s, 2H), 4.87 (m, 1H), 4.13 (s, 3H), 4.00 (s, 3H), 3.90 (br, 4H), 3.01 (t, J=5.7 Hz, 2H), 2.62 (m, 1H), 2.41 (s, 3H), 2.26-1.81 (m, 8H).

MS (m/z)=616.31 [M+H].

HCK IC50 (nM); 4.9, FLT3-ITD IC50 (nM); 3999.9

Example 17

RK-0020732

N-(4-(4-amino-7-((trans)-4-(4-methylpiperazin-1-yl)cyclohexyl)-7H-pyrrolo[2,3-d]pyrimidin-5-yl)phenyl)-1-methyl-1H-indole-2-carboxamide

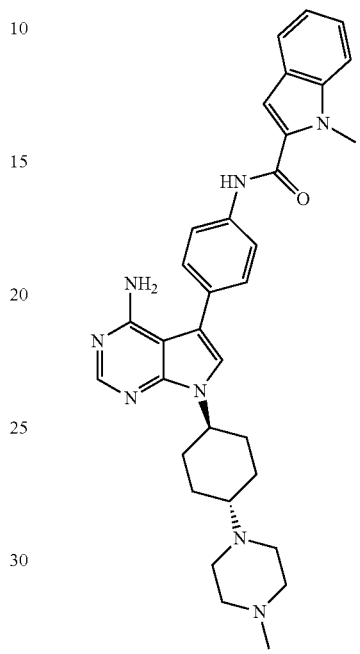

(1) tert-Butyl (4-(4-amino-7-((trans)-4-(4-methylpiperazin-1-yl)cyclohexyl)-7H-pyrrolo[2,3-d]pyrimidin-5-yl)phenyl)carbamate tert-Butyl (4-(4,4,5,5-tetramethyl-1,3,2-dioxaborolan-2-yl)phenyl)carbamate (4.6 g, 10.45 mmol) was dissolved in ethylene glycol dimethyl ether (50 mL) and ethanol (30 mL), and 5-iodo-7-((trans)-4-(4-methylpiperazin-1-yl)cyclohexyl)-7H-pyrrolo[2,3-d]pyrimidin-4-amine (4.6 g, 10.5 mmol), a saturated sodium carbonate solution (20 mL) and tetrakis(triphenylphosphine)palladium (0.8 g, 73 mmol) were sequentially added to the solution. The mixture was stirred overnight in an argon atmosphere at 80° C. After the mixture was left to cool naturally, dichloromethane was added thereto, and the mixture was partitioned and washed with saturated brine. The organic layer was dried over anhydrous sodium sulfate, and then the solvent was distilled off under reduced pressure. An oily substance thus obtained was purified by silica gel column chromatography (dichloromethane/methanol/28% aqueous ammonia=100/10/2), and thus the title compound (4.4 g) was obtained.

(2) Synthesis of 5-(4-aminophenyl)-7-((trans)-4-(4-methylpiperazin-1-yl)cyclohexyl)-7H-pyrrolo[2,3-d]pyrimidin-4-amine tert-Butyl (4-(4-amino-7-((trans)-4-(4-methylpiperazin-1-yl)cyclohexyl)-7H-pyrrolo[2,3-d]pyrimidin-5-yl)phenyl)carbamate (4.4 g, 8.7 mmol) was dissolved in acetone (20 mL), and 5 M hydrochloric acid (5 mL) and TFA (1 mL) were added thereto. The mixture was heated to reflux for 2 hours. The mixture was adjusted to pH 9 with a 2 M sodium hydroxide solution, and the mixture was concentrated under reduced pressure. Subsequently, ethyl acetate was added thereto, and the mixture was partitioned and washed with saturated brine. The organic layer was dried over anhydrous sodium sulfate, and then the solvent was distilled off under reduced pressure. Thus, the title compound (3.1 g) was obtained. This was used in the subsequent reaction without being purified.

(3) N-(4-(4-amino-7-((trans)-4-(4-methylpiperazin-1-yl)cyclohexyl)-7H-pyrrolo[2,3-d]pyrimidin-5-yl)phenyl)-1-methyl-1H-indole-2-carboxamide 5-(4-Aminophenyl)-7-((trans)-4-(4-methylpiperazin-1-yl)cyclohexyl)-7H-pyrrolo[2,3-d]pyrimidin-4-amine (0.1 g, 0.25 mmol), 1-methyl-1H-indole-2-carboxylic acid (45 mg, 0.259 mmol), and TBTU (83 mg, 0.259 mmol) were dissolved in DMF (6 mL), and DIPEA (48 mg, 0.37 mmol) was added dropwise thereto. This solution was stirred overnight at room temperature, and was concentrated under reduced pressure. Subsequently, an oily substance thus obtained was purified by silica gel column chromatography (dichloromethane/methanol/28% aqueous ammonia=100/10/2), and was further purified by preparative thin layer chromatography (dichloromethane/methanol=10/1). Thus, the title compound (pale brown solid, 45 mg) was obtained.

$^1$H NMR (270 MHz, CDCl$_3$, δ): 8.32 (s, 1H), 8.10 (s, 1H), 7.77-7.65 (m, 3H), 7.53-7.33 (m, 4H), 7.24-7.15 (m, 1H), 7.04 (d, J=8.6 Hz, 2H), 5.15 (s, 2H), 4.77-4.60 (m, 1H), 4.11 (s, 3H), 2.74-2.57 (m, 4H), 2.57-2.35 (m, 5H), 2.30 (s, 3H), 2.27-2.15 (m, 2H), 2.15-2.00 (m, 2H), 1.90-1.70 (m, 2H), 1.70-1.50 (m, 2H).

MS (m/z)=563.60 [M+H].

HCK IC50 (nM); 2.55, FLT3-ITD IC50 (nM); 255

Example 18

RK-0020746

N-((trans)-4-(4-amino-5-(4-phenoxyphenyl)-7H-pyrrolo[2,3-d]pyrimidin-7-yl)cyclohexyl)picolinamide

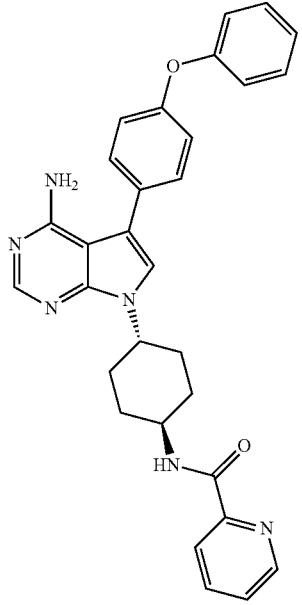 [SMILES: Nc1ncnc2c1c(-c1ccc(Oc3ccccc3)cc1)cn2[C@H]1CC[C@H](NC(=O)c2ccccn2)CC1]

The title compound (pale brownish-red oily substance) was synthesized according to the synthesis method of Example 12, by using pyridine-2-carboxylic acid instead of isonicotinic acid in step (2).

$^1$H NMR (270 MHz, CDCl$_3$, δ): 8.59 (d, J=1.1 Hz, 1H), 8.43 (br, 1H), 8.35 (s, 1H), 8.23 (d, J=7.8 Hz, 2H), 7.87 (t, J=7.5 Hz, 1H), 7.38-7.35 (m, 5H), 7.18-7.06 (6H, m), 5.13 (s, 2H), 4.82 (m, 1H), 4.40 (m, 1H), 2.22-2.00 (m, 8H).

MS (m/z)=505.23 [M+H].

HCK IC50 (nM); 4.55, FLT3-ITD IC50 (nM); 428

Example 19

RK-0020755

N-((trans)-4-(4-amino-5-(4-phenoxyphenyl)-7H-pyrrolo[2,3-d]pyrimidin-7-yl)cyclohexyl)nicotinamide

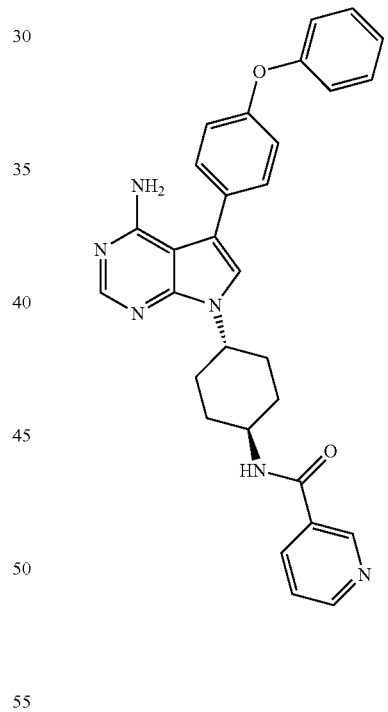

The title compound (white solid) was synthesized according to the synthesis method of Example 12, by using nicotinic acid instead of isonicotinic acid in step (2).

$^1$H NMR (270 MHz, CDCl$_3$, δ): 9.10 (d, J=1.3 Hz, 1H), 8.77 (dd, J=1.6, 3.5 Hz, 1H), 8.24 (s, 1H), 8.23 (dt, J=1.6, 8.1 Hz, 1H), 7.46-7.35 (m, 5H), 7.18-7.12 (5H, m), 7.00 (s, 1H), 6.66 (d, J=8.1 Hz, 1H), 5.13 (s, 2H), 4.63 (m, 1H), 4.51 (m, 1H), 2.32-1.68 (m, 8H).

MS (m/z)=505.23 [M+H].

HCK IC50 (nM); 11.85, FLT3-ITD IC50 (nM); 108

Example 20

RK-0020768

N-((trans)-4-(4-amino-3-(4-phenoxyphenyl)-1H-pyrazolo[3,4-d]pyrimidin-1-yl)cyclohexyl)isonicotinamide

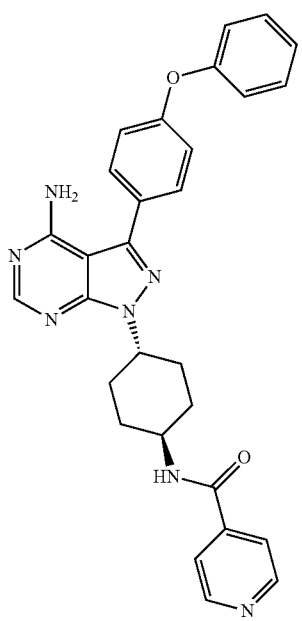 [SMILES: Nc1ncnc2c1c(-c1ccc(Oc3ccccc3)cc1)nn2[C@H]1CC[C@H](NC(=O)c2ccncc2)CC1]

The title compound (white solid) was synthesized according to the synthesis method of Example 12, by using 4-(4-amino-3-(4-phenoxyphenyl)-1H-pyrazolo[3,4-d]pyrimidin-1-yl)cyclohexanone instead of 4-(4-amino-5-(4-phenoxyphenyl)-7H-pyrrolo[2,3-d]pyrimidin-7-yl)cyclohexanone in step (1).

$^1$H NMR (270 MHz, CDCl$_3$, δ): 8.76 (d, J=5.9 Hz, 2H), 8.39 (s, 1H), 7.69-7.61 (m, 4H), 7.43-7.37 (m, 2H), 7.20-7.07 (m, 5H), 6.03 (d, J=8.1 Hz, 1H) 5.45 (s, 2H), 4.83 (m, 1H), 4.19 (m, 1H), 2.39-2.18 (m, 4H), 2.15 (m, 2H), 1.52 (m, 2H).

MS (m/z)=506.22 [M+H].

HCK IC50 (nM); 7.9, FLT3-ITD IC50 (nM); 414

Example 21

RK-0020770

N-(4-(4-amino-1-((1r,4r)-4-(8-methyl-3,8-diazabicyclo[3.2.1]octan-3-yl)cyclohexyl)-1H-pyrazolo[3,4-d]pyrimidin-3-yl)phenyl)picolinamide

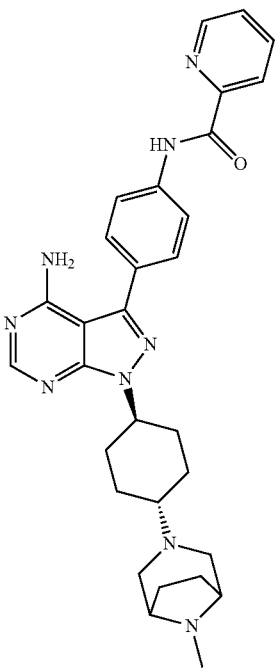 [SMILES: CN1C2CCC1CN([C@H]1CC[C@H](n3nc(-c4ccc(NC(=O)c5ccccn5)cc4)c4c(N)ncnc43)CC1)C2]

(1) N-(4-(4,4,5,5-tetramethyl-1,3,2-dioxaborolan-2-yl)phenyl)picolinamide 4-(4,4,5,5-Tetramethyl-1,3,2-dioxaborolan-2-yl)aniline (3.00 g, 13.7 mmol), 2-picolinic acid (1.70 g, 13.7 mmol), and TBTU (4.40 g, 13.7 mmol) were dissolved in DMF (20 mL), and DIPEA (1.77 g, 13.7 mmol) was added dropwise thereto. This solution was stirred for 3 hours at room temperature, water was added thereto, and the mixture was extracted with ethyl acetate. The extract was further washed with water and then dried over anhydrous sodium sulfate, and the solvent was distilled off under reduced pressure. A solid thus obtained was washed with IPE, and thus the title compound (white solid, 3.7 g) was obtained.

$^1$H NMR (270 MHz, CDCl$_3$, δ): 10.11 (br, 1H), 8.65-8.59 (m, 1H), 8.33-8.27 (m, 1H), 7.91 (dt, J=1.6, 7.5 Hz, 1H), 7.87-7.78 (m, 4H), 7.52-7.45 (m, 1H), 1.35 (s, 12H).

MS (m/z)=325.30 [M+H].

(2) 3-iodo-1-((1r,4r)-4-(8-methyl-3,8-diazabicyclo[3.2.1]octan-3-yl)cyclohexyl)-1H-pyrazolo[3,4-d]pyrimidin-4-amine Methanol (115 mL) and acetic acid (11.5 mL) were added to 4-(4-amino-3-iodo-1H-pyrazolo[3,4-d]pyrimidin-1-yl)

cyclohexanone (17.0 g, 47.6 mmol) and 8-methyl-3,8-diazabicyclo[3.2.1]octane dihydrochloride (9.5 g, 47.6 mmol), and the mixture was stirred at 90° C. 2-Picoline-borane complex (5.1 g, 47.6 mmol) was added thereto over 40 minutes. Methanol (30 mL) was added thereto, and the mixture was stirred for 2 hours at room temperature. Subsequently, the mixture was poured into a saturated solution of sodium hydrogen carbonate, and the mixture was extracted with chloroform/methanol (10/1). The organic layer was washed with saturated brine and dried over anhydrous sodium sulfate, and then the solvent was distilled off under reduced pressure. The residue was purified by aminopropyl silica gel chromatography (toluene/ethyl acetate=4/1), and thus the title compound (white solid, 5.6 g) was obtained.

$^{1}$H NMR (270 MHz, CD$_3$OD, δ): 8.17 (s, 1H), 4.67-4.51 (m, 1H), 3.11 (s, 2H), 2.70-2.51 (m, 4H), 2.28-2.44 (m, 1H), 2.25 (s, 3H), 2.12-1.86 (m, 8H), 1.86-1.74 (m, 2H), 1.59-1.37 (m, 2H).

MS (m/z)=510.50 [M+H].

(3) Synthesis of N-(4-(4-amino-1-((1r,4r)-4-(8-methyl-3,8-diazabicyclo[3.2.1]octan-3-yl)cyclohexyl)-1H-pyrazolo[3,4-d]pyrimidin-3-yl)phenyl)picolinamide 3-iodo-1-((1r,4r)-4-(8-methyl-3,8-diazabicyclo[3.2.1]octan-3-yl)cyclohexyl)-1H-pyrazolo[3,4-d]pyrimidin-4-amine (0.5 g, 1.1 mmol), N-(4-(4,4,5,5-tetramethyl-1,3,2-dioxaborolan-2-yl)phenyl)picolinamide (0.4 g, 1.2 mmol), a saturated sodium carbonate solution (10 mL), and tetrakis(triphenylphosphine)palladium (0.1 g, 0.11 mmol) were sequentially added, and the mixture was stirred overnight in an argon atmosphere at 80° C. After the mixture was left to cool naturally, dichloromethane was added thereto, and the mixture was washed with saturated brine. The organic layer was dried over anhydrous sodium sulfate, and the solvent was distilled off under reduced pressure. An oily substance thus obtained was purified by silica gel column chromatography (dichloromethane/methanol/28% aqueous ammonia=100/10/2), and thus the title compound (white solid, 278 mg) was obtained.

$^{1}$H NMR (270 MHz, CDCl$_3$, δ): 10.19 (s, 1H), 8.67-8.63 (m, 1H), 8.37 (s, 1H), 8.36-8.30 (m, 1H), 8.00-7.90 (m, 3H), 7.76-7.69 (m, 2H), 7.56-7.49 (m, 1H), 5.50 (s, 2H), 4.81-4.65 (m, 1H), 3.08 (s, 2H), 2.57 (d, J=1.9 Hz, 4H), 2.50-2.35 (m, 1H), 2.27 (s, 3H), 2.23-1.65 (m, 10H), 1.60-1.40 (m, 2H).

MS (m/z)=538.29 [M+H].

HCK IC50 (nM); 4.7, FLT3-ITD IC50 (nM); 1176, hERG inhibition (automated patch-clamp), 10 µM; 48%

Example 22

RK-0020775

N-((trans)-4-(4-amino-3-(4-phenoxyphenyl)-1H-pyrazolo[3,4-d]pyrimidin-1-yl)cyclohexyl)nicotinamide

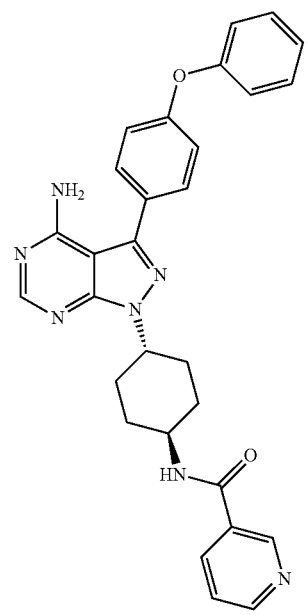

According to the synthesis method of Example 8, 1-(4-aminocyclohexyl)-3-(4-phenoxyphenyl)-1H-pyrazolo[3,4-d]pyrimidin-4-amine (100 mg), which was the product of step (4), nicotinic acid (43 mg, 0.33 mmol), and TBTU (84 mg, 0.26 mmol) were dissolved in DMF (3 mL), and DIPEA (49 mg, 0.38 mmol) was added dropwise thereto. This solution was stirred for one hour at room temperature and concentrated under reduced pressure, and then the concentrated solution was purified by preparative thin layer chromatography (dichloromethane/methanol/28% aqueous ammonia=100/10/2). Thus, N-((trans)-4-(4-amino-3-(4-phenoxyphenyl)-1H-pyrazolo[3,4-d]pyrimidin-1-yl)cyclohexyl)nicotinamide (white solid, 56 mg) was obtained.

$^{1}$H NMR (270 MHz, CDCl$_3$, δ): 8.98 (d, J=1.8 Hz, 1H), 8.74 (dd, J=1.6, 5.1 Hz, 1H), 8.39 (s, 1H), 8.13 (dt, J=8.1, 1.8 Hz, 1H,), 7.68 (m, 2H), 7.40-7.36 (m, 3H), 7.22-7.07 (m, 5H), 6.00 (d, J=8.1 Hz, 1H) 5.45 (s, 2H), 4.84 (m, 1H), 4.17 (m, 1H), 2.39 (m, 4H), 2.31 (m, 2H). 1.53 (m, 2H)

MS (m/z)=506.22 [M+H]

HCK IC50 (nM); 20, FLT3-ITD IC50 (nM); 190, hERG inhibition (automated patch-clamp), 10 µM; 50%

Example 23

RK-0020777

N-((trans)-4-(4-amino-3-(4-phenoxyphenyl)-1H-pyrazolo[3,4-d]pyrimidin-1-yl)cyclohexyl)picolinamide

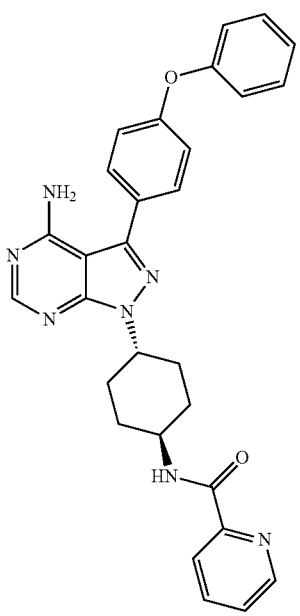

The title compound (white solid) was synthesized according to the synthesis method of Example 22, by using pyridine-2-carboxylic acid instead of nicotinic acid in the final step.

$^1$H NMR (270 MHz, CDCl$_3$, δ): 8.58 (d, J=4.0 Hz, 1H), 8.40 (s, 1H), 8.21 (d, J=8.1 Hz 1H), 7.88 (t, J=7.7 Hz, 1H), 7.67 (m, 2H), 7.46-7.37 (m, 3H), 7.22-7.08 (m, 5H), 5.41 (s, 2H), 4.91 (m, 1H), 4.40 (m, 1H), 2.42 (m, 2H), 2.22-2.01 (m, 6H).

MS (m/z)=506.22 [M+H].

HCK IC50 (nM); 12, FLT3-ITD IC50 (nM); 548

Example 24

RK-0020791

N-(4-(4-amino-1-((1r,4r)-4-(8-methyl-3,8-diazabicyclo[3.2.1]octan-3-yl)cyclohexyl)-1H-pyrazolo[3,4-d]pyrimidin-3-yl)phenyl)-1-methyl-1H-indole-2-carboxamide

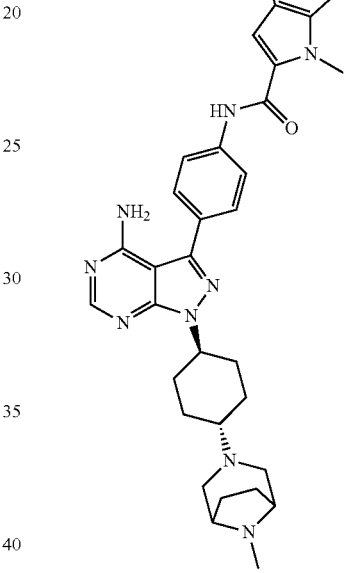

The title compound (white solid) was obtained according to the synthesis method of Example 21, by using 1-methyl-N-(4-(4,4,5,5-tetramethyl-1,3,2-dioxaborolan-2-yl)phenyl)-1H-indole-2-carboxamide instead of N-(4-(4,4,5,5-tetramethyl-1,3,2-dioxaborolan-2-yl)phenyl)picolinamide in step (3).

$^1$H NMR (270 MHz, CDCl$_3$, δ): 8.37 (s, 1H), 8.07 (s, 1H), 7.85-7.77 (m, 2H), 7.77-7.65 (m, 3H), 7.48-7.33 (m, 2H), 7.25-7.16 (m, 1H), 7.07 (s, 1H), 5.52 (s, 2H), 4.82-4.65 (m, 1H), 4.12 (s, 3H), 3.07 (s, 2H), 2.57 (d, J=1.9 Hz, 4H), 2.50-2.30 (m, 1H), 2.26 (s, 3H), 2.23-1.65 (m, 10H), 1.60-1.38 (m, 2H).

MS (m/z)=590.44 [M+H].

HCK IC50 (nM); 9.73, FLT3-ITD IC50 (nM); 3330, hERG inhibition (automated patch-clamp), 10 μM; 64%

Example 25

RK-0020798

N-(4-(4-amino-1-(1-(8-methyl-8-azabicyclo[3.2.1]octan-3-yl)piperidin-4-yl)-1H-pyrazolo[3,4-d]pyrimidin-3-yl)phenyl)-1-methyl-1H-indole-2-carboxamide

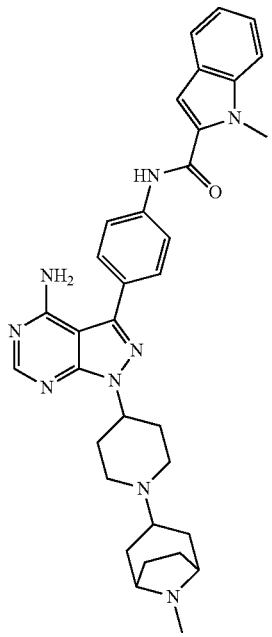 [SMILES: CN1C2CCC1CC(N1CCC(n3nc(-c4ccc(NC(=O)c5cc6ccccc6n5C)cc4)c4c(N)ncnc43)CC1)C2]

(1) tert-Butyl 4-(4-amino-3-iodo-1H-pyrazolo[3,4-d]pyrimidin-1-yl)piperidine-1-carboxylate Diisopropyl azodicarboxylate (5.8 g, 28.7 mmol) was added dropwise to a solution of triphenylphosphine (7.5 g, 28.7 mmol) in THF (70 mL) under ice cooling. The mixture was brought to room temperature, and 3-iodo-1H-pyrazolo[3,4-d]pyrimidin-4-amine (5.0 g, 19.2 mmol) and tert-butyl-4-hydroxypiperidine-1-carboxylate (5.8 g, 28.7 mmol) were added thereto. The mixture was stirred overnight at room temperature, and then was concentrated under reduced pressure. The residue was purified by silica gel column chromatography (dichloromethane/methanol=10/1), and thus the title compound (white solid, 3.8 g) was obtained.

(2) 3-iodo-1-(piperidin-4-yl)-1H-pyrazolo[3,4-d]pyrimidin-4-amine tert-Butyl 4-(4-amino-3-iodo-1H-pyrazolo[3,4-d]pyrimidin-1-yl)piperidine-1-carboxylate (3.8 g, 8.5 mmol) was dissolved in acetone/methanol (1/1, 30 mL), 5 M hydrochloric acid (14 mL) was added thereto, and the mixture was heated to reflux for 5 hours. The mixture was adjusted to pH 12 with a 2 M sodium hydroxide solution, concentrated under reduced pressure, and then washed with water. Thus, 3-iodo-1-(piperidin-4-yl)-1H-pyrazolo[3,4-d]pyrimidin-4-amine (3.0 g) was obtained.

(3) 3-iodo-1-(1-(8-methyl-8-azabicyclo[3.2.1]octan-3-yl)piperidin-4-yl)-1H-pyrazolo[3,4-d]pyrimidin-4-amine Tropinone (1.1 g, 7.67 mmol), 3-iodo-1-(piperidin-4-yl)-1H-pyrazolo[3,4-d]pyrimidin-4-amine (0.9 g, 2.56 mmol), and 2-picoline-borane complex (0.5 g, 3.84 mmol) were weighed in a microwavable pressure-resistant vessel, and 10% acetic acid/1,2-dichloroethane (10 mL) was added thereto. This mixture liquid was stirred in the microwave reactor for 7 minutes at 110° C. This reaction liquid was concentrated under reduced pressure, and then was purified by silica gel column chromatography (dichloromethane/methanol/28% aqueous ammonia=100/10/2). Thus, the title compound (0.4 g) was obtained.

(4) N-(4-(4-amino-1-(1-(8-methyl-8-azabicyclo[3.2.1]octan-3-yl)piperidin-4-yl)-1H-pyrazolo[3,4-d]pyrimidin-3-yl)phenyl)-1-methyl-1H-indole-2-carboxamide 3-iodo-1-(1-(8-methyl-8-azabicyclo[3.2.1]octan-3-yl)piperidin-4-yl)-1H-pyrazolo[3,4-d]pyrimidin-4-amine (0.2 g, 0.39 mmol) was dissolved in ethylene glycol dimethyl ether (4.2 mL) and ethanol (2.3 mL), and 1-methyl-N-(4-(4,4,5,5-tetramethyl-1,3,2-dioxaborolan-2-yl)phenyl)-1H-indole-2-carboxamide (0.2 g, 0.46 mmol), a saturated sodium carbonate solution (0.9 mL), and tetrakis(triphenylphosphine)palladium (31 mg, 0.03 mmol) were sequentially added thereto. The mixture was stirred all night and half a day in an argon atmosphere at 80° C. After the mixture was left to cool naturally, the mixture was extracted by adding ethyl acetate thereto, and the extract was partitioned and washed with saturated brine. The organic layer was dried over anhydrous sodium sulfate, and then the solvent was distilled off under reduced pressure. An oily substance thus obtained was isolated and purified by preparative thin layer chromatography (dichloromethane/methanol/28% aqueous ammonia=100/10/2), and thus the title compound (white solid, 35 mg) was obtained.

$^1$H NMR (270 MHz, CDCl$_3$, δ): 8.38 (s, 1H), 8.22 (s, 1H), 7.86-7.70 (m, 2H), 7.73-7.68 (m, 3H), 7.45-7.17 (m, 3H), 7.11 (s, 1H), 5.55 (s, 2H), 4.74 (m, 1H), 4.12 (s, 3H), 3.79 (s, 2H), 3.03 (br, 2H), 2.70 (s, 3H), 2.50-2.28 (m, 8H), 2.07-1.80 (m, 6H).

MS (m/z)=590.33 [M+H].

HCK IC50 (nM); 2.05, FLT3-ITD IC50 (nM); 2780, hERG inhibition (automated patch-clamp), 10 μM; 42%

Example 26

RK-0020819

N-(4-(4-amino-7-((cis)-4-(4-methylpiperazin-1-yl)cyclohexyl)-7H-pyrrolo[2,3-d]pyrimidin-5-yl)-2-methoxyphenyl)-1-methyl-1H-indole-2-carboxamide

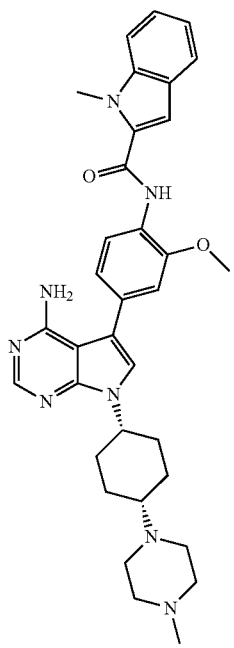 [SMILES: COc1cc(-c2cn([C@H]3CC[C@@H](N4CCN(C)CC4)CC3)c3ncnc(N)c23)ccc1NC(=O)c1cc2ccccc2n1C]

The title compound (white solid) was obtained according to the synthesis method of Example 4, by using N-methylpiperazine instead of 3-methyl-5,6,7,8-tetrahydro-[1,2,4]triazolo[4,3-a]pyrazine in step (4).

$^1$H NMR (270 MHz, CDCl$_3$, δ): 8.63 (s, 1H), 8.56 (d, J=8.4 Hz, 1H), 8.35 (s, 1H), 7.71 (d, J=7.8 Hz, 1H), 7.46-7.34 (m, 2H), 7.23-7.18 (m, 2H), 7.07 (s, 3H), 5.14 (s, 2H), 4.84 (m, 1H), 4.14 (s, 3H), 4.02 (s, 3H), 2.58 (br, 5H), 2.36 (s, 3H), 2.21 (m, 1H), 2.17-2.09 (m, 4H), 1.87-1.62 (m, 5H).

MS (m/z)=593.33 [M+H].

HCK IC50 (nM); 7.2, FLT3-ITD IC50 (nM); 1329

Example 27

RK-0020820

N-(4-(4-amino-7-((trans)-4-(4-methylpiperazin-1-yl)cyclohexyl)-7H-pyrrolo[2,3-d]pyrimidin-5-yl)-2-methoxyphenyl)-1-methyl-1H-indole-2-carboxamide

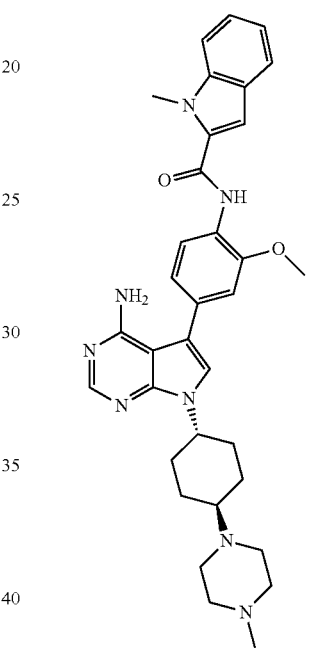

The title compound (white solid) was synthesized according to the synthesis method of Example 4, by using N-methylpiperazine instead of 3-methyl-5,6,7,8-tetrahydro-[1,2,4]triazolo[4,3-a]pyrazine in step (4).

$^1$H NMR (270 MHz, CDCl$_3$, δ): 8.62 (s, 1H), 8.55 (d, J=8.3 Hz, 1H), 8.34 (s, 1H), 7.71 (d, J=7.8 Hz, 1H), 7.43-7.37 (m, 2H), 7.25-7.04 (m, 5H), 5.18 (s, 2H), 4.70 (m, 1H), 4.14 (s, 3H), 4.00 (s, 3H), 2.67 (br, 3H), 2.50 (br, 3H), 2.32 (s, 3H), 2.25-2.08 (m, 4H), 1.87-1.58 (m, 6H).

MS (m/z)=593.33 [M+1].

HCK IC50 (nM); 1.6, FLT3-ITD IC50 (nM); 609, hERG inhibition (automated patch-clamp), 10 μM; 39.3%

Example 28

RK-0020824

N-(4-(4-amino-1-((trans)-4-(4-methylpiperazin-1-yl)cyclohexyl)-1H-pyrazolo[3,4-d]pyrimidin-3-yl)phenyl)-1-methyl-1H-indole-2-carboxamide

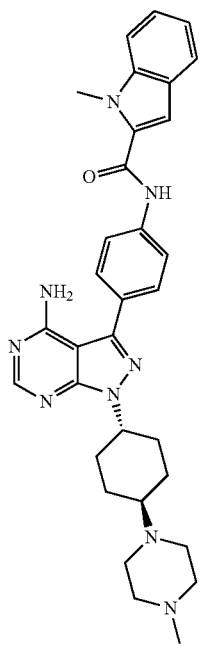 [SMILES: CN1CCN([C@H]2CC[C@H](n3nc(-c4ccc(NC(=O)c5cc6ccccc6n5C)cc4)c4c(N)ncnc43)CC2)CC1]

(1) N-(4-(4-amino-1-(4-oxocyclohexyl)-1H-pyrazolo[3,4-d]pyrimidin-3-yl)phenyl)-1-methyl-1H-indole-2-carboxamide 4-(4-Amino-3-iodo-1H-pyrazolo[3,4-d]pyrimidin-1-yl)cyclohexanone (0.2 g, 0.42 mmol) and 1-methyl-N-(4-(4,4,5,5-tetramethyl-1,3,2-dioxaborolan-2-yl)phenyl)-1H-indol-2-amine (0.2 g, 0.51 mmol) were dissolved in ethylene glycol dimethyl ether (4.9 mL) and ethanol (2.7 mL), and a saturated sodium carbonate solution (1.0 mL) and tetrakis(triphenylphosphine)palladium (34 mg, 0.03 mmol) were sequentially added to the solution. The mixture was stirred all night and half a day in an argon atmosphere at 80° C. After the mixture was left to cool naturally, the mixture was extracted by adding ethyl acetate thereto, and the extract was partitioned and washed with saturated brine. The organic layer was dried over anhydrous sodium sulfate, and then the solvent was distilled off under reduced pressure. An oily substance thus obtained was purified by silica gel column chromatography (dichloromethane/methanol=95/5), and thus N-(4-(4-amino-1-(4-oxocyclohexyl)-1H-pyrazolo[3,4-d]pyrimidin-3-yl)phenyl)-1-methyl-1H-indole-2-carboxamide (0.1 g) was obtained.

(2) N-(4-(4-amino-1-((trans)-4-(4-methylpiperazin-1-yl)cyclohexyl)-1H-pyrazolo[3,4-d]pyrimidin-3-yl)phenyl)-1-methyl-1H-indole-2-carboxamide N-(4-(4-amino-1-(4-oxocyclohexyl)-1H-pyrazolo[3,4-d]pyrimidin-3-yl)phenyl)-1-methyl-1H-indole-2-carboxamide (100 mg) was dissolved in 1,2-dichloroethane (3 mL), and acetic acid (35 mg, 0.59 mmol), N-methylpiperazine (59 mg, 0.59 mmol) and sodium triacetoxyborohydride (63 mg, 0.3 mmol) were added to the solution. The mixture was stirred overnight at room temperature. The reaction mixture was concentrated under reduced pressure and then was extracted with ethyl acetate, and the extract was partitioned and washed with water. The organic layer was dried over anhydrous sodium sulfate, and then the solvent was distilled off under reduced pressure. The residue was isolated and purified by preparative thin layer chromatography (dichloromethane/methanol/28% aqueous ammonia=100/10/2). Thus, N-(4-(4-amino-1-((cis)-4-(4-methylpiperazin-1-yl)cyclohexyl)-1H-pyrazolo[3,4-d]pyrimidin-3-yl)phenyl)-1-methyl-1H-indole-2-carboxamide (white solid, 39 mg) and the title compound N-(4-(4-amino-1-((trans)-4-(4-methylpiperazin-1-yl)cyclohexyl)-1H-pyrazolo[3,4-d]pyrimidin-3-yl)phenyl)-1-methyl-1H-indole-2-carboxamide (white solid, 12 mg) were obtained.

$^1$H NMR (270 MHz, CDCl$_3$, δ): 8.38 (s, 1H), 8.02 (s, 1H), 7.92-7.65 (m, 4H), 7.46-7.36 (m, 2H), 7.23-7.18 (m, 1H), 7.08 (s, 1H), 5.44 (s, 2H), 4.76 (m, 1H), 4.13 (s, 3H), 2.92 (m, 1H), 2.94-2.52 (m, 8H), 2.29 (s, 3H), 2.14 (m, 6H), 1.55 (m, 2H).

MS (m/z)=564.31 [M+H].

HCK IC50 (nM); 1.6, FLT3-ITD IC50 (nM); 1079

Example 29

RK-0020826

N-(4-(4-amino-1-((trans)-4-(3-methyl-5,6-dihydro[1,2,4]triazolo[4,3-a]pyrazin-7(8H)-yl)cyclohexyl)-1H-pyrazolo[3,4-d]pyrimidin-3-yl)-2-methoxyphenyl)-1-methyl-1H-indole-2-carboxamide

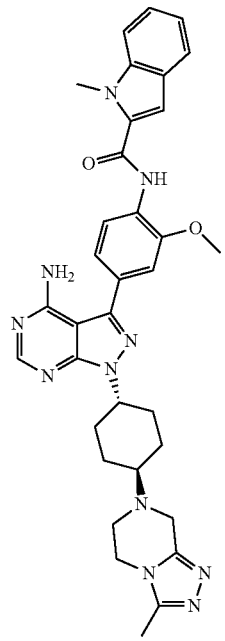

The title compound (white solid) was synthesized according to the synthesis method of Example 14, by using 3-methyl-5,6,7,8-tetrahydro-[1,2,4]triazolo[4,3-a]pyrazine instead of N-methylpiperazine in step (2).

$^1$H NMR (270 MHz, CDCl$_3$, δ): 8.68 (d, J=6.5 Hz, 1H), 8.64 (s, 1H), 8.39 (s, 1H), 7.71 (d, J=7.8 Hz, 1H), 7.46-7.29 (m, 4H), 7.23 (m, 1H), 7.10 (s, 1H), 5.61 (s, 2H), 4.86 (m, 1H), 4.14 (s, 3H), 4.05 (s, 3H), 3.99 (s, 2H), 3.85 (m, 2H), 3.04 (t, J=5.1 Hz, 2H), 2.43 (m, 3H), 2.41 (s, 3H), 2.31-2.11 (m, 6H), 1.63 (m, 2H).

HCK IC50 (nM); 1.8, FLT3-ITD IC50 (nM); 1343, hERG inhibition (automated patch-clamp), 10 μM; 17.1%

Example 30

RK-0020901

N-(4-(4-amino-7-((trans)-4-(3-(trifluoromethyl)-5,6-dihydro[1,2,4]triazolo[4,3-a]pyrazin-7(8H)-yl)cyclohexyl)-7H-pyrrolo[2,3-d]pyrimidin-5-yl)-2-methoxyphenyl)-1-methyl-1H-indole-2-carboxamide

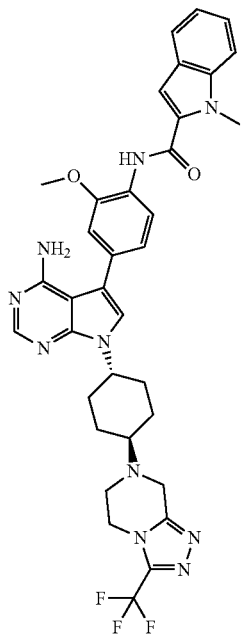 [SMILES: COc1cc(-c2cn([C@H]3CC[C@H](N4CCn5c(nnc5C(F)(F)F)C4)CC3)c3ncnc(N)c23)ccc1NC(=O)c1cc2ccccc2n1C]

The title compound (white solid) was synthesized according to the synthesis method of Example 4, by using 3-(trifluoromethyl)-5,6,7,8-tetrahydro-[1,2,4]triazolo[4,3-a]pyrazine instead of 3-methyl-5,6,7,8-tetrahydro-[1,2,4]triazolo[4,3-a]pyrazine in step (4).

$^1$H NMR (270 MHz, CDCl$_3$, δ): 8.62 (s, 1H), 8.57 (d, J=8.1 Hz, 1H), 8.35 (s, 1H), 7.70 (d, J=7.8 Hz, 1H), 7.43-7.38 (m, 2H), 7.20-7.12 (m, 2H), 7.07 (s, 1H), 7.05 (s, 1H), 5.54 (s, 2H), 4.74 (m, 1H), 4.18 (m, 2H), 4.16 (s, 3H), 4.14 (s, 2H), 4.01 (s, 3H), 3.08 (t, J=5.7 Hz, 2H), 2.79 (m, 1H), 2.32 (m, 2H), 2.15 (m, 2H), 1.96 (m, 2H), 1.66 (m, 2H).

MS (m/z)=685.29 [M+H].

HCK IC50 (nM); 7.7, FLT3-ITD IC50 (nM); 10999.9

Example 31

RK-0020908

N-(4-(4-amino-7-((cis)-4-(3-ethyl-5,6-dihydro[1,2,4]triazolo[4,3-a]pyrazin-7(8H)-yl)cyclohexyl)-7H-pyrrolo[2,3-d]pyrimidin-5-yl)-2-methoxyphenyl)-1-methyl-1H-indole-2-carboxamide

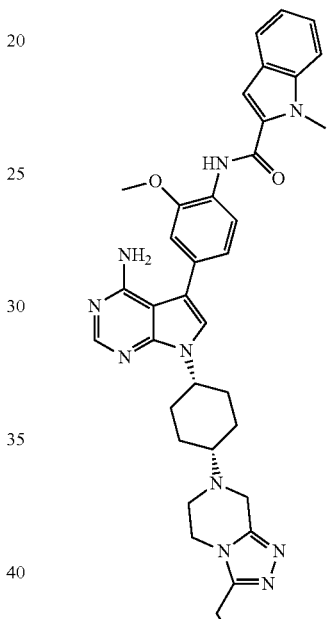

The title compound (white solid) was synthesized according to the synthesis method of Example 4, by using 3-ethyl-5,6,7,8-tetrahydro-[1,2,4]triazolo[4,3-a]pyrazine instead of 3-methyl-5,6,7,8-tetrahydro-[1,2,4]triazolo[4,3-a]pyrazine in step (4).

$^1$H NMR (270 MHz, CDCl$_3$, δ): 8.61 (s, 1H), 8.54 (d, J=8.4 Hz, 1H), 8.33 (s, 1H), 7.70 (d, J=7.8 Hz, 1H), 7.42-7.37 (m, 2H), 7.22-7.06 (m, 2H), 7.04 (s, 1H), 7.04 (s, 1H), 5.25 (s, 2H), 4.86 (m, 1H), 4.13 (s, 3H), 4.00 (s, 3H), 3.92 (s, 2H), 3.89 (m, 2H), 3.00 (br, 2H), 2.77 (q, J=7.6 Hz, 2H), 2.71 (m, 1H), 2.21-2.09 (m, 4H), 1.94-1.68 (m, 4H), 1.42 (m, 3H).

MS (m/z)=645.33 [M+H].

HCK IC50 (nM); 11, FLT3-ITD IC50 (nM); 10999.9

Example 32

RK-0020909

N-(4-(4-amino-7-((trans)-4-(3-ethyl-5,6-dihydro[1,2,4]triazolo[4,3-a]pyrazin-7(8H)-yl)cyclohexyl)-7H-pyrrolo[2,3-d]pyrimidin-5-yl)-2-methoxyphenyl)-1-methyl-1H-indole-2-carboxamide

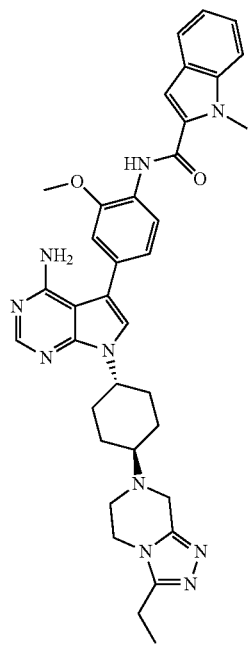 [SMILES: CCc1nnc2n1CCN([C@H]1CC[C@H](n3cc(-c4ccc(NC(=O)c5cc6ccccc6n5C)c(OC)c4)c4c(N)ncnc43)CC1)C2]

The title compound (white solid) was synthesized according to the synthesis method of Example 4, by using 3-ethyl-5,6,7,8-tetrahydro-[1,2,4]triazolo[4,3-a]pyrazine instead of 3-methyl-5,6,7,8-tetrahydro-[1,2,4]triazolo[4,3-a]pyrazine in step (4).

$^1$H NMR (270 MHz, CDCl$_3$, δ): 8.62 (s, 1H), 8.56 (d, J=8.1 Hz, 1H), 8.34 (s, 1H), 7.70 (d, J=7.8 Hz, 1H), 7.46-7.34 (m, 2H), 7.22-7.07 (m, 2H), 7.05 (s, 1H), 7.04 (s, 1H), 5.26 (s, 2H), 4.69 (m, 1H), 4.14 (s, 3H), 4.00 (s, 5H), 3.88 (t, J=5.4 Hz, 2H), 3.02 (t, J=5.4 Hz, 2H), 2.72 (q, J=7.6 Hz, 2H), 2.30 (m, 2H), 2.15 (m, 2H), 1.93-1.62 (m, 4H), 1.38 (m, 3H) MS (m/z)=645.33 [M+H].

HCK IC50 (nM); 14, FLT3-ITD IC50 (nM); 10999.9

Example 33

RK-0020918

N-(4-(4-amino-7-((cis)-4-(3-isopropyl-5,6-dihydro[1,2,4]triazolo[4,3-a]pyrazin-7(8H)-yl)cyclohexyl)-7H-pyrrolo[2,3-d]pyrimidin-5-yl)-2-methoxyphenyl)-1-methyl-1H-indole-2-carboxamide

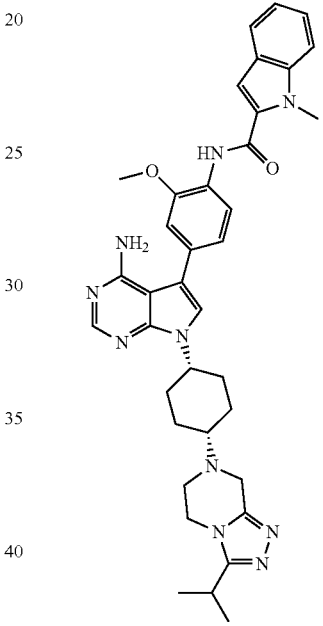

The title compound (white solid) was synthesized according to the synthesis method of Example 4, by using 3-isopropyl-5,6,7,8-tetrahydro-[1,2,4]triazolo[4,3-a]pyrazine instead of 3-methyl-5,6,7,8-tetrahydro-[1,2,4]triazolo[4,3-a]pyrazine in step (4).

$^1$H NMR (270 MHz, CDCl$_3$, δ): 8.62 (s, 1H), 8.55 (d, J=8.1 Hz, 1H), 8.32 (s, 1H), 7.70 (d, J=7.8 Hz, 1H), 7.45-7.34 (m, 2H), 7.22-7.03 (m, 5H), 5.49 (s, 2H), 4.74 (m, 1H), 4.13 (s, 3H), 4.01 (s, 3H), 3.94 (br, 4H), 3.01 (t, J=7.0 Hz, 2H), 2.62 (m, 1H), 2.26-1.81 (m, 8H), 1.43 (s, 3H), 1.40 (s, 3H).

MS (m/z)=659.35 [M+H].

HCK IC50 (nM); 7.7, FLT3-ITD IC50 (nM); 10999.9

Example 34

RK-0020919

N-(4-(4-amino-7-((trans)-4-(3-isopropyl-5,6-dihydro[1,2,4]triazolo[4,3-a]pyrazin-7(8H)-yl)cyclohexyl)-7H-pyrrolo[2,3-d]pyrimidin-5-yl)-2-methoxyphenyl)-1-methyl-1H-indole-2-carboxamide

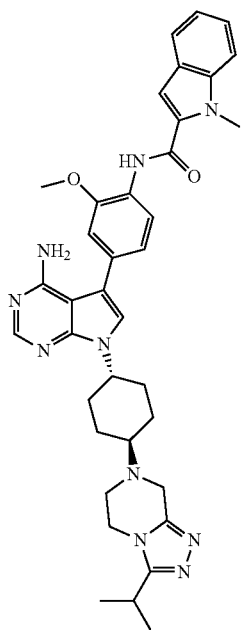 [SMILES: COc1cc(-c2cn([C@H]3CC[C@H](N4CCn5c(nnc5C(C)C)C4)CC3)c3ncnc(N)c23)ccc1NC(=O)c1cc2ccccc2n1C]

The title compound (white solid) was synthesized according to the synthesis method of Example 4, by using 3-isopropyl-5,6,7,8-tetrahydro-[1,2,4]triazolo[4,3-a]pyrazine instead of 3-methyl-5,6,7,8-tetrahydro-[1,2,4]triazolo[4,3-a]pyrazine in step (4).

$^1$H NMR (270 MHz, CDCl$_3$, δ): 8.62 (s, 1H), 8.56 (d, J=8.4 Hz, 1H), 8.34 (s, 1H), 7.71 (d, J=8.1 Hz, 1H), 7.46-7.34 (m, 2H), 7.23-6.87 (m, 5H), 5.26 (s, 2H), 4.73 (m, 1H), 4.14 (s, 3H), 4.01 (s, 5H), 3.92 (t, J=5.4 Hz, 2H), 2.99 (t, J=7.0 Hz, 2H), 2.75 (m, 1H), 2.30-2.15 (m, 4H), 1.99-1.66 (m, 4H), 1.41 (s, 3H), 1.39 (s, 3H).

MS (m/z)=659.35 [M+H].

HCK IC50 (nM); 7.7, FLT3-ITD IC50 (nM); 10999.9

Example 35

RK-0020920

N-(4-(4-amino-7-((cis)-4-(3-methyl-5,6-dihydroimidazolo[1,5-a]pyrazin-7(8H)-yl)cyclohexyl)-7H-pyrrolo[2,3-d]pyrimidin-5-yl)-2-methoxyphenyl)-1-methyl-1H-indole-2-carboxamide

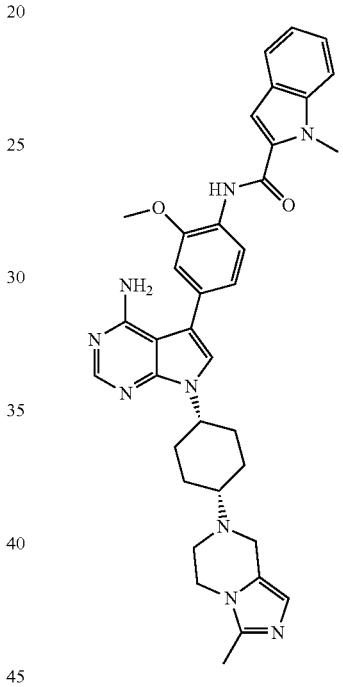

The title compound (white solid) was synthesized according to the synthesis method of Example 4, by using 3-methyl-5,6,7,8-tetrahydroimidazolo[1,5-a]pyrazine instead of 3-methyl-5,6,7,8-tetrahydro-[1,2,4]triazolo[4,3-a]pyrazine in step (4).

$^1$H NMR (270 MHz, CDCl$_3$, δ): 8.61 (s, 1H), 8.54 (d, J=8.1 Hz, 1H), 8.34 (s, 1H), 7.70 (d, J=8.1 Hz, 1H), 7.45-7.30 (m, 2H), 7.22-7.04 (m, 5H), 6.71 (s, 1H), 5.18 (s, 2H), 4.87 (m, 1H), 4.13 (s, 3H), 4.00 (s, 3H), 3.93 (t, J=5.6 Hz, 2H), 3.76 (s, 2H), 2.97 (t, J=5.7 Hz, 2H), 2.56 (m, 1H), 2.38 (s, 3H), 2.25-2.12 (m, 4H), 1.88-1.78 (m, 4H).

MS (m/z)=630.32 [M+H].

Example 36

RK-0020921

N-(4-(4-amino-7-((trans)-4-(3-methyl-5,6-dihydroimidazolo[1,5-a]pyrazin-7(8H)-yl)cyclohexyl)-7H-pyrrolo[2,3-d]pyrimidin-5-yl)-2-methoxyphenyl)-1-methyl-1H-indole-2-carboxamide

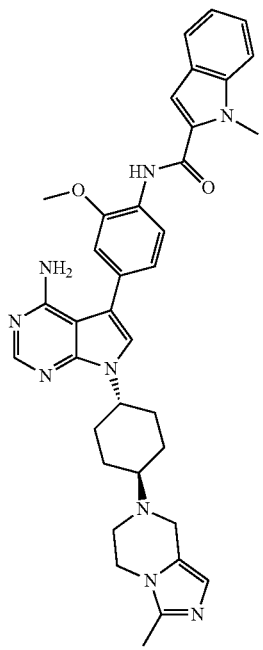 [SMILES: COc1cc(-c2cn([C@H]3CC[C@H](N4CCn5c(cnc5C)C4)CC3)c3ncnc(N)c23)ccc1NC(=O)c1cc2ccccc2n1C]

The title compound (white solid) was synthesized according to the synthesis method of Example 4, by using 3-methyl-5,6,7,8-tetrahydroimidazolo[1,5-a]pyrazine instead of 3-methyl-5,6,7,8-tetrahydro-[1,2,4]triazolo[4,3-a]pyrazine in step (4).

$^1$H NMR (270 MHz, CDCl$_3$, δ): 8.62 (s, 1H), 8.46 (d, J=7.8 Hz, 1H), 8.35 (s, 1H), 7.70 (d, J=8.1 Hz, 1H), 7.46-7.35 (m, 2H), 7.23-7.04 (m, 5H), 6.66 (s, 1H), 5.16 (s, 2H), 4.73 (m, 1H), 4.14 (s, 3H), 4.00 (s, 3H), 3.87 (m, 2H), 3.83 (s, 2H), 3.00 (t, J=5.4 Hz, 2H), 2.69 (m, 1H), 2.32 (s, 3H), 2.25-2.13 (m, 4H), 1.96-1.65 (m, 4H).

MS (m/z)=630.32 [M+H].

HCK IC50 (nM); 4, FLT3-ITD IC50 (nM); 409

Example 37

RK-0020930

N-(4-(4-amino-7-((cis)-4-(2-methyl-6,7-dihydropyrazolo[1,5-a]pyrazin-5(4H)-yl)cyclohexyl)-7H-pyrrolo[2,3-d]pyrimidin-5-yl)-2-methoxyphenyl)-1-methyl-1H-indole-2-carboxamide

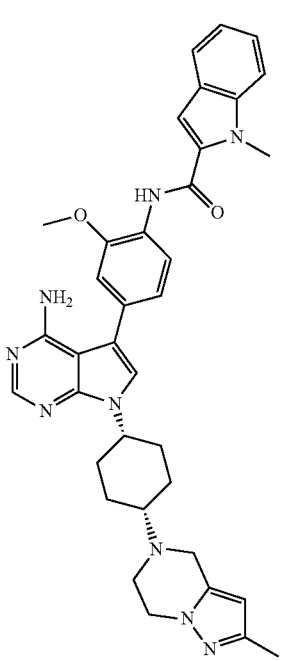 [SMILES: COc1cc(-c2cn([C@H]3CC[C@@H](N4CCn5nc(C)cc5C4)CC3)c3ncnc(N)c23)ccc1NC(=O)c1cc2ccccc2n1C]

The title compound (pale brown solid) was synthesized according to the synthesis method of Example 4, by using 2-methyl-4,5,6,7-tetrahydropyrazolo[1,5-a]pyrazine instead of 3-methyl-5,6,7,8-tetrahydro-[1,2,4]triazolo[4,3-a]pyrazine in step (4).

$^1$H NMR (270 MHz, CDCl$_3$, δ): 8.62 (s, 1H), 8.44 (d, J=8.4 Hz, 1H), 8.33 (s, 1H), 7.70 (d, J=7.8 Hz, 1H), 7.45-7.37 (m, 2H), 7.22-7.03 (m, 5H), 5.81 (s, 1H), 5.33 (s, 2H), 4.86 (m, 1H), 4.17 (t, J=5.4 Hz, 2H), 4.13 (s, 3H), 4.01 (s, 3H), 3.74 (s, 2H), 2.99 (t, J=5.7 Hz, 2H), 2.62 (m, 1H), 2.27 (s, 3H), 2.20-2.09 (m, 4H), 1.92-1.25 (m, 4H).

MS (m/z)=630.32 [M+H].

HCK IC50 (nM); 7.7, FLT3-ITD IC50 (nM); 3328

Example 38

RK-0020932

N-(4-(4-amino-7-((cis)-4-(6,7-dihydropyrazolo[1,5-a]pyrazin-5(4H)-yl)cyclohexyl)-7H-pyrrolo[2,3-d]pyrimidin-5-yl)-2-methoxyphenyl)-1-methyl-1H-indole-2-carboxamide

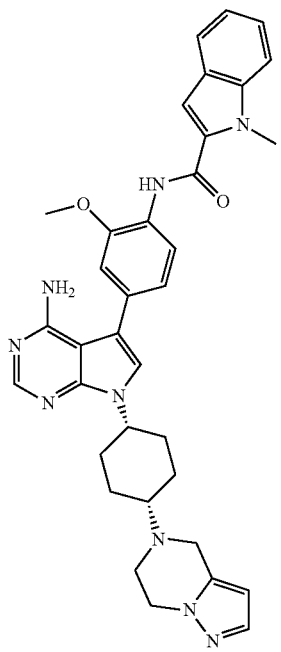 [SMILES: COc1cc(-c2cn([C@H]3CC[C@@H](N4CCn5nccc5C4)CC3)c3ncnc(N)c23)ccc1NC(=O)c1cc2ccccc2n1C]

The title compound (pale brown solid) was synthesized according to the synthesis method of Example 4, by using 4,5,6,7-tetrahydropyrazolo[1,5-a]pyrazine instead of 3-methyl-5,6,7,8-tetrahydro-[1,2,4]triazolo[4,3-a]pyrazine in step (4).

$^1$H NMR (270 MHz, CDCl$_3$, δ): 8.61 (s, 1H), 8.54 (d, J=7.8 Hz, 1H), 8.34 (s, 1H), 7.70 (d, J=8.1 Hz, 1H), 7.50-7.34 (m, 2H), 7.22-7.06 (m, 5H), 6.03 (s, 1H), 5.26 (s, 2H), 4.88 (m, 1H), 4.25 (t, J=4.1 Hz, 2H), 4.14 (s, 3H), 4.13 (s, 3H), 4.00 (s, 2H), 3.04 (t, J=4.6 Hz, 2H), 2.59 (m, 1H), 2.28-2.13 (m, 4H), 1.93-1.25 (m, 4H) MS (m/z)=616.31 [M+H].

HCK IC50 (nM); 2.8, FLT3-ITD IC50 (nM); 6581

Example 39

RK-0020942

N-(4-(4-amino-7-((trans)-4-(3-methyl-5,6-dihydroimidazo[1,2-a]pyrazin-7(8H)-yl)cyclohexyl)-7H-pyrrolo[2,3-d]pyrimidin-5-yl)-2-methoxyphenyl)-1-methyl-1H-indole-2-carboxamide

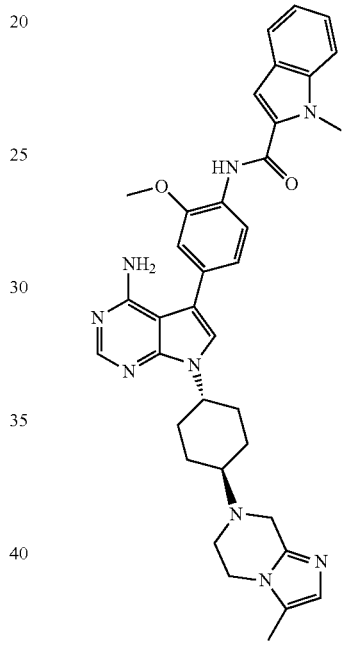

The title compound (white solid) was synthesized according to the synthesis method of Example 4, by using 3-methyl-5,6,7,8-tetrahydropyrazolo[1,2-a]pyrazine instead of 3-methyl-5,6,7,8-tetrahydro-[1,2,4]triazolo[4,3-a]pyrazine in step (4).

$^1$H NMR (270 MHz, CDCl$_3$, δ): 8.62 (s, 1H), 8.56 (d, J=8.1 Hz, 1H), 8.35 (s, 1H), 7.70 (d, J=7.8 Hz, 1H), 7.43-7.34 (m, 2H), 7.19-7.04 (m, 5H), 6.71 (s, 1H), 5.17 (s, 2H), 4.73 (m, 1H), 4.14 (s, 3H), 4.01 (s, 3H), 3.90 (s, 2H), 3.83 (t, J=4.9 Hz, 2H), 3.03 (t, J=5.4 Hz, 2H), 2.62 (m, 1H), 2.32 (m, 2H), 2.17 (s, 3H), 2.12 (m, 2H), 1.93-1.26 (m, 4H).

MS (m/z)=630.32 [M+H].

HCK IC50 (nM); 4, FLT3-ITD IC50 (nM); 4623

Example 40

RK-0020627

7-((trans)-4-(4-(2-Methoxyethyl)pyrazin-1-yl)cyclohexyl)-5-(4-phenoxyphenyl)-7H-pyrrolo[2,3-d]pyrimidin-4-amine

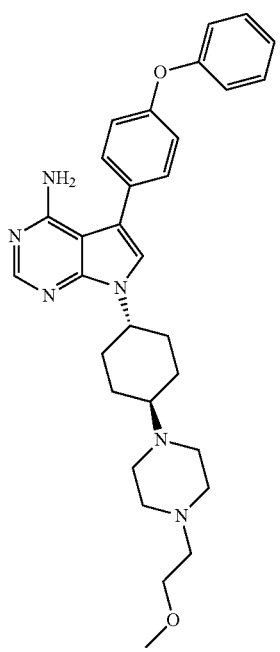 [SMILES: COCCN1CCN([C@H]2CC[C@H](n3cc(-c4ccc(Oc5ccccc5)cc4)c4c(N)ncnc43)CC2)CC1]

The title compound (white solid) was obtained according to the synthesis method of Example 1, by using 1-(2-methoxyethyl)piperazine instead of N-methylpiperazine in step (5).

$^1$H NMR (270 MHz, CDCl$_3$, δ): 8.33 (s, 1H), 7.45-7.35 (m, 5H), 7.15-7.06 (m, 4H), 7.01 (s, 1H), 5.06 (s, 2H), 4.70 (m, 1H), 3.52 (t, J=5.7 Hz, 2H), 3.36 (s, 3H), 2.68 (br, 4H), 2.60 (m, 6H), 2.17 (m, 2H), 2.05 (m, 2H), 1.79-1.59 (m, 4H).

MS (m/z)=527.31 [M+H].

HCK IC50 (nM); 4, FLT3-ITD IC50 (nM); 16, hERG inhibition (automated patch-clamp), 10 μM; 96%

Example 41

RK-0020629

2-(4-((trans)-4-(4-Amino-5-(4-phenoxyphenyl)-7H-pyrrolo[2,3-d]pyrimidin-7-yl)cyclohexyl) piperazin-1-yl)ethan-1-ol

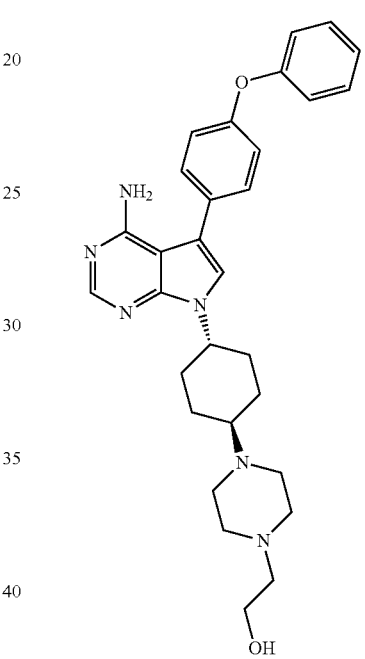

The title compound (white solid) was obtained according to the synthesis method of Example 1, by using 2-(piperazin-1-yl)ethanol instead of N-methylpiperazine in step (5).

$^1$H NMR (270 MHz, CDCl$_3$, δ): 8.33 (s, 1H), 7.65-7.35 (m, 4H), 7.18-7.06 (m, 5H), 7.01 (s, 1H), 5.08 (s, 2H), 4.69 (m, 1H), 3.63 (t, J=5.4 Hz, 2H), 2.58 (br, 8H), 2.56 (t, J=5.4 Hz, 2H), 2.45 (m, 1H), 2.24 (m, 2H), 2.10 (m, 2H), 1.84 (m, 2H), 1.62 (m, 2H).

MS (m/z)=513.29 [M+H].

HCK IC50 (nM); 3.5, FLT3-ITD IC50 (nM); 21, hERG inhibition (automated patch-clamp), 10 μM; 93%

Example 42

RK-0020640

7-((trans)-4-(4-Isopropylpiperazin-1-yl)cyclohexyl)-5-(4-phenoxyphenyl)-7H-pyrrolo[2,3-d]pyrimidin-4-amine

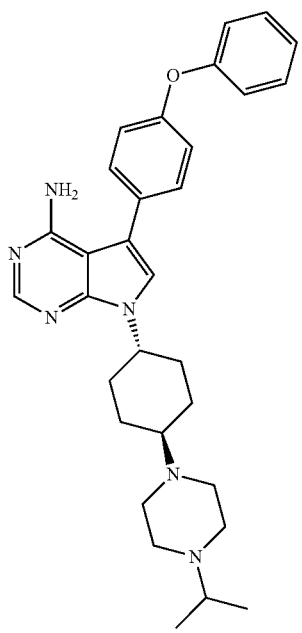 [SMILES: CC(C)N1CCN([C@H]2CC[C@H](n3cc(-c4ccc(Oc5ccccc5)cc4)c4c(N)ncnc43)CC2)CC1]

The title compound (white solid) was obtained according to the synthesis method of Example 1, by using 1-isopropylpiperazine instead of N-methylpiperazine in step (5)

$^1$H NMR (270 MHz, CDCl$_3$, δ): 8.33 (s, 1H), 7.65-7.31 (m, 4H), 7.18-7.01 (m, 5H), 6.87 (s, 1H), 5.06 (s, 2H), 4.68 (m, 1H), 2.62 (br, 8H), 2.45 (m, 1H), 2.24 (br, 2H), 2.19 (br, 2H), 1.83-1.58 (m, 4H), 1.09 (s, 3H), 1.07 (s, 3H).

MS (m/z)=510.31 [M+H].

HCK IC50 (nM); 0.26, FLT3-ITD IC50 (nM); 22, hERG inhibition (automated patch-clamp), 10 μM; 88%

Example 43

RK-0020658

5-(4-Phenoxyphenyl)-7-((trans)-4-(piperazin-1-yl)cyclohexyl)-7H-pyrrolo[2,3-d]pyrimidin-4-amine

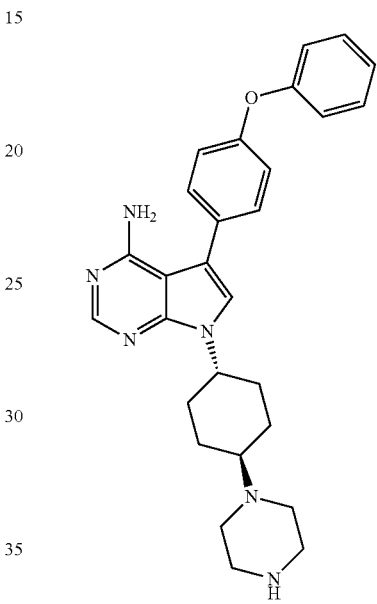

tert-Butyl 4-((trans)-4-(4-amino-5-(4-phenoxyphenyl)-7H-pyrrolo[2,3-d]pyrimidin-7-yl)cyclohexyl)piperazine-1-carboxylate was synthesized according to the synthesis method of Example 1, by using tert-butyl piperazine-1-carboxylate instead of N-methylpiperazine in step (5). Thereafter, 4 M hydrochloric acid-ethyl acetate (2 mL) was added thereto, and the mixture was stirred for one hour at room temperature. The mixture was adjusted to pH 9 with a 2 M sodium hydroxide solution. The organic layer was washed with water and saturated brine and dried over anhydrous sodium sulfate, and then the organic solvent was removed under reduced pressure. Thus, the title compound (white solid) was obtained.

$^1$H NMR (270 MHz, CDCl$_3$, δ): 8.33 (s, 1H), 7.45-7.35 (m, 4H), 7.15-7.06 (m, 5H), 7.01 (s, 1H), 5.06 (s, 2H), 4.66 (m, 1H), 2.93 (m, 4H), 2.59 (m, 4H), 2.44 (m, 1H), 2.39 (br, 2H), 2.09 (br, 2H), 1.84-1.61 (m, 4H).

MS (m/z)=469.26 [M+H].

HCK IC50 (nM); 2.8, FLT3-ITD IC50 (nM); 21.0

Example 44

RK-0020695

Synthesis of 5-(4-phenoxyphenyl)-7-((trans)-4-((pyridin-4-ylmethyl)amino)cyclohexyl)-7H-pyrrolo[2,3-d]pyrimidin-4-amine

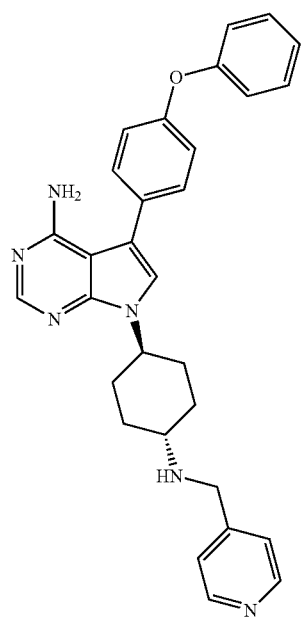 [SMILES: Nc1ncnc2c1c(-c1ccc(Oc3ccccc3)cc1)cn2[C@H]1CC[C@H](NCc2ccncc2)CC1]

The title compound (white solid) was obtained according to the synthesis method of Example 1, by using 4-picolylamine instead of N-methylpiperazine in step (5).

$^1$H NMR (270 MHz, CDCl$_3$, δ): 8.59-8.54 (m, 2H), 8.25 (s, 1H), 7.45-7.27 (m, 6H), 7.20-7.04 (m, 5H), 6.99 (s, 1H), 5.79 (br, 2H), 4.80-4.65 (m, 1H), 3.90 (s, 2H), 2.69-2.54 (m, 1H), 2.25-2.07 (m, 4H), 1.90-1.70 (m, 2H), 1.57-1.36 (m, 2H).

MS (m/z)=491.61 [M+H].

HCK IC50 (nM); 9, FLT3-ITD IC50 (nM); 15, hERG inhibition (automated patch-clamp), 10 µM; 93%

Example 45

RK-0020696

5-(4-Phenoxyphenyl)-7-((cis)-4-((pyridin-3-ylmethyl)amino)cyclohexyl)-7H-pyrrolo[2,3-d]pyrimidin-4-amine

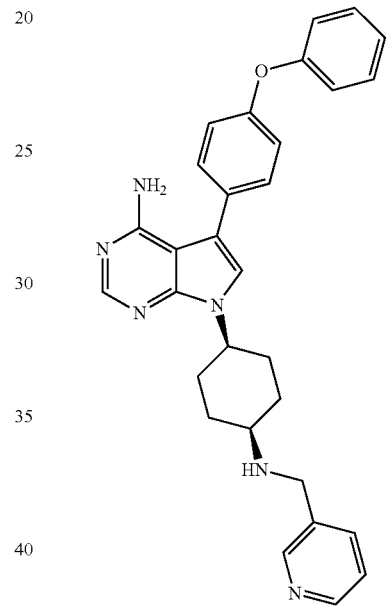

The title compound (white solid) was obtained according to the synthesis method of Example 1, by using 3-picolylamine instead of N-methylpiperazine in step (5).

$^1$H NMR (270 MHz, CDCl$_3$, δ): 8.63 (d, J=1.6 Hz, 1H), 8.52 (dd, J=4.9, 1.6 Hz, 1H), 8.22 (s, 1H), 7.80-7.68 (m, 1H), 7.57-7.25 (m, 6H), 7.20-7.03 (m, 5H), 6.10 (br, 2H), 4.81-4.72 (m, 1H), 3.83 (s, 2H), 3.02 (s, 1H), 2.30-1.70 (m, 8H).

MS (m/z)=491.60 [M+H].

HCK IC50 (nM); 0.9, FLT3-ITD IC50 (nM); 8.8, hERG inhibition (automated patch-clamp), 10 µM; 99%

Example 46

RK-0020697

5-(4-Phenoxyphenyl)-7-((trans)-4-((pyridin-4-ylmethyl)amino)cyclohexyl)-7H-pyrrolo[2,3-d]pyrimidin-4-amine

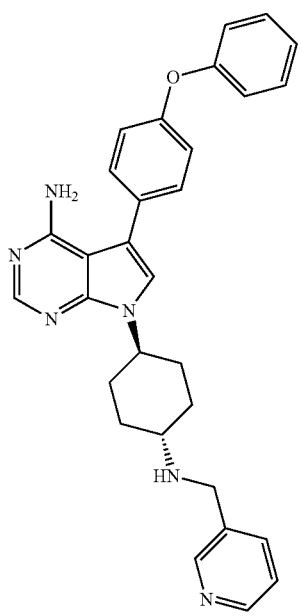 [SMILES: Nc1ncnc2c1c(-c1ccc(Oc3ccccc3)cc1)cn2[C@H]1CC[C@H](NCc2cccnc2)CC1]

The title compound (white solid) was obtained according to the synthesis method of Example 1, by using 3-picolylamine instead of N-methylpiperazine in step (5).

$^1$H NMR (270 MHz, CDCl$_3$, δ): 8.58 (d, J=1.9 Hz, 1H), 8.52 (dd, J=4.9, 1.9 Hz, 1H), 8.32 (s, 1H), 7.68-7.75 (m, 1H), 7.47-7.33 (m, 4H), 7.33-7.25 (m, 1H), 7.20-7.04 (m, 5H), 6.99 (s, 1H), 5.19 (s, 2H), 4.81-4.65 (m, 1H), 3.88 (s, 2H), 2.70-2.55 (m, 1H), 2.25-2.10 (m, 4H), 1.94-1.70 (m, 2H), 1.56-1.35 (m, 2H).

MS (m/z)=491.7 [M+H].

HCK IC50 (nM); 6.7, FLT3-ITD IC50 (nM); 11, hERG inhibition (automated patch-clamp), 10 μM; 92%

Example 47

RK-0020698

5-(4-Phenoxyphenyl)-7-((cis)-4-((pyridin-2-ylmethyl)amino)cyclohexyl)-7H-pyrrolo[2,3-d]pyrimidin-4-amine

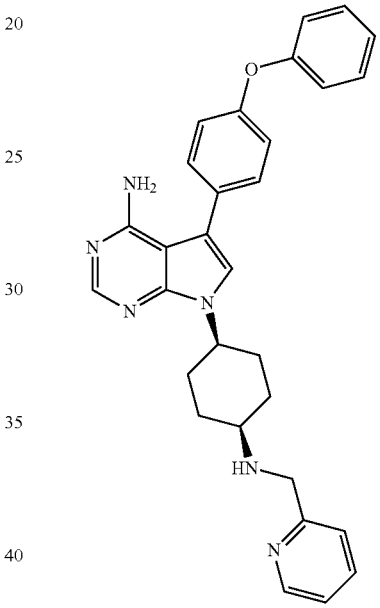

The title compound (white solid) was obtained according to the synthesis method of Example 1, by using 2-picolylamine instead of N-methylpiperazine in step (5).

$^1$H NMR (270 MHz, CDCl$_3$, δ): 8.62-8.54 (m, 1H), 8.29 (s, 1H), 7.66 (dt, J=1.9, 7.6 Hz, 1H), 7.47-7.29 (m, 5H), 7.23-7.03 (m, 7H), 5.50 (br, 2H), 4.84-4.68 (m, 1H), 3.94 (s, 2H), 3.05-2.97 (m, 1H), 2.34-2.13 (m, 2H), 2.10-1.70 (m, 6H).

MS (m/z)=491.41 [M+H].

HCK IC50 (nM); 6.5, FLT3-ITD IC50 (nM); 12, hERG inhibition (automated patch-clamp), 10 μM; 99%

Example 48

RK-0020703

5-(4-Phenoxyphenyl)-7-((cis)-4-((tetrahydro-2H-pyran-4-yl)amino)cyclohexyl)-7H-pyrrolo[2,3-d]pyrimidin-4-amine

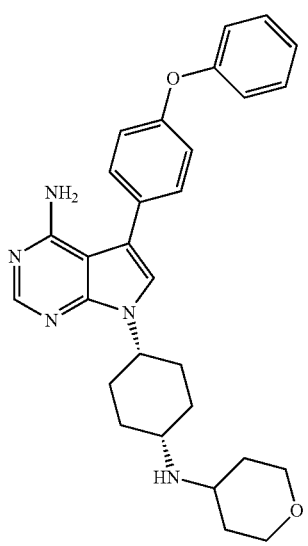 [SMILES: Nc1ncnc2c1c(-c1ccc(Oc3ccccc3)cc1)cn2[C@H]1CC[C@@H](NC2CCOCC2)CC1]

The title compound (yellow oily substance) was synthesized according to the synthesis method of example 1, by using tetrahydro-2H-pyran-4-amine instead of N-methylpiperazine in step (5).

$^1$H NMR (270 MHz, CDCl$_3$, δ): 8.33 (s, 1H), 7.47-7.35 (m, 4H), 7.15-6.87 (m, 6H), 5.13 (s, 2H), 4.74 (m, 1H), 3.99 (d, J=12.2 Hz, 2H), 3.41 (t, J=11.6 Hz, 2H), 3.15 (s, 1H), 2.76 (m, 1H), 2.17-2.10 (m, 2H), 1.89-1.77 (m, 6H), 1.53-1.26 (m, 4H).

MS (m/z)=484.26 [M+H].

HCK IC50 (nM); 8.2, FLT3-ITD IC50 (nM); 6.8, hERG inhibition (automated patch-clamp), 10 μM; 99%

Example 49

RK-0020710

7-((cis)-4-(((1-Methyl-1H-pyrazol-5-yl)methyl)amino)cyclohexyl)-5-(4-phenoxyphenyl)-7H-pyrrolo[2,3-d]pyrimidin-4-amine

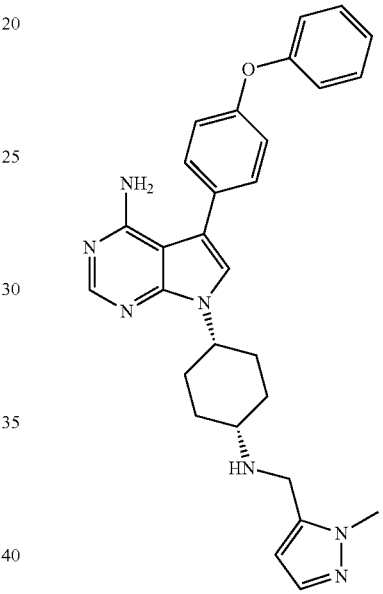

The title compound (white solid) was synthesized according to the synthesis method of Example 1, by using (1-methyl-1H-pyrazol-5-yl)methanamine instead of N-methylpiperazine in step (5).

$^1$H NMR (270 MHz, CDCl$_3$, δ): 8.34 (s, 1H), 7.65-7.31 (m, 4H), 7.18-7.05 (m, 6H), 6.17 (d, J=1.6 Hz, 2H), 5.09 (s, 2H), 4.79 (m, 1H), 3.93 (s, 3H), 3.80 (s, 2H), 3.02 (br, 1H), 2.14 (m, 2H), 1.91-1.79 (m, 7H).

MS (m/z)=494.26 [M+H].

HCK IC50 (nM); 0.53, FLT3-ITD IC50 (nM); 23, hERG inhibition (automated patch-clamp), 10 μM; 99%

Example 50

RK-0020711

7-((trans)-4-(((1-Methyl-1H-pyrazol-5-yl)methyl)amino)cyclohexyl)-5-(4-phenoxyphenyl)-7H-pyrrolo[2,3-d]pyrimidin-4-amine

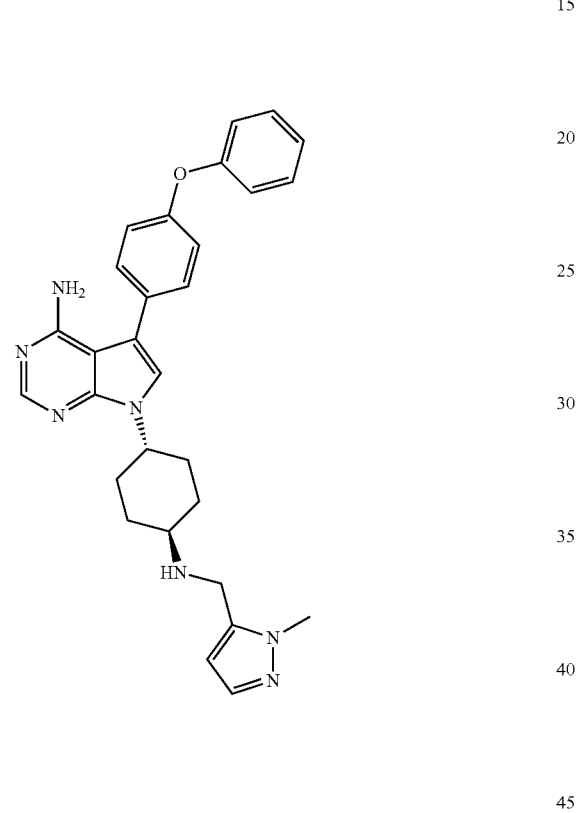

The title compound (white solid) was synthesized according to the synthesis method of Example 1, by using (1-methyl-1H-pyrazol-5-yl)methanamine instead of N-methylpiperazine in step (5).

$^1$H NMR (270 MHz, CDCl$_3$, δ): 8.33 (s, 1H), 7.65-7.31 (m, 4H), 7.19-7.06 (6H, m), 6.87 (s, 1H), 5.13 (s, 2H), 4.73 (m, 1H), 3.90 (s, 3H), 3.88 (s, 2H), 2.62 (m, 1H), 2.16 (m, 4H), 1.84 (m, 2H), 1.47 (m, 2H).

MS (m/z)=494.26 [M+H].

HCK IC50 (nM); 9.6, FLT3-ITD IC50 (nM); 39, hERG inhibition (automated patch-clamp), 10 μM; 97%

Example 51

RK-0020712

7-((cis)-4-(((1-Methyl-1H-pyrazol-3-yl)methyl)amino)cyclohexyl)-5-(4-phenoxyphenyl)-7H-pyrrolo[2,3-d]pyrimidin-4-amine

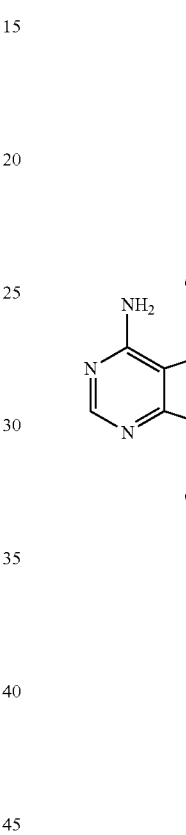

The title compound (white solid) was obtained according to the synthesis method of Example 1, by using (1-methyl-1H-pyrazol-3-yl)methanamine instead of N-methylpiperazine in step (5).

$^1$H NMR (270 MHz, CDCl$_3$, δ): 8.32 (s, 1H), 7.47-7.34 (m, 5H), 7.17-7.07 (6H, m), 6.19 (d, J=2.4 Hz, 1H), 5.11 (s, 2H), 4.77 (m, 1H), 3.88 (s, 3H), 3.81 (s, 2H), 3.03 (br, 1H), 2.18 (m, 2H), 2.15-1.76 (m, 7H).

MS (m/z)=494.26 [M+H].

HCK IC50 (nM); 8, FLT3-ITD IC50 (nM); 34, hERG inhibition (automated patch-clamp), 10 μM; 100%

Example 52

RK-0020724

1-((1s,4s)-4-(8-Methyl-3,8-diazabicyclo[3.2.1]octan-3-yl)cyclohexyl)-3-(4-phenoxyphenyl)-1H-pyrazolo[3,4-d]pyrimidin-4-amine

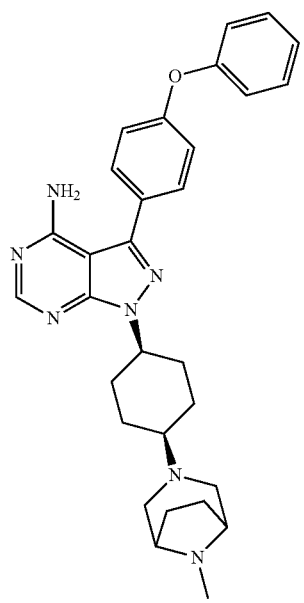 [SMILES: CN1C2CCC1CN([C@H]1CC[C@@H](n3nc(-c4ccc(Oc5ccccc5)cc4)c4c(N)ncnc43)CC1)C2]

The title compound (yellow solid) was obtained according to the synthesis method of Example 15.

$^1$H NMR (270 MHz, CDCl$_3$, δ): 8.35 (s, 1H), 7.74-7.64 (m, 2H), 7.44-7.34 (m, 2H), 7.05-7.22 (m, 5H), 5.72 (br, 2H), 4.92-4.70 (m, 1H), 3.11 (s, 2H), 2.78 (dd, J=2.7, 10.5 Hz, 2H), 2.60-2.40 (m, 2H), 2.30-2.20 (m, 7H), 2.16-2.05 (m, 2H), 2.00-1.86 (m, 3H), 1.83-1.70 (m, 2H), 1.62-1.42 (m, 2H).

MS (m/z)=510.48 [M+H].

HCK IC50 (nM); 14.5, FLT3-ITD IC50 (nM); 27, hERG inhibition (automated patch-clamp), 10 μM; 99%

Example 53

RK-0020733

(S)-3-(((cis)-4-(4-amino-5-(4-phenoxyphenyl)-7H-pyrrolo[2,3-d]pyrimidin-7-yl)cyclohexyl)amino)pyrrolidin-2-one

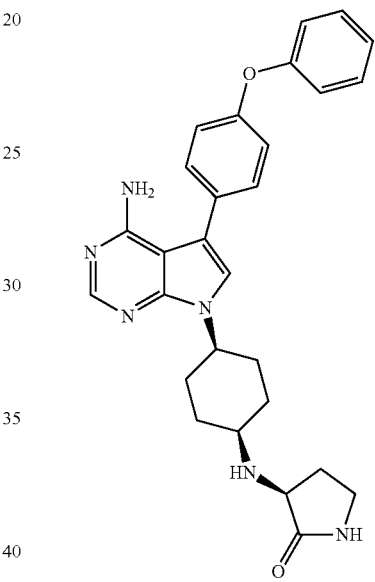

The title compound (white solid) was obtained according to the synthesis method of Example 1, by using (S)-3-aminopyrrolidin-2-one instead of N-methylpiperazine in step (5).

$^1$H NMR (270 MHz, CDCl$_3$, δ): 8.31 (s, 1H), 7.48-7.32 (m, 4H), 7.18-7.03 (m, 6H), 6.21 (s, 1H), 5.23 (s, 2H), 4.84-4.68 (m, 1H), 3.50-3.25 (m, 3H), 3.06 (s, 1H), 2.54-2.40 (m, 1H), 2.27-1.70 (m, 9H).

MS (m/z)=483.45 [M+H].

HCK IC50 (nM); 5.3, FLT3-ITD IC50 (nM); 30, hERG inhibition (automated patch-clamp), 10 μM; 97%

Example 54

RK-0020734

(S)-3-(((trans)-4-(4-amino-5-(4-phenoxyphenyl)-7H-pyrrolo[2,3-d]pyrimidin-7-yl)cyclohexyl)amino)pyrrolidin-2-one

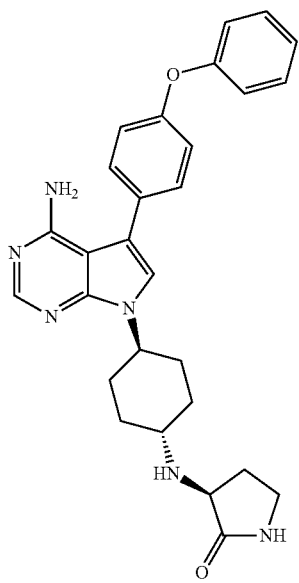 [SMILES: Nc1ncnc2c1c(-c1ccc(Oc3ccccc3)cc1)cn2[C@H]1CC[C@H](N[C@H]2CCNC2=O)CC1]

The title compound (white solid) was obtained according to the synthesis method of Example 1, by using (S)-3-aminopyrrolidin-2-one instead of N-methylpiperazine in step (5).

$^1$H NMR (270 MHz, CDCl$_3$, δ): 8.33 (s, 1H), 7.48-7.33 (m, 4H), 7.20-7.05 (m, 5H), 7.00 (s, 1H), 5.64 (s, 1H), 5.10 (s, 2H), 4.80-4.62 (m, 1H), 3.55-3.25 (m, 3H), 2.85-2.70 (m, 1H), 2.55-2.40 (m, 1H), 2.25-1.75 (m, 7H), 1.57-1.35 (m, 2H).

MS (m/z)=483.44 [M+H].

HCK IC50 (nM); 13.5, FLT3-ITD IC50 (nM); 25

Example 55

RK-0020758

7-((1s,4s)-4-((8-Methyl-8-azabicyclo[3.2.1]octan-3-yl)amino)cyclohexyl)-5-(4-phenoxyphenyl)-7H-pyrrolo[2,3-d]pyrimidin-4-amine

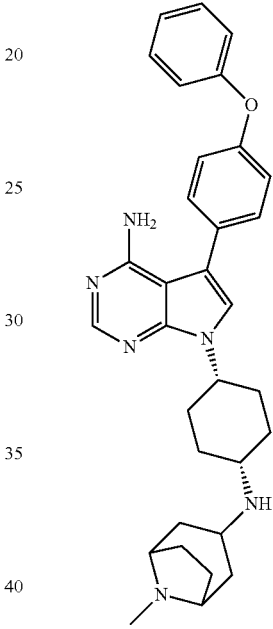

The title compound (white solid) was obtained according to the synthesis method of Example 1, by using 8-methyl-8-azabicyclo[3.2.1]octan-3-amine instead of N-methylpiperazine in step (5).

$^1$H NMR (270 MHz, CDCl$_3$, δ): 8.33 (s, 1H), 7.49-7.33 (m, 4H), 7.18-7.04 (m, 5H), 7.00 (s, 1H), 5.09 (s, 1H), 4.80-4.62 (m, 1H), 3.16-2.85 (m, 3H), 2.65-2.50 (m, 1H), 2.26 (s, 3H), 2.25-1.65 (m, 14H), 1.65-1.45 (m, 2H), 1.38-1.15 (m, 1H).

MS (m/z)=523.50 [M+H].

HCK IC50 (nM); 4.2, FLT3-ITD IC50 (nM); 35.2, hERG inhibition (automated patch-clamp), 10 μM; 92%

Example 56

RK-0020686

7-((trans)-4-(3-Methyl-5,6-dihydro[1,2,4]triazolo[4,3-a]pyrazin-7(8H)-yl)cyclohexyl)-5-(4-phenoxyphenyl)-7H-pyrrolo[2,3-d]pyrimidin-4-amine

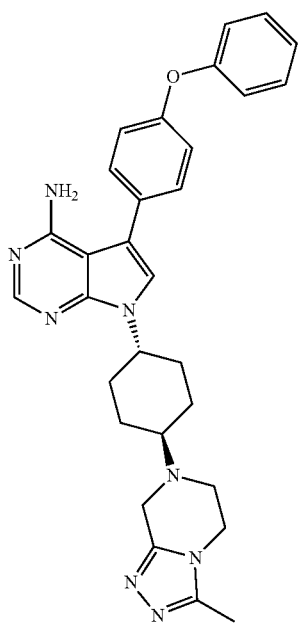 [SMILES: Cc1nnc2n1CCN([C@H]1CC[C@H](n3cc(-c4ccc(Oc5ccccc5)cc4)c4c(N)ncnc43)CC1)C2]

The title compound (white solid) was synthesized according to the synthesis method of Example 1, by using 1-(tert-butyl)piperazine instead of N-methylpiperazine in step (5).

$^1$H NMR (270 MHz, CDCl$_3$, δ): 8.33 (s, 1H), 7.45-7.36 (m, 4H), 7.18-7.06 (5H, m), 7.00 (s, 1H), 5.15 (s, 2H), 4.72 (m, 1H), 0.3.98 (s, 2H), 3.87 (t, J=5.4 Hz, 2H), 3.03 (t, J=5.3 Hz, 2H), 2.74 (m, 1H), 2.41 (s, 3H), 2.29 (br, 2H), 2.14 (br, 2H), 1.91-1.66 (m, 4H).

MS (m/z)=521.27 [M+H].

HCK IC50 (nM); 90, FLT3-ITD IC50 (nM); 23

Example 57

RK-0020693

N-(4-(4-amino-7-((trans)-4-(4-methylpiperazin-1-yl)cyclohexyl)-7H-pyrrolo[2,3-d]pyrimidin-5-yl)phenyl)-3-phenylpropanamide

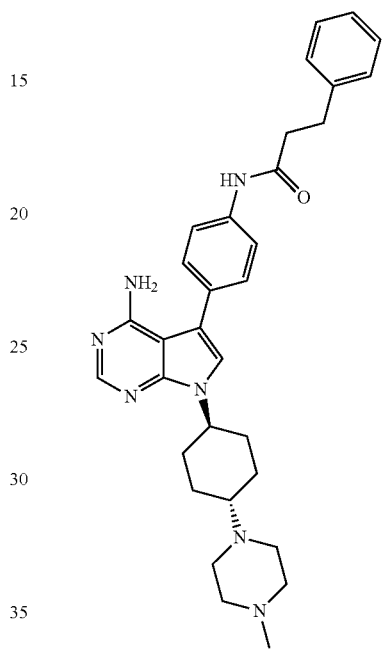

5-(4-Aminophenyl)-7-((trans)-4-(4-methylpiperazin-1-yl)cyclohexyl)-7H-pyrrolo[2,3-d]pyrimidin-4-amine (300 mg, 0.74 mmol) obtained in step (2) of Example 17 was dissolved in pyridine (5 mL), and while the mixture was stirred at room temperature, 3-phenylpropionic acid chloride (125 mg, 0.74 mmol) was added dropwise thereto. The mixture was allowed to react for 4 hours at room temperature, and then dichloromethane and water were added thereto. The mixture was adjusted to pH 9 by adding a 2 M sodium hydroxide solution, and the mixture was extracted with dichloromethane. Subsequently, the solvent was distilled off under reduced pressure. The residue thus obtained was purified by silica gel column chromatography (dichloromethane/methanol/28% aqueous ammonia=100/10/2), and was further purified by preparative thin layer chromatography (dichloromethane/methanol/28% aqueous ammonia=100/10/2). Thus, the title compound (white solid, 56 mg) was obtained.

$^1$H NMR (270 MHz, CDCl$_3$, δ): 8.32 (s, 1H), 7.56-7.46 (m, 2H), 7.46-7.37 (m, 2H), 7.37-7.20 (m, 5H), 7.06 (s, 1H), 6.99 (s, 1H), 5.03 (s, 2H), 4.76-4.60 (m, 1H), 3.09 (t, J=7.3 Hz, 2H), 2.75-2.57 (m, 7H), 2.57-2.36 (m, 4H), 2.30 (m, 3H), 2.26-2.14 (m, 2H), 2.14-2.02 (m, 2H), 1.92-1.70 (m, 2H), 1.70-1.50 (m, 2H).

MS (m/z)=538.70 [M+H].

HCK IC50 (nM); 32, FLT3-ITD IC50 (nM); 14, hERG inhibition (automated patch-clamp), 10 μM; 53%

Example 58

RK-0020898

5-(4-Phenoxyphenyl)-7-((trans)-4-(3-(trifluoromethyl)-5,6-dihydro[1,2,4]triazolo[4,3-a]pyrazin-7(8H)-yl)cyclohexyl)-7H-pyrrolo[2,3-d]pyrimidin-4-amine

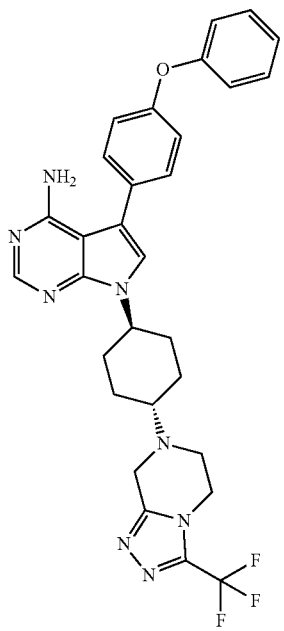 [SMILES: Nc1ncnc2c1c(-c1ccc(Oc3ccccc3)cc1)cn2[C@H]1CC[C@H](N2CCn3c(nnc3C(F)(F)F)C2)CC1]

The title compound was obtained as a white solid according to the synthesis method of Example 1, by using 3-(trifluoromethyl)-5,6,7,8-tetrahydro-[1,2,4]triazole[4,3-a]pyrazine hydrochloride instead of N-methylpiperazine in step (5).

$^1$H NMR (270 MHz, CDCl$_3$, δ): 8.33 (s, 1H), 7.47-7.34 (m, 4H), 7.20-7.05 (m, 5H), 7.00 (s, 1H), 5.14 (s, 2H), 4.80-4.65 (m, 1H), 4.16 (t, J=5.7 Hz, 2H), 4.08 (s, 2H), 3.08 (t, J=5.7 Hz, 2H), 2.84-2.70 (m, 1H), 2.35-1.60 (m, 8H).

MS (m/z)=575.50 [M+H].

HCK IC50 (nM); 23, FLT3-ITD IC50 (nM); 43

Example 59

RK-0020620

1-((trans)-4-(4-Methylpiperazin-1-yl)cyclohexyl)-3-(4-phenoxyphenyl)-1H-pyrazolo[3,4-d]pyrimidin-4-amine

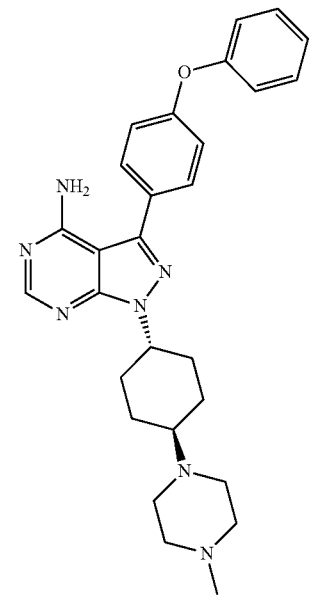 [SMILES: CN1CCN([C@H]2CC[C@H](n3nc(-c4ccc(Oc5ccccc5)cc4)c4c(N)ncnc43)CC2)CC1]

(1) 4-(4-Amino-3-(4-phenoxyphenyl)-1H-pyrazolo[3,4-d]pyrimidin-1-yl)cyclohexanone 4,4,5,5-Tetramethyl-2-(4-phenoxyphenyl)-1,3,2-dioxaborolane (1.0 g, 3.38 mmol) was dissolved in ethylene glycol dimethyl ether (38 mL) and ethanol (11 mL), and 4-(4-amino-3-iodo-1H-pyrazolo[3,4-d]pyrimidin-1-yl)cyclohexanone (0.5 g, 1.35 mmol), a saturated sodium carbonate solution (12 mL), and tetrakis(triphenylphosphine) palladium (0.1 g, 0.10 mmol) were sequentially added to the solution. The mixture was stirred all night and half a day in an argon atmosphere at 80° C. After the mixture was left to cool naturally, the mixture was extracted by adding dichloromethane thereto, and the extract was partitioned and washed with saturated brine. The organic layer was dried over anhydrous sodium sulfate, and then the solvent was distilled off under reduced pressure. An oily substance thus obtained was purified by silica gel column chromatography (dichloromethane/methanol=10/1→dichloromethane/methanol=95/5), and thus 4-(4-amino-3-(4-phenoxyphenyl)-1H-pyrazolo[3,4-d]pyrimidin-1-yl)cyclohexanone (0.7 g) was obtained.

(2) 1-((cis)-4-(4-Methylpiperazin-1-yl)cyclohexyl)-3-(4-phenoxyphenyl)-1H-pyrazolo[3,4-d]pyrimidin-4-amine and 1-((trans)-4-(4-methylpiperazin-1-yl)cyclohexyl)-3-(4-phenoxyphenyl)-1H-pyrazolo[3,4-d]pyrimidin-4-amine 4-(4-Amino-3-(4-phenoxyphenyl)-1H-pyrazolo[3,4-d]pyrimidin-1-yl)cyclohexanone (0.7 g, 1.65 mmol) was dissolved in 1,2-dichloroethane (20 mL), and acetic acid (0.3 g, 4.96 mmol), N-methylpiperazine (0.5 g, 4.96 mmol) and sodium triacetoxyborohydride (0.5 g, 2.48 mmol) were added to the solution. The mixture was stirred overnight at room temperature. The reaction mixture was concentrated under reduced pressure, and then was extracted with ethyl acetate. The extract was partitioned and washed with water. The organic layer was dried over anhydrous sodium sulfate, and then the solvent was distilled off under reduced pressure. The residue was isolated and purified by preparative thin layer chromatography (dichloromethane/methanol/28% aqueous ammonia=100/10/2). Thus, 1-((cis)-4-(4-methyl-piperazin-1-yl)cyclohexyl)-3-(4-phenoxyphenyl)-1H-pyrazolo[3,4-d]pyrimidin-4-amine (yellow oil, 194 mg) and 1-((trans)-4-(4-methylpiperazin-1-yl)cyclohexyl)-3-(4-phenoxyphenyl)-1H-pyrazolo[3,4-d]pyrimidin-4-amine (white solid, 73 mg) were obtained.

$^1$H NMR (270 MHz, CDCl$_3$, δ): 8.36 (s, 1H), 7.65 (d, J=6.5, 1H), 7.41-7.27 (m, 2H), 7.19-7.06 (m, 5H), 5.54 (s, 2H), 4.74 (m, 1H), 2.67 (br, 4H), 2.53 (br, 5H), 2.32 (s, 3H), 2.27-2.07 (br, 6H), 1.82 (br, 2H).

MS (m/z)=483.27 [M+1H]

HCK IC50 (nM); 3, FLT3-ITD IC50 (nM); 55

Example 60

Material and Methods (1) Human Samples

All experiments were conducted with the approval of the Institutional Review Board for Human Research of the RIKEN Research Center for Allergy and Immunology. All human samples were collected with informed consent in writing.

Transcription profiling were conducted on the bone marrow (BM) or the peripheral blood (PB) derived from 46 patients having subtype of French-American-British (FAB) classification system MO (N=1), M1 (N=5), M2 (N=9), M4 (N=4), M5 (N=1) and MDS/AML (N=25). The evaluations of HCK inhibition were conducted on the BM or PB derived from 32 patients. The cord blood (CB) samples were collected with informed consent in writing by Tokyo Cord Blood Bank Network. BM mononuclear cells (MNC) derived from normal donors were obtained from Cambrex (Walkerville, Md.). BM MNC and CB MNC derived from AML patients were isolated using density gradient centrifugation.

(2) Animals

NOD. Cg-Prkdc$^{scid}$ IL2rg$^{tmLWjL}$/Sz (NOD/SCID/IL2rg$^{null}$, NSG) mouse was developed at the Jackson Laboratory (Bar Harbor, Me.) by backcrossing a complete null mutation at the Il2rg locus onto the NOD.Cg-Prkdc.sup.scid (NOD/SCID) strain (Shultz, L. D. et al. Multiple defects in innate and adaptive immunologic function in NOD/LtSz-scid mice. J Immunol 154, 180-191 (1995)). Mice were bred and maintained under defined flora with irradiated food and acidified water at the animal facility of RIKEN and at The Jackson Laboratory according to guidelines established by the Institutional Animal Committees at the respective institutions.

(3) Flow Cytometry and Fluorescence Activated Cell Sorting (FACS)

For the evaluation of the engraftments of human cells and the marker expressions, the cells were labelled with fluorescent dye-coupled rat anti-mouse CD45, anti-mouse CD117, anti-mouse Sca-1, anti-mouse Gr1, anti-mouse CD11b, anti-mouse TER119, mouse anti-human CD45, anti-human CD33, anti-human CD34, anti-human CD38, anti-human CD3, anti-human CD8, anti-human CD19 monoclonal antibodies (BD Biosciences, San Jose, Calif.). The analysis was conducted with FACSAria and FASCCanto II (BD Biosciences, San Jose, Calif.). For obtaining the cells for the microarray analysis and xenografting, human MNC were labelled with fluorescent dye-coupled mouse anti-human CD3, anti-human CD4, anti-human CD8, anti-human CD34 and anti-human CD38 monoclonal antibodies (BD Biosciences, San Jose, Calif.), and BM MNC of the recipients were labelled with the aforementioned fluorescent dye-coupled mouse anti-human CD45, anti-human CD34 and anti-human CD38 monoclonal antibodies, and sorted using FACSAria (BD Biosciences, San Jose, Calif.). The purities of sorted cells were higher than 98%. For calculating the accurate number of the cells, the flow cytometry by AccuCount Beads (BD Biosciences, San Jose, Calif.) was conducted.

(4) Xenografting

Newborn NOD/SCID/IL2rg$^{null}$ recipients were received 150 cGy of total body irradiation, followed by intravenous injection of the sorted cells. As described in F. Ishikawa et al., Nat. Biotechnol. 25, 1315 (2007), for the production the AML grafted recipients, the 10$^3$-10$^5$ cells of the sorted BM cells of 7AAD$^-$ line (hCD3/hCD4/hCD8)$^-$ hCD34$^+$hCD38$^-$ AML patients per one recipients were used. The engraftments of the human peripheral blood (PB) cells were assessed by the retro-orbital phlebotomy.

(5) Microarray Analysis

74 LSC samples and 8 HSC samples derived from the normal BM were assessed using the microarray for human gene expression analysis, GeneChip™ Human Genome U133 Plus 2.0 Array (Affymetrix). Biotinylated cRNAs were synthesized using Two-Cycle Target Labeling Kit (Affymetrix) from the total RNA of over 10$^4$ of the sorted cells by extracted using TRIzol Reagent (Invitrogen). The microarray data were analyzed using the Bioconductor package (http://www.bioconductor.org/). The signal intensities of probe sets on the microarray platform were normalized using GC-RMA program (http://www.bioconductor.org/). For each platform, the normalized data was analyzed with RankProd program (Hong et al., Bioinformatics, 22, 2825-2827, 2006) to select genes differentially expressed between LSCs and HSCs with the cutoff p value of 0.01 and the false-positive estimation of 0.05%. The gene annotation was obtained from the Ingenuity Pathway Analysis Database and Gene Ontology Annotation Database (http://www.ingenuity.com; http://www.ebi.ac.uk/GOA/).

(6) Quantitative Reverse Transcriptional Polymerase Chain Reaction Analysis (qRT-PCR)

Total RNA was used for the cDNA amplification by WT-Ovation RNA Amplification System (Nugen). PCR was performed by Platinum Quantitative PCR SuperMix (Invitrogen) using LightCycler 480 (Roche Applied Science). The sequences of the double labelled fluorescent probes and gene specific primers were described in table 3 of the Patent Literature 2 (WO2010/110346). The abundance of the respective transcripts was calculated by the standard curve method (Methods, 25, 386-401, 2001). When any of Kruskal-Wallis, Wilcoxon-Mann-Whitney and Student's t-test in Kaleida Graph software package showed P<0.05, it was determined there is a significant difference in the expression level.

(7) Immunofluorescent Labeling and Imaging

Para-formaldehyde-fixed decalcified paraffin-embedded sections were prepared from a femoral bone, and then labelled with a mouse anti-human CD45 monoclonal antibody (DAKO, Denmark) and a mouse anti-human HCK monoclonal antibody (Novus Biologicals). Laser scanning confocal imaging was obtained using Zeiss LSM Exciter and LSM 710 (Carl Zeiss).

(8) The Evaluations of the Viability

Lentiviral transduction and Ck knock-down Cell lines TF1a, HL-60 and K562 were obtained from ATCC (X) and maintained according to manufacturer's instruction. Human AML CD34$^+$CD38-cells were FACS-purified either directly from patient BM/PB or from human AML-engrafted recipient BM. Lentiviral-packed HCK shRNA and control GFP shRNA were obtained from Sigma. Cells were infected at MOI of 100 for 3-4 days, harvested, labeled with mouse anti-hCd44, hCD34 and hCD38 monoclonal antibodies and sorted to obtain HCK shRNA or control GFP shRNA transfected (GFP positive) hCD34$^+$hCD38$^-$ cells. Sorted cells were then cultured in corresponding media in the case of cell lines or HPGM supplemented with recombinant human stem cell factor (SCF, 50 ng/ml), recombinant human thrombopoietin (TPO, 50 ng/ml) and recombinant human FLT3 ligand (FL, 50 ng/ml) in the case of human AML cells. After photomicrographs were taken using Zeiss Axiovert 200 (Carl Zeiss Microimaging), cells were harvested and viability was determined using flow cytometry.

(9) Compounds

The compounds in Examples, comparative compound A (the compound included in the formula (I) of the patent literature 3 WO00/17203), comparative compound B (third compound of claim 72 of the patent literature 3), comparative compound C (tyrosine kinase inhibitor Dasatinib), comparative compound D (PP2 described in THE JOURNAL OF BIOLOGICAL CHEMISTRY, Vol. 271, No. 2, pp. 695-701 (1996)), comparative compound E (PP2 described in Nature Chemical Biology, 4, 691-699 (2008)), comparative compound F (pp20 described in Nature Chemical Biology, 4, 691-699 (2008)), comparative compound G (PI3k inhibitor; PI103) and comparative compound H (mTOR inhibitor; rapamycin) were used.

Although the comparative compound A inhibited the proliferation and survival of human AML CD34$^+$CD38$^-$ cells in a dose-dependent manner in vitro analysis (IC50<1 mM in 9 out of the 19 cases examined), the compound exhibited biochemical properties unfavorable as a therapeutic agent with aqueous solubility less than 1 µM in PMS (pH 7.4) and low metabolic stability (11% and 0% remaining after one hour incubation with human and mouse liver microsomes, respectively).

The compound of Example 1 demonstrated the aqueous solubility (194.3 µM in the PBS (pH 7.4)) similar to the compound C (Dasatinib) with the aqueous solubility of 177.3 µM in PMS (pH 7.4) and high metabolic stability as 54% and 75% remaining after one hour incubation with human and mouse liver microsomes, respectively.

(The Comparative Compound A; RK-24466)

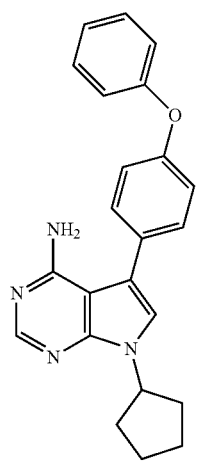 [SMILES: Nc1ncnc2c1c(-c1ccc(Oc3ccccc3)cc1)cn2C1CCCC1]

(The Comparative Compound B)

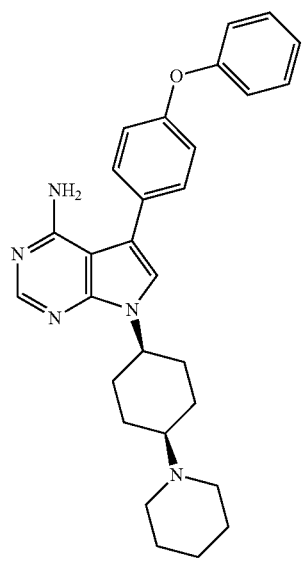 [SMILES: Nc1ncnc2c1c(-c1ccc(Oc3ccccc3)cc1)cn2[C@H]1CC[C@@H](N2CCCCC2)CC1]

(The Comparative Compound C)

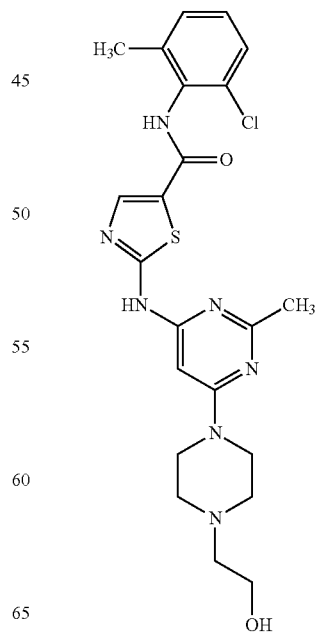

(The Comparative Compound D)

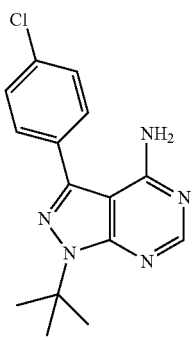 [SMILES: CC(C)(C)n1nc(-c2ccc(Cl)cc2)c2c(N)ncnc21]

(The Comparative Compound E)

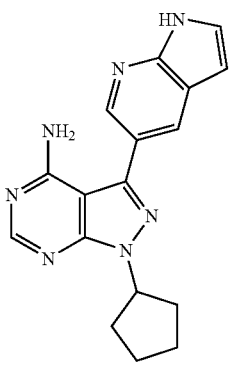 [SMILES: Nc1ncnc2c1c(-c1cnc3[nH]ccc3c1)nn2C1CCCC1]

(The Comparative Compound F)

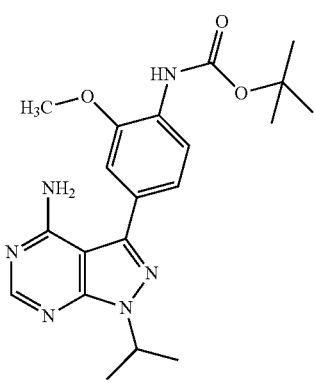 [SMILES: COc1cc(-c2nn(C(C)C)c3ncnc(N)c23)ccc1NC(=O)OC(C)(C)C]

(10) Analysis of Kinase Inhibition In Vitro

Human AML CD34$^+$CD38$^-$ cells were purified or obtained directly from the patient BM/PB or from human AML-engrafted recipient BM. Sorted cells were cultured in HPGM supplemented with recombinant human stem cell factor (SCF, 50 ng/ml), recombinant human thrombopoietin (TPO, 50 ng/ml) and recombinant human FLT3 ligand (FL, 50 ng/ml) under the coexistence of DMSO alone or the comparative compound in the well of tissue culturing 96 wells plate. After 3 days, the cells were harvested, and then evaluated the cell number, surface phenotype and viability using flow cytometry as described above.

The compound of Example 1 exhibited the highest inhibition effect against the proliferation and survival of human AML CD34*CD38$^-$ cells compared with the comparative compound A, comparative compound C (tyrosine kinase inhibitor Dasatinib), comparative compound D (PP2) and other Src family tyrosine kinase (SFK) and downstream kinase inhibitor, comparative compound E (PP121), comparative compound F (PP20), comparative compound G (PI3K inhibitor; PI103) and comparative compound H (mTOR inhibitor; rapamycin).

Furthermore, the viability of the cells treated with these compounds were confirmed by measuring forward scatter (FSC) and side scatter (SSC) using flow cytometry. The cells treated with the compound were labelled with 7AAD label (AnnexinV-FITC Apoptosis Detection Kit, BD) and measured the apoptosis cells using flow cytometry.

As a result of the analysis, the compound of Example 1 exhibited a highly effective in inhibition against the proliferation and survival of leukemia stem cells.

Compared with comparative compound C and comparative compound D at the treatment concentration of 0 nM, 100 nM or 1000 nM, the compound of Example 1 had a more potent effect on inhibition against the proliferation and survival of leukemia stem cells at each concentration (Table 1). Table 1 represents percentage of cell number treated with each compound in the way the cell number treated with DMSO alone is 100%.

TABLE 1

| Treatment concentration | Compound of Example 1 | Comparative compound C | Comparative compound D |
|---|---|---|---|
| 0 nM | 100% | 100% | 100% |
| 100 nM | 13.6% | 96.0% | 95.6% |
| 1000 nM | 9.5% | 89.4% | 94.1% |

Example 61

In Vitro Kinase Inhibition Analysis 2

The kinase inhibition analysis below were performed according to the material and methods described in Example 60.

The cell samples were prepared by purifying AML CD34$^+$CD38$^-$ cells using FACS of blood samples obtained from the acute myeloid leukemia patients in the table 2-4, or by obtaining directly from patients BM/PB or human AML-engrafted recipient BM. Each sorted cells was cultured in HPGM supplemented with recombinant human stem cell factor (SCF, 50 ng/ml), recombinant human thrombopoietin (TPO, 50 ng/ml) and recombinant human FLT3 ligand (FL, 50 ng/ml) with the addition of DMSO alone, the compound of Example 1, comparative compound A or comparative compound D (SFK inhibitor, PP2) in the well of tissue culturing 96 wells plate.

After 3 days, cells were harvested from the wells, and cell number, surface phenotype, and viability were analyzed using flow cytometry as described above.

As a result of the analyses, similar to Example 60, the compound of Example 1 exhibited a highly effective in inhibition against the proliferation and survival of leukemia stem cells. Surprisingly, the compound of Example 1 had a remarkable effect of inhibition on the proliferation and survival of leukemia stem cell having Flt3/ITD mutations.

Table 2 shows the result of treatment with 500 nM or 1 μM of the compound of Example 1.

Table 3 shows the result of treatment with 500 nM or 1 μM of comparative compound A.

Table 4 shows the result of treatment with 500 nM or 1 μM of comparative compound D.

"FLT3 Type" represents about mutations of FLT3 gene, ITD means cell sample having mutated FLT3 gene having FLT3/ITD mutations, and WT means cell sample having normal FLT3 gene.

"(average)" represents the average score of treatment by each compound in the group of cell sample having ITD mutated FLT3 gene or cell sample having normal FLT3 gene.

TABLE 2

| Sample code | FLT3 Type | DMSO (%) | Compound of Example 1 500 nM (%) | Compound of Example 1 1 μM (%) |
|---|---|---|---|---|
| A | ITD | 100 | 1.2 | 1.3 |
| E | ITD | 100 | 3.5 | 4.5 |
| U | ITD | 100 | 11.3 | 11.9 |
| D | ITD | 100 | 7.6 | n.a. |
| C | ITD | 100 | 10.5 | n.a. |
| V | ITD | 100 | 14.4 | n.a. |
| W | ITD | 100 | 33.4 | 27.7 |
| X | ITD | 100 | 9.2 | 8.8 |
| (average) | | | 11.4 | 10.8 |
| N | WT | 100 | 40.3 | n.a. |
| K | WT | 100 | 85.1 | 65 |
| Y | WT | 100 | n.a. | 91.9 |
| L | WT | 100 | 14.1 | 14.3 |
| O | WT | 100 | 85.8 | 83.3 |
| Z | WT | 100 | 72.9 | n.a. |
| I | WT | 100 | 23.9 | n.a. |
| AA | WT | 100 | 81.8 | 43 |
| AB | WT | 100 | 79.7 | 30 |
| F | WT | 100 | 85.9 | 75.1 |
| M | WT | 100 | 37.9 | n.a. |
| P | WT | 100 | 27.7 | 21.3 |
| J | WT | 100 | 80.2 | 47.2 |
| R | WT | 100 | 30 | 28.8 |
| H | WT | 100 | 65.6 | 59.8 |
| Q | WT | 100 | 53.9 | 46.3 |
| G | WT | 100 | 97 | 89 |
| S | WT | 100 | 79.5 | 76.7 |
| (average) | | | 61.3 | 55.1 |

TABLE 3

| Sample code | FLT3 Type | DMSO (%) | Comparative compound A 500 nM (%) | Comparative compound A 1 μM (%) |
|---|---|---|---|---|
| B | ITD | 100 | n.a. | 41.8 |
| C | ITD | 100 | 58.5 | 57.7 |
| D | ITD | 100 | 84.3 | 63.6 |
| E | ITD | 100 | 16.5 | n.a. |
| (average) | | | 53.1 | 54.4 |
| F | WT | 100 | n.a. | 66.1 |
| G | WT | 100 | 65.7 | 59.5 |
| H | WT | 100 | 86.7 | 49.4 |
| I | WT | 100 | 82.1 | 61.8 |
| J | WT | 100 | n.a. | 57.4 |
| K | WT | 100 | 87.9 | n.a. |
| L | WT | 100 | 77.5 | 69.8 |
| M | WT | 100 | n.a. | 69 |
| N | WT | 100 | 67.9 | 42.5 |
| O | WT | 100 | n.a. | 78.8 |
| P | WT | 100 | 61 | 40 |
| Q | WT | 100 | n.a. | 48.9 |
| R | WT | 100 | n.a. | 32.7 |
| S | WT | 100 | 87.6 | 88.6 |
| T | WT | 100 | 98.7 | 88.4 |
| (average) | | | 79.5 | 60.9 |

TABLE 4

| Sample code | FLT3 Type | DMSO (%) | Comparative compound D 500 nM (%) | Comparative compound D 1 μM (%) |
|---|---|---|---|---|
| B | ITD | 100 | n.a. | 97.1 |
| C | ITD | 100 | n.a. | 96.4 |
| D | ITD | 100 | n.a. | 95.5 |
| E | ITD | 100 | 91.5 | n.a. |
| (average) | | | 91.5 | 96.3 |
| H | WT | 100 | 77.9 | 66.6 |
| I | WT | 100 | 87.1 | 71.6 |
| J | WT | 100 | n.a. | 67.4 |
| K | WT | 100 | 80.2 | 75.4 |
| L | WT | 100 | 96.7 | 80.9 |
| M | WT | 100 | n.a. | 90.9 |
| N | WT | 100 | 87.7 | 85.1 |
| O | WT | 100 | n.a. | 94.4 |
| P | WT | 100 | n.a. | 66.1 |
| (average) | | | 85.9 | 77.6 |

Example 62

In Vitro Kinase Inhibition Analysis 2

The kinase inhibition analysis below were performed according to the material and methods described in Example 60.

The cell samples were prepared by purifying AML $CD34^+$ $CD38^-$ cells using FACS of blood samples obtained from the acute myeloid leukemia patients having FLT3-ITD mutations (#1, #2), or by obtaining directly from patients BM/PB or human AML-engrafted recipient BM. Each sorted cells was cultured in HPGM supplemented with recombinant human stem cell factor (SCF, 50 ng/ml), recombinant human thrombopoietin (TPO, 50 ng/ml) and recombinant human FLT3 ligand (FL, 50 ng/ml) in the well of tissue culturing 96 wells plate with the addition of DMSO alone or the compound described in Examples 1, 2, 6, 7, 8, 43, 45, 48, 56 or 57 for instance of compound having inhibition effect on both HCK and FLT3.

After 3 days, cells were harvested from the wells, and cell number, surface phenotype, and viability were analyzed using flow cytometry as described above.

As a result of the analyses, each compounds also exhibited a highly effective in inhibition against the proliferation and survival of leukemia stem cells similar to the compound of Example 1 in the way the cell number treated with DMSO alone is 100% (Table 5).

TABLE 5

| Test Compound | Patient #1 | Patient #2 |
|---|---|---|
| Compound of Example 1 | 13.5% | 15.6% |
| Compound of Example 2 | 33.4% | 14.0% |
| Compound of Example 6 | 20.9% | 17.6% |
| Compound of Example 7 | 17.1% | 13.9% |
| Compound of Example 8 | n.d. | 5.5% |
| Compound of Example 43 | 16.0% | 40.2% |
| Compound of Example 45 | n.d. | 16% |
| Compound of Example 48 | 12.7% | 12.1% |

TABLE 5-continued

| Test Compound | Patient #1 | Patient #2 |
|---|---|---|
| Compound of Example 56 | 24.5% | n.d. |
| Compound of Example 57 | 18.0% | 35.0% |

Example 63

Kinase Inhibition Analysis of the Compound Having FLT3 Inhibition Effect

AML CD34$^+$CD38$^-$ cells having FLt3/ITD mutations were purified using FACS or obtaining directly from patients BM/PB or human AML-engrafted recipient BM. Sorted cells was cultured in HPGM supplemented with recombinant human stem cell factor (SCF, 50 ng/ml), recombinant human thrombopoietin (TPO, 50 ng/ml) and recombinant human FLT3 ligand (FL, 50 ng/ml) in the well of tissue culturing 96 wells plate under the coexistence of the compound of Example 4 and Crenolanib at the various concentrations. After 3 days, the cells were harvested, and then evaluated the cell number, surface phenotype and viability using flow cytometry as described above.

The cells were evaluated the cell number, surface phenotype and viability in the way the cell number treated with 0 μM compound of Example 4 and 0 μM Crenolanib is 100%.

As a result, the effect of inhibition on the proliferation and survival was significant by inhibiting both FLt3 activity and HCK activity (Table 6).

TABLE 6

| | Compound of Example 4 0 nM | Compound of Example 4 30 nM | Compound of Example 4 100 nM | Compound of Example 4 300 nM |
|---|---|---|---|---|
| Crenolanib 0 nM | 100% | 92.9% | 71.4% | 59.2% |
| Crenolanib 10 nM | 56.8% | 43.3% | 38.3% | 24.6% |
| Crenolanib 30 nM | 26.3% | 17.7% | 17.0% | 7.2% |

Example 64

Assessment of Leukemia Incidence Ability of the Treated AMLCD34$^+$CD38$^-$ Cells For examining leukemia incidence ability of the treated AMLCD34$^+$CD38$^-$ cells, 7ADD$^-$CD45$^+$ cells were sorted from cells harvested from each well, and transplanted into NSG mouse newborns as described above. Transplant recipients underwent retroorbital phlebotomy every 3 weeks starting at 6 weeks after transplantation to assess AML engraftment. Survival was estimated with the Kaplan-Meier method.

Figure 3:
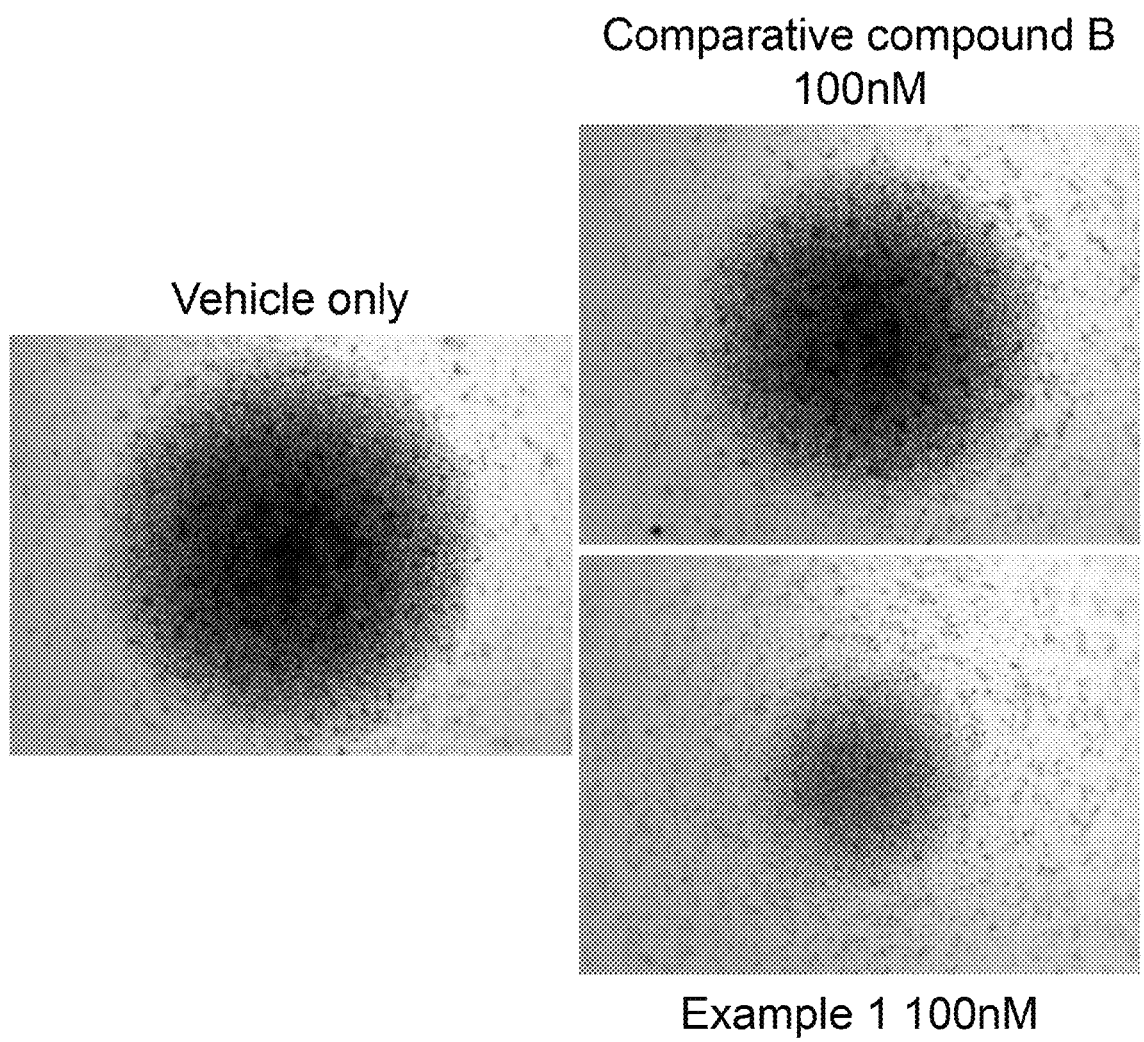
FIG. 3 shows the results of analysis of inhibitory effects of a test compound on the survival of human AML CD34$^+$CD38$^-$ cells.
Figure 4:
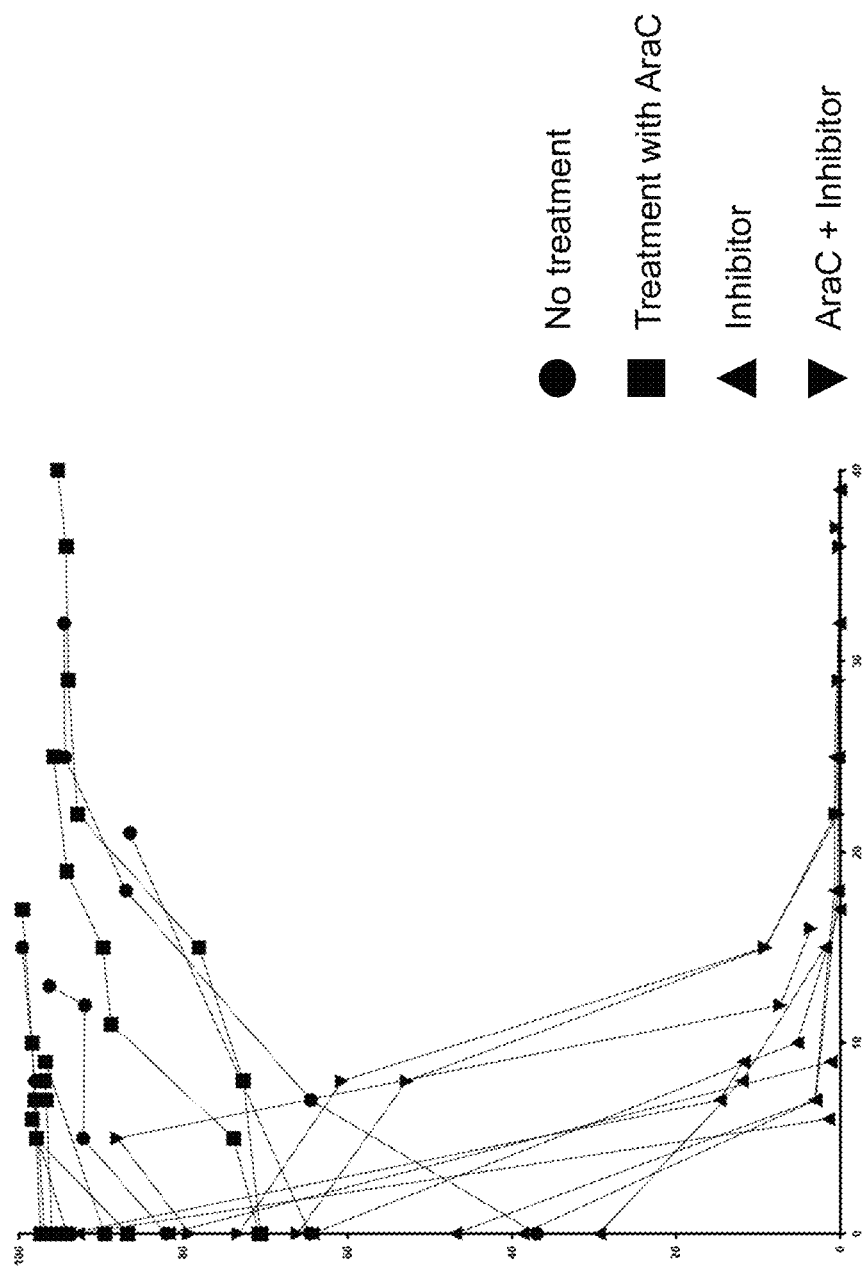
FIG. 4 shows the results of in vivo studies in which vehicles only (non-treatment), the compound (an inhibitor) of Example 1 only, AraC only, or AraC in combination with the compound (an inhibitor) of Example 1 (30 mg/kg ip bid) had been administered.
Figure 5:
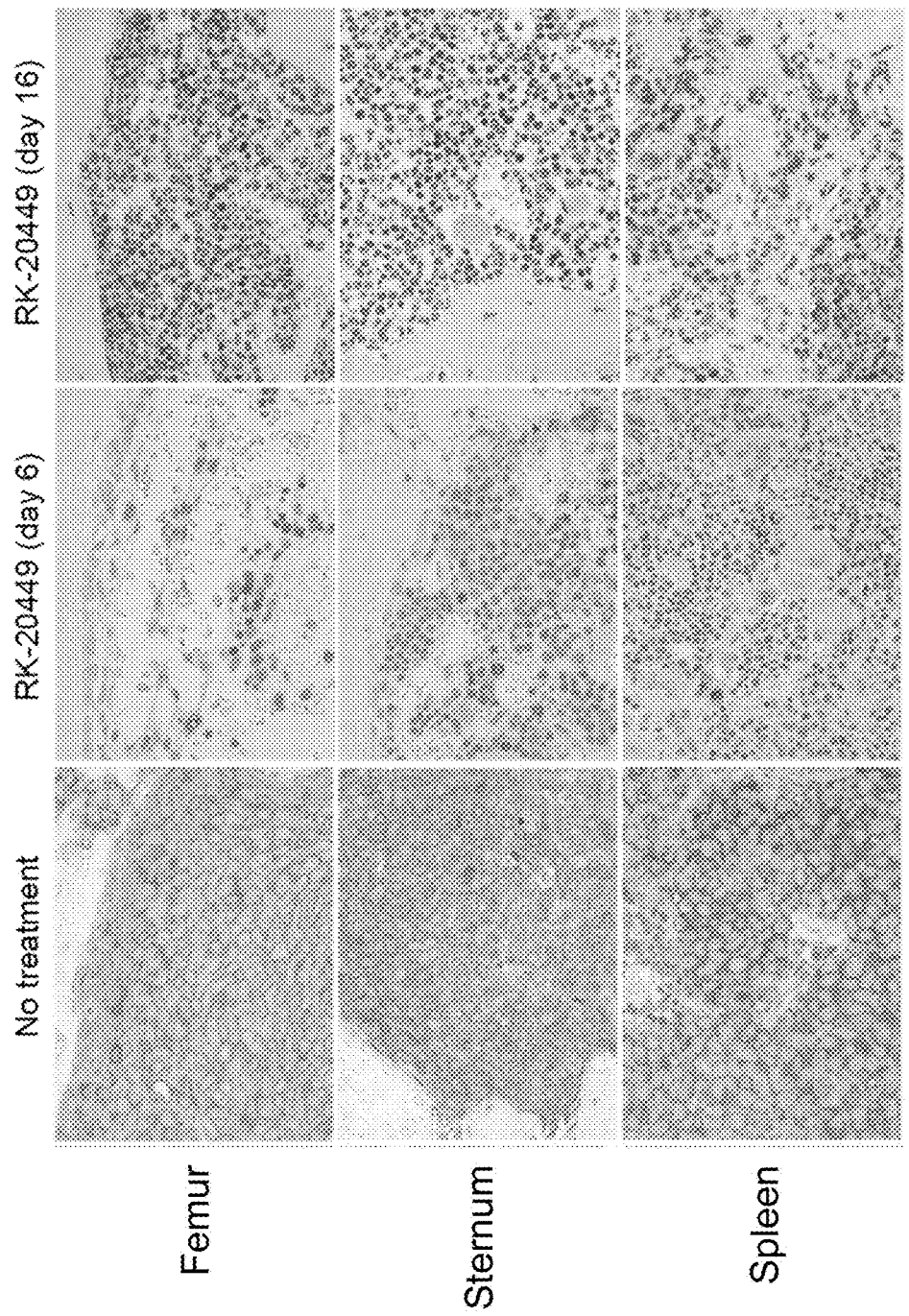
FIG. 5 shows the effects of the compound (an inhibitor) of Example 1 examined in the in vivo studies on a recipient into which the AML cells obtained from a patient with a chemotherapy-resistant disease has been engrafted. Asterisks in the photographs indicate positions of surviving AML cells.

Although the effect on the proliferation and survival of human CD34$^+$CD38$^-$ cells by the comparative compound B that is described in third of claim 72 in patent literature 3 was verified, little effect of inhibition was confirmed (FIG. 3).

Example 65

(1) In Vitro Kinase Inhibition Analysis

For the study of short treatment in vivo, NOD/SCID/IL2rg$^{null}$ littermates engrafted AML derived from seven patient (U58#1, SH3, KH, U62, U142, AK, U115) received intraperitoneal (ip) injection of vehicle alone or 30 mg/kg test compound twice daily for 18 days of treatment or when they became moribund, whichever came earlier. In study of in vivo treatment of recipient engrafted AML cells obtained from the patient of chemotherapy-resistant disease, littermates received the injection of vehicle alone, test compound alone (30 mg/kg ip bid), AraC alone (480 mg/kg ip x1) or the combination of AraC (480 mg/kg ip x1) followed by test compound (30 mg/kg ip bid).

The mice were sacrificed when they became moribund or after 6 weeks of treatment. Then human AML chimerism in BM, spleen, and PB were assessed. Human AML chimerism was calculated by identifying whole human leukemia cells by hCD45, human leukemia stem cells by hCD45$^+$hCD34$^+$hCD38$^-$, mouse leukocyte by mouse CD45, and mouse erythrocyte by mouse Ter119. As a result, significant effects were shown in case of the single administration of the compound (inhibitor) of Example 1 and in case of combined administration of the AraC and the compound (inhibitor) of Example 1.

The measure results of apoptosis in BM and spleen using AnnexinV and 7AAD label (AnnexinV-FITC Apoptosis Detection kit, BD) were obtained.

(2) Statistical Analysis

Numerical data were presented as means±standard error. The differences were examined using two-tailed t-test (GraphPad Prism, GraphPad, USA). P value below 0.05 was deemed significant. Survival was estimated by the Kaplan-Meier method and curves were compared by Log-rank (Mantel-cox) test.

Example 66

The effects of HCK expression decrease using short hairpin RNA (shRNA) was examined to assess the functional role of HCK in the LSC.

Figure 6:
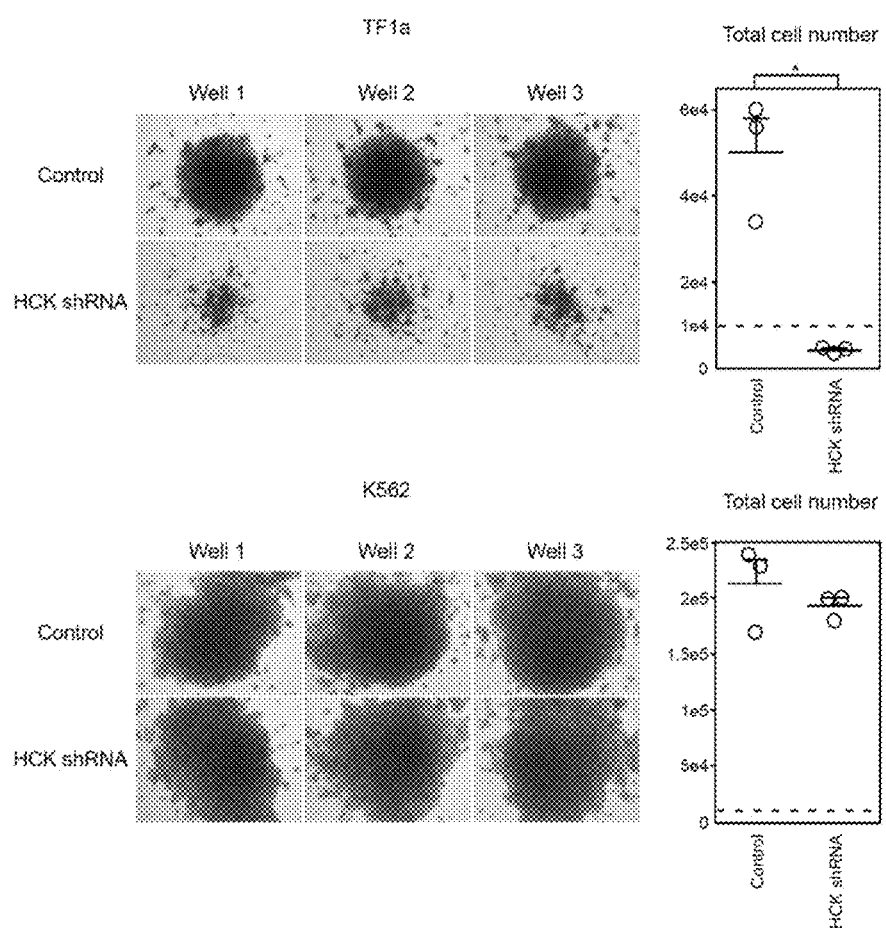
FIG. 6 shows the effects of short hairpin RNA (shRNA) for reducing HCK expression.

The human AML cell line TF1a and the human chronic myeloid leukemia (CML) cell line K562 were transfected with HCK shRNA and control shRNA. Green fluorescent protein (GFP) positive human CD34$^+$CD38$^-$ cells were purified using fluorescent activated cell sorting (FACS) and cultured in vitro for 7 days to determine the effect of HCK downregulation on proliferation and survival. Reduced HCK expression led to significant inhibition of proliferation and survival of TF1a cell (which expressed HCK before transduction) whereas the effect was not shown in K562 cells (which do not express HCK). HCK shRNA did not affect the transcript levels of the SFK family Lyn and Src, reportedly involved in human AML pathogenesis. These findings show that HCK expression is required for proliferation and survival of human AML cells and that pharmacologic inhibition of HCK can eliminate human AML leukemia stem cells (FIG. 6).

Figure 7:
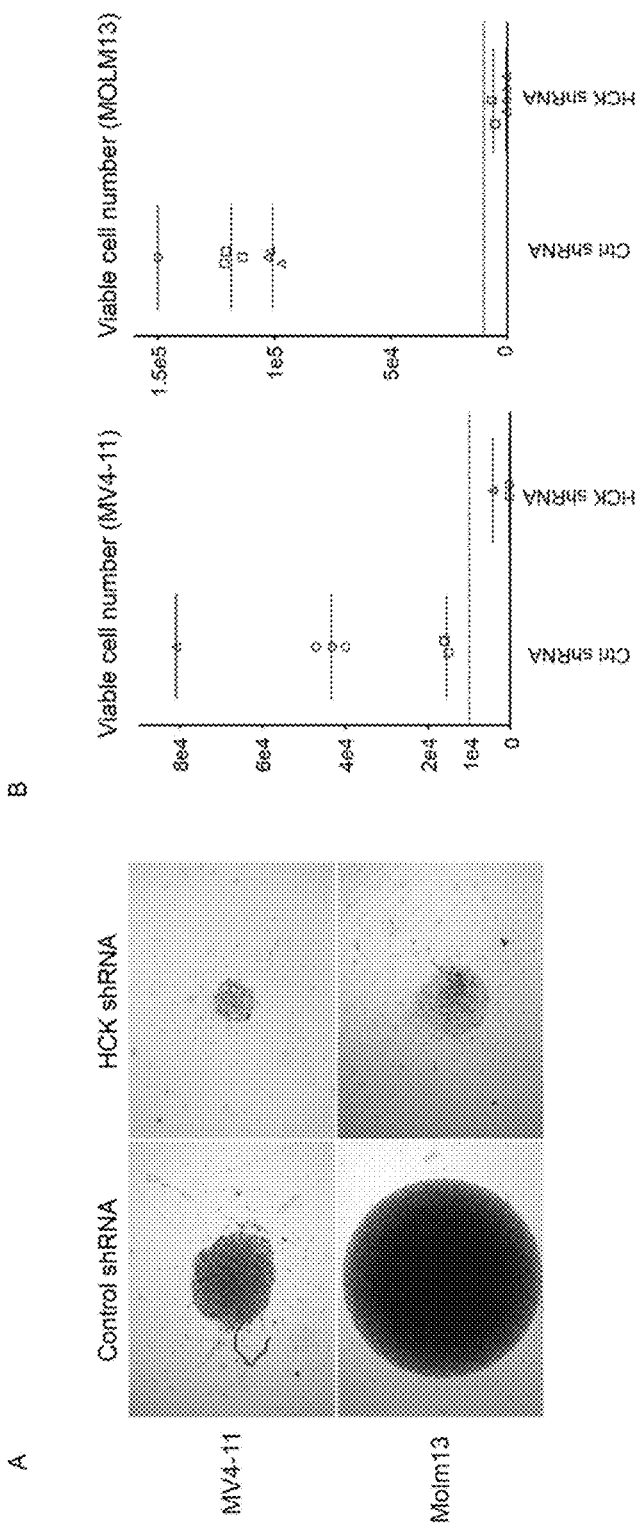
FIG. 7 shows the effects of HCK inhibition on human AML with FLT3/ITD mutation.

The significance of HCK expression in the human AML having FLT3/ITD mutations by HCK shRNA was examined because constitutive activation of FLT3 (most frequently in the form of FLT3/ITD mutations) is commonly associated with normal karyotype AML. In two human AML cell lines having FLT3/ITD mutations (MV-4-11 and Molm13), the inhibition of HCK by shRNA reduced both viable cell number and viability in the remaining cells. These findings show that HCK inhibition is effective against human AML having FLT3/ITD mutations (FIG. 7).

The invention claimed is:

1. A method for killing leukemia stem cells comprising a step of administering a therapeutically effective amount of a compound represented by formula (I), or a salt thereof to an individual with acute myeloid leukemia in which leukemia stem cells are present:

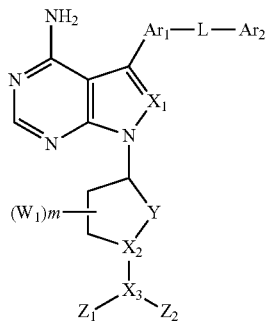

wherein
$Ar_1$ represents a substituted or unsubstituted arylene group;
$Ar_2$ represents a substituted or unsubstituted aryl or heteroaryl group;
L represents an oxygen atom or —NHCO—;
$X_1$ represents CH;
$X_2$ and $X_3$ each independently represent CH or a nitrogen atom, provided that $X_2$ and $X_3$ are not the same;
Y represents a $C_{1-3}$-alkylene group;
$W_1$, which is a substituent on the ring including Y and $X_2$, each independently represent a $C_{1-6}$-alkyl group;
m is an integer from 0 to 3; and
$Z_1$ and $Z_2$ each independently represent a hydrogen atom, a $C_{1-6}$-alkyl group, an amino-$C_{1-6}$-alkyl group, a $C_{1-6}$-alkylamino-$C_{1-6}$-alkyl group, a di($C_{1-6}$-alkyl)amino-$C_{1-6}$-alkyl group, a hydroxy-$C_{1-6}$-alkyl group, a $C_{1-6}$-alkoxy-$C_{1-6}$-alkyl group, a $C_{2-7}$-aliphatic acyl group, a carboxy-$C_{1-6}$-alkyl group, a carbamoyl-$C_{1-6}$-alkyl group, a substituted or unsubstituted saturated heterocyclic group, a substituted or unsubstituted aryl-$C_{1-6}$-alkyl group, a substituted or unsubstituted heteroaryl-$C_{1-6}$-alkyl group, a substituted or unsubstituted arylcarbonyl group, or a substituted or unsubstituted heteroarylcarbonyl group, excluding the case in which both $Z_1$ and $Z_2$ represent hydrogen atoms;
when $X_2$ represents CH and $X_3$ represents a nitrogen atom, $Z_1$ and $Z_2$ may form a substituted or unsubstituted, monocyclic or polycyclic heterocyclic group including $X_3$ and containing as a ring member two or more hetero atoms selected from the group consisting of oxygen, sulfur, and nitrogen atoms, or
when $X_2$ represents a nitrogen atom and $X_3$ represents CH, $Z_1$ and $Z_2$ may form a substituted or unsubstituted, monocyclic or polycyclic heterocyclic group including $X_3$ and containing a heteroatom selected from among oxygen, sulfur, and nitrogen atoms.

2. The method according to claim 1, wherein the individual in which leukemia stem cells are present has recurrent acute myeloid leukemia.

3. The method according to claim 1, wherein Flt3/ITD mutations are present in the leukemia stem cells.

4. A method for treatment or inhibition of recurrence of acute myeloid leukemia, comprising a step of administering a therapeutically effective amount of the compound represented by formula (I) defined in claim 1, or a salt thereof to an individual in need thereof.

5. The method according to claim 4, wherein the compound is represented by formula (I), wherein $Ar_2$ represents a substituted or unsubstituted aryl group, and L represents an oxygen atom.

6. The method according to claim 1, wherein the compound is represented by formula (I), wherein $X_2$ represents CH, $X_3$ represents a nitrogen atom, and $Z_1$ and $Z_2$ form a substituted or unsubstituted, monocyclic or polycyclic heterocyclic group including $X_3$ and containing as a ring member two or more hetero atoms selected from the group consisting of oxygen, sulfur, and nitrogen atoms.

7. The method according to claim 4, wherein the compound is 7-[trans-4-(4-methyl-1-piperazinyl)cyclohexyl]-5-(4-phenoxyphenyl)-7H-pyrrolo[2,3-d] pyrimidin-4-amine.

8. The method according to claim 1, wherein the compound is represented by formula (I), wherein $Z_1$ represents a hydrogen atom and $Z_2$ represents a substituted or unsubstituted saturated heterocyclic group, a substituted or unsubstituted heteroaryl-$C_{1-6}$-alkyl group, or a substituted or unsubstituted heteroarylcarbonyl group.

9. The method according to claim 1, wherein the compound is represented by formula (I), wherein $X_2$ represents a nitrogen atom, $X_3$ represents CH, and $Z_1$ and $Z_2$ form a substituted or unsubstituted, monocyclic or polycyclic heterocyclic group including $X_3$ and containing a hetero atom selected from among oxygen, sulfur, and nitrogen atoms.

10. The method according to claim 4, wherein the compound is represented by formula (I), wherein $Ar_1$ represents a substituted or unsubstituted arylene group, $Ar_2$ represents a substituted or unsubstituted heteroaryl group, and L represents —NHCO—.

11. The method according to claim 10, which further comprises administering an agent exerting inhibitory effects on FLT3 to the individual.

12. The method according to claim 11, wherein the agent is at least one agent selected from Crenolanib, Lestautirinib, PKC412, Tandutinib, Sunitinib, Sorafenib, Linifanib, Dovitinib, KW-2449, Quizartinib, Dovitinib Dilactic acid, Cabozanitib, TG101209, Amuvatinib, and ENMD-2076.

13. The method according to claim 1, wherein the compound is represented by formula (I), wherein $Ar_2$ represents a substituted or unsubstituted aryl or heteroaryl group, and L represents —NHCO—.

14. The method according to claim 13, wherein the compound is selected from:
N-(4-(4-amino-7-((cis)-4-(3-methyl-5,6-dihydro[1,2,4]triazolo[4,3-a]pyrazin-7(8H)-yl) cyclohexyl)-7H-pyrrolo[2,3-d]pyrimidin-5-yl)-2-methoxyphenyl)-1-methyl-1H-indole-2-carboxamide,
N-(4-(4-amino-7-((trans)-4-(3-methyl-5,6-dihydro[1,2,4]triazolo[4,3-a]pyrazin-7(8H)-yl) cyclohexyl)-7H-pyrrolo[2,3-d]pyrimidin-5-yl)-2-methoxyphenyl)-1-methyl-1H-indole-2-carboxamide,
N-(4-(4-amino-7-((trans)-4-(4-methylpiperazin-1-yl)cyclohexyl)-7H-pyrrolo[2,3-d]pyrimidin-5-yl)phenyl)-1-methyl-1H-indole-2-carboxamide,
N-(4-(4-amino-7-((cis)-4-(4-methylpiperazin-1-yl)cyclohexyl)-7H-pyrrolo[2,3-d]pyrimidin-5-yl)-2-methoxyphenyl)-1-methyl-1H-indole-2-carboxamide,
N-(4-(4-amino-7-((trans)-4-(4-methylpiperazin-1-yl)cyclohexyl)-7H-pyrrolo[2,3-d]pyrimidin-5-yl)-2-methoxyphenyl)-1-methyl-1H-indole-2-carboxamide,
N-(4-(4-amino-7-((trans)-4-(3-(trifluoromethyl)-5,6-dihydro[1,2,4]triazolo[4,3-a]pyrazin-7(8H)-yl)cyclohexyl)-7H-pyrrolo[2,3-d]pyrimidin-5-yl)-2-methoxyphenyl)-1-methyl-1H-indole-2-carboxamide, N-(4-(4-amino-7-((cis)-4-(3-ethyl-5,6-dihydro[1,2,4]triazolo[4,3-a]pyrazin-7(8H)-yl) cyclohexyl)-7H-pyrrolo[2,3-d]pyrimidin-5-yl)-2-methoxyphenyl)-1-methyl-1H-indole-2-carboxamide, N-(4-(4-amino-7-((trans)-4-(3-ethyl-5,6-dihydro[1,2,4]triazolo[4,3-a]pyrazin-7(8H)-yl) cyclohexyl)-7H-pyrrolo[2,3-d]pyrimidin-5-yl)-2-methoxyphenyl)-1-methyl-1H-indole-2-carboxamide, N-(4-(4-amino-7-((cis)-4-(3-isopropyl-5,6-dihydro[1,2,4]triazolo[4,3-a]pyrazin-7(8H)-yl) cyclohexyl)-7H-pyrrolo[2,3-d]pyrimidin-5-yl)-2-methoxyphenyl)-1-methyl-1H-indole-2-carboxamide, N-(4-(4-amino-7-((trans)-4-(3-isopropyl-5,6-dihydro[1,2,4]triazolo[4,3-a]pyrazin-7(8H)-yl) cyclohexyl)-7H-pyrrolo[2,3-d]pyrimidin-5-yl)-2-methoxyphenyl)-1-methyl-1H-indole-2-carboxamide, N-(4-(4-amino-7-((cis)-4-(3-methyl-5,6-dihydroimidazolo[1,5-a]pyrazin-7(8H)-yl)cyclohexyl)-7H-pyrrolo[2,3-d]pyrimidin-5-yl)-2-methoxyphenyl)-1-methyl-1H-indole-2-carboxamide, N-(4-(4-amino-7-((trans)-4-(3-methyl-5,6-dihydroimidazolo[1,5-a]pyrazin-7(8H)-yl) cyclohexyl)-7H-pyrrolo[2,3-d]pyrimidin-5-yl)-2-methoxyphenyl)-1-methyl-1H-indole-2-carboxamide, N-(4-(4-amino-7-((cis)-4-(2-methyl-6,7-dihydropyrazolo[1,5-a]pyrazin-5 (4H)-yl)cyclohexyl)-7H-pyrrolo[2,3-d]pyrimidin-5-yl)-2-methoxyphenyl)-1-methyl-1H-indole-2-carboxamide, N-(4-(4-amino-7-((cis)-4-(6, 7-dihydropyrazolo[1,5-a]pyrazin-5 (4H)-yl)cyclohexyl)-7H-pyrrolo[2,3-d]pyrimidin-5-yl)-2-methoxyphenyl)-1-methyl-1H-indole-2-carboxamide, and N-(4-(4-amino-7-((trans)-4-(3-methyl-5,6-dihydroimidazo[1,2-a]pyrazin-7(8H)-yl)cyclohexyl)-7H-pyrrolo[2,3-d]pyrimidin-5-yl)-2-methoxyphenyl)-1-methyl-1H-indole-2-carboxamide.

15. A pyrrolo[2,3-d]pyrimidine derivative, or a salt thereof, wherein the derivative is selected from:

N-(4-(4-amino-7-((trans)-4-(4-methylpiperazin-1-yl)cyclohexyl)-7H-pyrrolo[2,3-d]pyrimidin-5-yl)phenyl)-3-phenylpropanamide, N-(4-(4-amino-7-((cis)-4-(3-methyl-5,6-dihydro[1,2,4]triazolo[4,3-a]pyrazin-7(8H)-yl) cyclohexyl)-7H-pyrrolo[2,3-d]pyrimidin-5-yl)-2-methoxyphenyl)-1-methyl-1H-indole-2-carboxamide, N-(4-(4-amino-7-((trans)-4-(3-methyl-5,6-dihydro[1,2,4]triazolo[4,3-a]pyrazin-7(8H)-yl) cyclohexyl)-7H-pyrrolo[2,3-d]pyrimidin-5-yl)-2-methoxyphenyl)-1-methyl-1H-indole-2-carboxamide, N-(4-(4-amino-7-((trans)-4-(4-methylpiperazin-1-yl)cyclohexyl)-7H-pyrrolo[2,3-d]pyrimidin-5-yl)phenyl)-1-methyl-1H-indole-2-carboxamide, N-(4-(4-amino-7-((cis)-4-(4-methylpiperazin-1-yl)cyclohexyl)-7H-pyrrolo[2,3-d]pyrimidin-5-yl)-2-methoxyphenyl)-1-methyl-1H-indole-2-carboxamide, N-(4-(4-amino-7-((trans)-4-(4-methylpiperazin-1-yl)cyclohexyl)-7H-pyrrolo[2,3-d]pyrimidin-5-yl)-2-methoxyphenyl)-1-methyl-1H-indole-2-carboxamide, N-(4-(4-amino-7-((trans)-4-(3-(trifluoromethyl)-5,6-dihydro[1,2,4]triazolo[4,3-a]pyrazin-7(8H)-yl)cyclohexyl)-7H-pyrrolo[2,3-d]pyrimidin-5-yl)-2-methoxyphenyl)-1-methyl-1H-indole-2-carboxamide, N-(4-(4-amino-7-((cis)-4-(3-ethyl-5,6-dihydro[1,2,4]triazolo[4,3-a]pyrazin-7(8H)-yl) cyclohexyl)-7H-pyrrolo[2,3-d]pyrimidin-5-yl)-2-methoxyphenyl)-1-methyl-1H-indole-2-carboxamide, N-(4-(4-amino-7-((trans)-4-(3-ethyl-5,6-dihydro[1,2,4]triazolo[4,3-a]pyrazin-7(8H)-yl) cyclohexyl)-7H-pyrrolo[2,3-d]pyrimidin-5-yl)-2-methoxyphenyl)-1-methyl-1H-indole-2-carboxamide, N-(4-(4-amino-7-((cis)-4-(3-isopropyl-5,6-dihydro[1,2,4]triazolo[4,3-a]pyrazin-7(8H)-yl) cyclohexyl)-7H-pyrrolo[2,3-d]pyrimidin-5-yl)-2-methoxyphenyl)-1-methyl-1H-indole-2-carboxamide, N-(4-(4-amino-7-((trans)-4-(3-isopropyl-5,6-dihydro[1,2,4]triazolo[4,3-a]pyrazin-7(8H)-yl) cyclohexyl)-7H-pyrrolo[2,3-d]pyrimidin-5-yl)-2-methoxyphenyl)-1-methyl-1H-indole-2-carboxamide, N-(4-(4-amino-7-((cis)-4-(3-methyl-5,6-dihydroimidazolo[1,5-a]pyrazin-7(8H)-yl)cyclohexyl)-7H-pyrrolo[2,3-d]pyrimidin-5-yl)-2-methoxyphenyl)-1-methyl-1H-indole-2-carboxamide, N-(4-(4-amino-7-((trans)-4-(3-methyl-5,6-dihydroimidazolo[1,5-a]pyrazin-7(8H)-yl) cyclohexyl)-7H-pyrrolo[2,3-d]pyrimidin-5-yl)-2-methoxyphenyl)-1-methyl-1H-indole-2-carboxamide, N-(4-(4-amino-7-((cis)-4-(2-methyl-6,7-dihydropyrazolo[1,5-a]pyrazin-5(4H)-yl)cyclohexyl)-7H-pyrrolo[2,3-d]pyrimidin-5-yl)-2-methoxyphenyl)-1-methyl-1H-indole-2-carboxamide, N-(4-(4-amino-7-((cis)-4-(6,7-dihydropyrazolo[1,5-a]pyrazin-5(4H)-yl)cyclohexyl)-7H-pyrrolo[2,3-d]pyrimidin-5-yl)-2-methoxyphenyl)-1-methyl-1H-indole-2-carboxamide, and N-(4-(4-amino-7-((trans)-4-(3-methyl-5,6-dihydroimidazo[1,2-a]pyrazin-7(8H)-yl)cyclohexyl)-7H-pyrrolo[2,3-d]pyrimidin-5-yl)-2-methoxyphenyl)-1-methyl-1H-indole-2-carboxamide.

16. A method for killing leukemia stem cells comprising a step of administering a therapeutically effective amount of N-(4-(4-amino-7-((trans)-4-(4-methylpiperazin-1-yl)cyclohexyl)-7H-pyrrolo[2,3-d]pyrimidin-5-yl)phenyl)-3-phenylpropanamide or a salt thereof to an individual in which leukemia stem cells are present.

17. The method according to claim 16, wherein the individual in which leukemia stem cells are present has recurrent acute myeloid leukemia.

18. The method according to claim 16, wherein Flt3/ITD mutations are present in the leukemia stem cells.

19. A method for treatment or inhibition of recurrence of acute myeloid leukemia, comprising a step of administering a therapeutically effective amount of N-(4-(4-amino-7-((trans)-4-(4-methylpiperazin-1-yl)cyclohexyl)-7H-pyrrolo[2,3-d]pyrimidin-5-yl)phenyl)-3-phenylpropanamide or a salt thereof to an individual in need thereof.

20. The method according to claim 19, which further comprises administering an agent exerting inhibitory effects on FLT3 to the individual.

21. The method according to claim 20, wherein the agent is at least one agent selected from Crenolanib, Lestautirinib, PKC412, Tandutinib, Sunitinib, Sorafenib, Linifanib, Dovitinib, KW-2449, Quizartinib, Dovitinib Dilactic acid, Cabozanitib, TG101209, Amuvatinib, and ENMD-2076.

* * * * *